US008536135B2

(12) United States Patent
Mascarenhas

(10) Patent No.: US 8,536,135 B2
(45) Date of Patent: Sep. 17, 2013

(54) ADAPTIVE BIOCHEMICAL SIGNATURES

(75) Inventor: Desmond Mascarenhas, Los Altos Hills, CA (US)

(73) Assignee: Ontherix, Inc., Sunnyvale, CA (US)

(*) Notice: Subject to any disclaimer, the term of this patent is extended or adjusted under 35 U.S.C. 154(b) by 0 days.

(21) Appl. No.: 13/035,844

(22) Filed: Feb. 25, 2011

(65) Prior Publication Data

US 2011/0212079 A1  Sep. 1, 2011

Related U.S. Application Data

(63) Continuation-in-part of application No. 12/933,381, filed as application No. PCT/US2009/037695 on Mar. 19, 2009, which is a continuation-in-part of application No. 12/077,575, filed on Mar. 19, 2008, now Pat. No. 7,662,624.

(60) Provisional application No. 61/038,013, filed on Mar. 19, 2008, provisional application No. 61/155,091, filed on Feb. 24, 2009.

(51) Int. Cl.
*A61K 38/17* (2006.01)

(52) U.S. Cl.
USPC ........ 514/21.3; 514/15.4; 514/15.6; 514/18.6

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 5,824,467 A | 10/1998 | Mascarenhas | |
| 5,861,273 A | 1/1999 | Olson et al. | |
| 5,914,254 A | 6/1999 | Mascarenhas et al. | |
| 6,087,090 A | 7/2000 | Mascarenhas | |
| 6,251,639 B1 | 6/2001 | Kurn | |
| 6,630,160 B1 | 10/2003 | Evans et al. | |
| 6,692,918 B2 | 2/2004 | Kurn | |
| 6,861,406 B2 | 3/2005 | Mascarenhas | |
| 6,887,851 B2 | 5/2005 | Mascarenhas | |
| 6,914,049 B2 | 7/2005 | Mascarenhas | |
| 7,611,893 B2 | 11/2009 | Mascarenhas | |
| 7,618,816 B2 | 11/2009 | Mascarenhas | |
| 7,662,624 B2 * | 2/2010 | Mascarenhas | 435/320.1 |
| 2003/0161829 A1 | 8/2003 | Mascarenhas | |
| 2005/0245451 A1 | 11/2005 | Pincus | |
| 2006/0194271 A1 | 8/2006 | Sabatini et al. | |
| 2007/0072246 A1 | 3/2007 | Berg et al. | |
| 2007/0117819 A1 | 5/2007 | Rahbar et al. | |
| 2007/0128113 A1 | 6/2007 | Mascarenhas et al. | |
| 2008/0039393 A1 | 2/2008 | Mascarenhas | |
| 2009/0053203 A1 * | 2/2009 | Mascarenhas | 424/130.1 |
| 2010/0152113 A1 | 6/2010 | Mascarenhas | |
| 2011/0202281 A1 | 8/2011 | Mascarenhas | |
| 2012/0252722 A1 | 10/2012 | Mascarenhas | |

FOREIGN PATENT DOCUMENTS

| | | |
|---|---|---|
| WO | WO-2004/033481 A2 | 4/2004 |
| WO | WO-2004/033481 A3 | 4/2004 |
| WO | WO-2004/080405 A2 | 9/2004 |
| WO | WO-2004/080405 A3 | 9/2004 |
| WO | WO-2005/110493 A2 | 11/2005 |
| WO | WO-2005/110493 A8 | 11/2005 |
| WO | WO-2007/056511 A | 5/2007 |
| WO | WO-2007/056511 A2 | 5/2007 |
| WO | WO 2008/115525 * | 9/2008 |
| WO | WO 2009/117596 * | 9/2009 |

OTHER PUBLICATIONS

Ambrosini, G. et al. (Aug. 1997). "A Novel Anti-Apoptosis Gene, Survivin, Expressed in Cancer and Lymphoma," *Nature Medicine* 3(8):917-921.
Anderson, R.L. et al. (1981). "Temperature-Induced Homeoviscous Adaptation of Chinese Hamster Ovary Cells," *Biochimica et Biophysica Acta* 641:334-348.
Antman, K.H. et al. (Nov. 10, 1999). "High-Dose Chemotherapy for Breast Cancer," *JAMA* 282(18):1701-1703.
Aramburu, J. et al. (Sep. 24, 1999). "Affinity-Driven Peptide Selection of an NFAT Inhibitor More Selective Than Cyclosporin A," *Science* 285:2129-2133.
Arany, E. et al. (1996). "Rapid Clearance of Human Insulin-Like Growth Factor Binding Protein-3 From the Rat Circulation and Cellular Localization in Liver, Kidney and Stomach," *Growth Regulation* 6:32-41.
Armas, A. et al. (2006, e-pub. Jun. 13, 2006). "Zinc(II) Binds to the Neuroprotective Peptide Humanin," *Journal of Inorganic Biochemistry* 100:1672-1678.
Arteaga, E. et al. (Dec. 2005). "Plasma Amino-Terminal Pro-B-Type Natriuretic Peptide Quantification in Hypertrophic Cardiomyopathy," *American Heart Journal* 150(6):1228-1232.
Barile, G.R. et al. (Aug. 2005). "The RAGE Axis in Early Diabetic Retinopathy." *Investigative Ophthalmology & Visual Science* 46(8):2916-2924.
Barnes, J.A. et al. (2001). "Expression of Inducible Hsp70 Enhances the Proliferation of MCF-7 Breast Cancer Cells and Protects Against the Cytotoxic Effects of Hyperthermia," *Cell Stress Chaperones* 6(4):316-325.
Barsyte-Lovejoy, D. et al. (Mar. 22, 2002). "Specificity Determinants in MAPK Signaling to Transcription Factors," *The Journal of Biological Chemistry* 277(12):9896-9903.
Bart, J. et al. (2007, e-pub. Jul. 3, 2007). "Irradiation of Rat Brain Reduces P-Glycoprotein Expression and Function," *British Journal of Cancer* 97(3):322-326.
Benaki, D. et al. (2005). "Solution Structure of Humanin, a Peptide Against Alzheimer's Disease-Related Neurotoxicity," *Biochemical and Biophysical Research Communications* 329:152-160.
Benaki, D. et al. (2006, e-pub. Aug. 23, 2006). "Solution Structure of Ser14Gly-humanin, a Potent Rescue Factor Against Neuronal Cell Death in Alzheimer's Disease," *Biochemical and Biophysical Research Communications* 349:634-642.

(Continued)

Primary Examiner — Marianne P Allen
(74) Attorney, Agent, or Firm — Morrison & Foerster LLP

(57) ABSTRACT

The present invention is related to methods of generating adaptive biochemical signatures in live cells and the use of said signatures to identify diagnostic and therapeutic modalities for human disease. The methods described herein comprise contacting a provocative agent to live cells and measuring and analyzing adaptive readouts. The methods of the invention may be used for therapeutic or diagnostic purposes.

9 Claims, 24 Drawing Sheets

(56) References Cited

OTHER PUBLICATIONS

Bosio, A. et al (2002). "Kinetics of Gene Expression Profiling in Swiss 3T3 Cells Exposed to Aqueous Extracts of Cigarette Smoke," *Carcinogenesis* 23(5):741-748.

Butcher, J. (Feb. 2005). "Parkin Gene Therapy Could Treat Parkinson's Disease," *Lancet Neurol.* 4:82.

Butt, A.J. et al. (Jul. 2005). "Enhancement of Tumor Necrosis Factor-Alpha-Induced Growth Inhibition by Insulin-Like Growth Factor-Binding Proteins-5 (IGFBP-5), But Not IGFBP-3 in Human Breast Cancer Cells," *Endocrinology* 146(7):3113-3122.

Campisi, J. et al. (2003). "Stress-Induced Extracellular Hsp72 is a Functionally Significant Danger Signal to the Immune System," *Cell Stress & Chaperones* 8(3):272-286.

Cao, G. et al. (Jul. 1, 2002). "In Vivo Delivery of a Bcl-xL Fusion Protein Containing the TAT Protein Transduction Domain Protects Against Ischemic Brain Injury and Neuronal Apoptosis," *The Journal of Neuroscience* 22(13):5423-5431.

Cavasin, M.A. (May 2004). "Prolyl Oligopeptidase is Involved in Release of the Antifibrotic Peptide Ac-SDKP," *Hypertension* 43:1140-1145.

Cavasin, M.A. (2006). "Therapeutic Potential of Thymosin-β4 and its Derivative N-AcetylSeryl-Aspartyl-Lysyl-Proline (Ac-SDKP) in Cardiac Healing After Infarction," *Am. J. Cardiovasc. Drugs* 6(5):305-311.

Chiba, T. et al. (Nov. 2, 2005). "Development of a Femtomolar-Acting Humanin Derivative Named Colivelin by Attaching Activity-Dependent Neurotrophic Factor to Its N Terminus: Characterization of Colivelin-Mediated Neuroprotection Against Alzheimer's Disease-Relevant Insults in Vitro and in Vivo," *The Journal of Neuroscience* 25(44):10252-10261.

Chong, Y-P. et al. (Sep. 2005). "C-Terminal Src Kinase (CSK) and CSK-Homologous Kinase (CHK)—Endogenous Negative Regulators of Src-Family Protein Kinases," *Growth Factors* 23(3):233-244.

Ciocca, D.R. et al. (Oct. 6, 1993). "Biological and Clinical Implications of Heat Shock of Heat Shock Protein 27000 (Hsp27): a Review," *Journal of National Cancer Institute* 85(19):1558-1570.

Ciocca, D.R. et al. (2002). "Hsp27 as a Prognostic and Predictive Factor in Cancer," in *Small Stress Proteins*. A.-P. Arrigo et al. eds., Springer-Verlag Berlin Heidelberg, pp. 205-218.

Clemmons, D.R. et al. (Jan. 2005). "Interaction Between Insulin-Like Growth Factor-I Receptor and alphaVbeta3 Integrin Linked Signaling Pathways: Cellular Responses to Changes in Multiple Signaling Inputs," *Molecular Endocrinology* 19(1):1-11.

Cohen, M.P. et al. (2002). "Inhibiting Albumin Glycation in Vivo Ameliorates Glomerular Overexpression of TGF-β1," *Kidney International* 61:2025-2032.

Cohen, M.P. et al. (2005). "Evidence Linking Glycated Albumin to Altered Glomerular Nephrin and VEGFf Expression, Proteinuria, and Diabetic Nephropathy," *Kidney International* 68:1554-1561.

Copp, J. et al. (Mar. 1, 2009, e-pub. Feb. 24, 2009). "TORC-Specific Phosphorylation of Mammalian Target of Rapamycin (mTOR): Phospho-Ser$^{2481}$ is a Marker for Intact mTOR Signaling Complex 2," *Cancer Res.* 69(5):1821-1827.

Cornford, P.A. et al. (Dec. 15, 2000). "Heat Shock Protein Expression Independently Predicts Clinical Outcome in Prostate Cancer," *Cancer Research* 60:7099-7105.

Cruz, D.N. et al. (2010, e-pub. Dec. 3, 2009). "Plasma Neutrophil Gelatinase-Associated Lipocalin is an Early Biomarker for Acute Kidney Injury in an Adult ICU Population," *Intensive Care Med* 36:444-451.

Darios, F. et al. (2003). "Parkin Prevents Mitochondrial Swelling and Cytochrome C Release in Mitochondria-Dependent Cell Death," *Human Molecular Genetics* 12(5):517-526.

Davé, S.H. et al. (Dec. 1, 2007). "Amelioration of Chronic Murine Colitis by Peptide-Mediated Transduction of the IkB Kinase Inhibitor NEMO Binding Domain Peptide," *The Journal of Immunology* 179(1 1):7852-7859.

Dearth, R.K., et al (Dec. 2006). "Mammary Tumorigenesis and Metastasis Caused by Overexpression of Insulin Receptor Substrate 1 (IRS-1) or IRS-2," *Molecular and Cellular Biology* 26(24):9302-9314.

Dessein, P.H. et al. (2002). "Cardiovascular Risk in Rheumatoid Arthritis Versus Osteoarthritis: Acute Phase Response Related Decreased Insulin Sensitivity and High-Density Lipoprotein Cholesterol as Well as Clustering of Metabolic Syndrome Features in Rheumatoid Arthritis," *Arthritis Research* 4(5):1-6.

Driscoll, M. et al. (Mar. 2003). "Dying for a Cause: Invertebrate Genetics Takes on Human Neurodegeneration," *Nature Reviews Genetics* 4:181-194.

Escobar-Morreale, H.F. et al. (Feb. 2004). "Serum Interleukin-18 Concentrations are Increased in the Polycystic Ovary Syndrome: Relationship to Insulin Resistance and to Obesity," *The Journal of Clinical Endocrinology & Metabolism* 89(2):806-811.

Facchinetti, V. et al. (2008). "The Mammalian Target of Rapamysin Complex 2 Controls Folding and Stability of Akt and Protein Kinase C," *The EMBO Journal* 27(14):1932-1943.

Final Office Action mailed on Jun. 19, 2009, for U.S. Appl. No. 11/595,367, filed on Nov. 8, 2006, seven pages.

Firestein, G.S. (May 15, 2003). "Evolving Concepts of Rheumatoid Arthritis," *Nature* 423:356-361.

Garcia, B.A. et al. (Nov. 2003). "High-Sensitivity C-Reactive Protein in High-Grade Carotid Stenosis: Risk Marker for Unstable Carotid Plaque," *Journal of Vascular Surgery* 38(5):1018-1024.

Garcìa-Martìnez, J.M. et al. (2008). "mTOR Complex 2 (mTORC2) Controls Hydrophobic Motif Phosphorylation and Activation of Serum- and Glucocorticoid-Induced Protein Kinase 1 (SGK1)," *Biochem. Journal* 416:375-385.

Gargalovic, P. et al. (2003). "Cellular Apoptosis is Associated With Increased Caveolin-1 Expression in Macrophages," *Journal of Lipid Research* 44:1622-1632.

Gibson, S.L. et al. (Mar. 15, 2007). "Extra View. Divergent Roles for IRS-1 and IRS-2 in Breast Cancer Metastasis," *Cell Cycle.* 6(6):631-637.

Gobert, A.P. et al. (Jan. 2, 2004). "*Helicobacter Pylori* Heat Shock Protein 60 Mediates Interleukin-6 Production by Macrophages via a Toll-Like Receptor (TLR)-2-,TLR-4-, and Myeloid Differentiation Factor 88-Independent Mechanism," *The Journal of Biological Chemistry* 279(1):245-250.

Goldberg, M.S. et al. (Oct. 31, 2003). "Parkin-Deficient Mice Exhibit Nigrostriatal Deficits but Not Loss of Dopaminergic Neurons," *The Journal of Biological Chemistry* 278(44):43628-43635.

Goldin, A. et al. (2006). "Advanced Glycation End Products: Sparking the Development of Diabetic Vascular Injury," *Circulation* 114:597-605.

Gordon, M.S. et al. (2005). "Managing Patients Treated with Bevacizumab Combination Therapy," *Oncology* 69(Suppl 3):25-33.

Guertin, D.A. et al. (Feb. 3, 2009). "mTOR Complex 2 is Required for the Development of Prostate Cancer Induced by Pten Loss in Mice," *Cancer Cell* 15:148-159.

Guo, J. et al. (2008, e-pub. Oct. 15, 2008). "Nicotine Promotes Mammary Tumor Migration Via a Signaling Cascade Involving Protein Kinase C and cdc42," *Cancer Res.* 68(20):8473-8481.

Harkins, M.S. et al. (Dec. 2003). "Regulation of CD23 in the Chronic Inflammatory Response in Asthma: A Role for Interferon-γ and Heat-Shock Protein 70 in the $T_H2$ Environment," *Annals of Allergy Asthma & Immunology* 91:567-574.

Hayden, M.S. et al. (2004). "Signaling to NF-κb," *Genes and Development* 18:2195-2224.

Haywood, A.F.M. et al. (2004). "Parkin Counteracts Symptoms in a Drosophila Model of Parkinson's Disease," *BMC Neuroscience.* 5:1-12.

Hortobagyi, G.N. (Oct. 1, 1998). "Drug Therapy," *The New England Journal of Medicine* 339(14):974-984.

Humpert, P.M. et al. (Mar. 7, 2007). "Soluble RAGE but Not Endogenous Secretory RAGE is Associated with Albuminuria in Patients with Type 2 Diabetes," *Cardiovascular Diabetology* 6(9):1-5.

Huq, A. et al (2009). "The Metal-Binding Domain of IGFBP-3 Selectively Delivers Therapeutic Molecules Into Cancer Cells," *Anti-Cancer Drugs* 20(1):21-31.

Hussain, S. et al. (Jun. 1, 2009). "DUBs and Cancer. The Role of Deubiquitinating Enzymes As Oncogenes, Non-Oncogenes and Tumor Suppressors," *Cell Cycle* 8(11):1688-1697.

Ibrahim, Y.H. et al. (2008, e-pub. Sep. 25, 2008). "Progesterone Receptor-B Regulation of Insulin-Like Growth Factor—Stimulated Cell Migration in Breast Cancer Cells Via Insulin Receptor Substrate-2," *Mol. Cancer Res.* 6(9):1491-1498.

Ikonen, M. et al. (Oct. 28, 2003). "Interaction Between the Alzheimer's Survival Peptide Humanin and Insulin-Like Growth Factor-Binding Protein 3 Regulates Cell Survival and Apoptosis," *Proc. Nat. Acad. Sci.* 100(22):13042-13047.

International Preliminary Report on Patentability mailed on Oct. 1, 2009 for PCT Application No. PCT/US2008/003622, filed Mar. 19, 2008, five pages.

International Search Report mailed Nov. 29, 2007, for PCT Application No. PCT/US06/43622, filed Nov. 8, 2006, four pages.

Jacinto, E. (2007). "Phosphatase Targets in TOR Signaling," *Methods Mol. Biol.* 365:323-334. (Abstract Only).

Jacinto, E. (Aug. 2008). "Critical Review. What Controls TOR?" *IUBMB Life* 60(8)483-496.

Jackson, J.G. et al (2001). "Regulation of Breast Cancer Cell Motility by Insulin Receptor Substrate-2 (IRS-2) in Metastatic Variants of Human Breast Cancer Cell Lines," *Oncogene* 20:7318-7325.

Jensen, S.A. et al. (2006). "Risk Factors and Prevention of Cardiotoxicity Induced by 5-Flurouracil or Capecitabine," *Cancer Chemother. Pharmacol.* 58:487-493.

Jiang, H. et al. (2004). "Parkin Protects Human Dopaminergic Neuroblastoma Cells Against Dopamine-Induced Apoptosis," *Human Molecular Genetics* 13(16):1745-1754.

Johnstone, C.N. et al. (Mar. 2005). "*PRR5* Encodes a Conserved Proline-Rich Protein Predominant in Kidney: Analysis of Genomic Organization, Expression, and Mutation Status in Breast and Colorectal Carcinomas," *Genomics* 85(3):338-351.

Kaarniranta, K. et al. (2002). "Neuronal Cells Show Regulatory Differences in the hsp70 Gene Response," *Molecular Brain Research* 101:136-140.

Kanasaki, K. et al. (Apr. 2003). "N-Acetyl-Seryl-Aspartyl-Lysyl-Proline Inhibits TGF-β—Mediated Plasminogen Activator Inhibitor-1 Expression via Inhibition of Smad Pathway in Human Mesangial Cells," *Journal of American Society of Nephrology* 14(4):863-872.

Kiss, A.L. et al. (2002). "Caveolae and Caveolin Isoforms in Rat Peritoneal Macrophages," *Micron* 33:75-93.

Koya, D. et al. (Mar. 2000). "Amelioration of Accelerated Diabetic Mesangial Expansion by Treatment with a PKC β Inhibitor in Diabetic db/db Mice, a Rodent Model for Type 2 Diabetes," *The FASEB Journal* 14:439-447.

Koyama, H. et al. (Nov.-Dec. 2007). "RAGE and Soluble RAGE: Potential Therapeutic Targets for Cardiovascular Diseases," *Mol. Med.* 13(11-12):625-635.

Lee, J-W. et al. (Feb. 2004). "Hypoxia-Inducible Factor (HIF-1) Alpha: Its Protein Stability and Biological Functions," *Experimental and Molecular Medicine* 36(1):1-12.

Levi, I. et al. (2002). "Acute Myeloid Leukemia Associated with Nephrotic Syndrome: Case Report and Literature Review," *Leukemia & Lymphoma* 43(5):1133-1136.

Li, F. et al. (Dec. 1999). "Pleiotropic Cell-Division Defects and Apoptosis Induced by Interference With Survivin Function," *Nat Cell Biol.* 1(8):461-466.

Li, G.C. et al. (Dec. 1980). "A Proposed Operational Model of Thermotolerance Based on Effects of Nutrients and the Initial Treatment Temperature," *Cancer Res.* 40:4501-4508.

Lin, E.Y. et al. (2004). "Macrophages: Modulators of Breast Cancer Progression" in *Cancer and Inflammation Novartis Foundation Symposium 256*, John Wiley & Sons, Ltd., pp. 158-172.

Lin, Y-Z. et al. (Jun. 16, 1995). "Inhibition of Nuclear Translocation of Transcription Factor NF-κb by a Synthetic Peptide Containing a Cell Membrane-Permeable Motif and Nuclear Localization Sequence," *The Journal of Biological Chemistry* 270(24):14255-14258.

Ling, Y. et al. (Feb. 4, 2005). "DOK1 Mediates SHP-2 Binding to the aV83 Integrin and Thereby Regulates Insulin-Like Growth Factor I Signaling in Cultured Vascular Smooth Muscle Cells," *The Journal of Biological Chemistry* 280(5):3151-3158.

Lipton, A. (2005). "Bone Metastates in Breast Cancer," *Business Briefing: North American Pharmacotherapy* pp. 109-112.

Lo Bianco, C. et al. (Dec. 14, 2004). "Lentiviral Vector Delivery of Parkin Prevents Dopaminergic Degeneration in an Alpha-Synuclein Rat Model of Parkinson's Disease," *Proc. Natl. Acad. Sci. USA* 101 (50):17510-17515.

Logsdon, C.D. et al. (Dec. 2007). "RAGE and RAGE Ligands in Cancer," *Curr. Mol. Med.* 7(8):777-789. (Abstract Only).

Löwbeer, C. et al. (2004). "Serum Cardiac Troponin T in Patients Hospitalized with Heart Failure is Associated with Left Ventricular Hypertrophy and Systolic Dysfunction," *Scand. J. Clin. Lab Invest.* 64:667-676.

Luscher, B. et al. (1999). "The Basic Region/Helix-Loop-Helix/Leucine Zipper Domain of Myc Proto-Oncoproteins: Function and Regulation," *Oncogene* 18:2955-2966.

Ma, J. et al. (Apr. 7, 2004). "A Prospective Study of Plasma C-Peptide and Colorectal Cancer Risk in Men," *Journal of the National Cancer Institute* 96(7):546-553.

Malin, A. et al. (Feb. 15, 2004). "Evaluation of the Synergistic Effect of Insulin Resistance and Insulin-Like Growth Factors on the Risk of Breast Carcinoma," *Cancer* 100(4):694-700.

Martin, C.A. et al. (2003). "Aberrant Extracellular and Dendritic Cell (DC) Surface Expression of Heat Shock Protein (hsp)70 in the Rheumatoid Joint: Possible Mechanisms of hsp/DC-Mediated Cross-Priming," *The Journal of Immunology* 171:5736-5742.

Mascarenhas, D. et al. (2012, e-pub. Aug. 17, 2012). "Mammalian Target of Rapamycin Complex 2 Regulates Inflammatory Response to Stress," *Inflamm. Res.* ten pages.

Masri, J. et al. (Dec. 15, 2007, e-pub. Dec. 18, 2007). "mTORC2 Activity is Elevated in Gliomas and Promotes Growth and Cell Motility Via Overexpression of Rictor," *Cancer Res.* 67(24):11712-11720.

May, M.J. et al. (Sep. 1, 2000). "Selective Inhibition of NF-κb Activation by a Peptide That Blocks the Interaction of NEMO with the Iκb Kinase Complex," *Science* 289:1550-1554.

Michl, J. et al. (2006). "PNC-28, a p53-Derived Peptide That is Cytotoxic to Cancer Cells, Blocks Pancreatic Cancer Cell Growth in Vivo," *Int J Cancer.* 119:1557-1585.

Midgley, C.A. et al. (2000). "An N-Terminal p14$^{ARF}$ Peptide Blocks Mdm2-Dependent Ubiquitination in Vitro and can Activate p53 in Vivo," *Oncogene* 19:2312-2323.

Mitsiades, C.S. et al. (2006). "Proteasome Inhibition as a New Therapeutic Principle in Hematological Malignancies," *Current Drug Targets* 7(10):1341-1347.

Morley, J.F. et al. (Feb. 2004). "Regulation of Longevity in Caenorhabditis Elegans by Heat Shock Factor and Molecular Chaperones," *Molecular Biology of the Cell* 15:657-664.

Mulero, V. et al. (Oct. 1, 1999). "Regulation of Iron Metabolism in Murine J774 Macrophages: Rate of Nitric Oxide-Dependent and-Independent Pathways Following Activation With Gamma Interferon and Lipopolysaccharide," *Blood* 94(7):2383-2389.

Muqit, M.M.K. et al. (2004). "Parkin is Recruited into Aggresomes in a Stress-Specific Manner: Over-Expression of Parkin Reduces Aggresomes Formation but can be Disassociated From Parkin's Effect on Neuronal Survival," *Human Molecular Genetics* 13(1):117-135.

Nebbioso, A. et al. (Jan. 2005). "Tumor-Selective Action of HDAC Inhibitors Involves TRAIL Induction in Acute Myeloid Leukemia Cells," *Nature Medicine* 11(1):77-84.

Neeper, M. et al. (Jul. 25, 1992). "Cloning and Expression of a Cell Surface Receptor for Advanced Glycosylation End Products of Proteins," *The Journal of Biological Chemistry* 267(21):14998-15004.

Nishimoto, I. et al. (Mar. 2004). "Unravelling the Role of Humanin," *Trends Molecular Medicine* 10(3):102-105.

Nitta-Komatsubara, Y. et al. (2000). "Altered Ischemic Induction of Immediate Early Gene and Heat Shock Protein 70 mRNAs After Preconditioning in Rat Hearts," *Life Sciences* 66(13):1261-1270.

Njemini, R. et al. (2003). "Elevated Serum Heat-Shock Protein 70 Levels in Patients With Acute Infection: Use of an Optimized Enzyme-Linked Immunosorbent Assay," *Scandinavian Journal of Immunology* 58:664-669.

Noguchi, T. et al. (2003). "Lymph Node Metastasis Could be Predicted by Evaluation of Macrophage Infiltration and hsp70 Expression in Superficial Carcinoma of the Esophagus," *Oncology Reports* 10:1161-1164.

Nylandsted, J. et al. (2000). "Heat Shock Protein 70 is Required for the Survival of Cancer Cells" in *Annals of the New York Academy of Sciences Volume 926: Mechanisms of Cell Death II The Third Annual Conferences of the International Cell Death SOciety*, Z. Zakeri et al. eds., The New York Academy of Sciences, New York, New York, pp. 122-125.

Nylandsted, J. et al. (Dec. 15, 2002). "Eradication of Glioblastoma, and Breast and Colon Carcinoma Xenografts by Hsp70 Depletion," *Cancer Research* 62:7139-7142.

Oluwatosin-Chigbu, Y. et al. (2003). "Parkin Suppresses Wild-Type Alpha-SynucleinInduced Toxicity in SHSY-5Y Cells," *Biochemical and Biophysical Research Communications* 309:679-684.

Omata, M. et al. (2006). "N-Acetyl-Seryl-Aspartyl-Lysyl-Proline Ameliorates the Progression of Renal Dysfunction and Fibrosis in WKY Rats with Established Anti-Glomerular Basement Membrane Nephritis," *Journal of the American Society of Nephrology* 17:674-685.

Otani, M. et al. (2005). "Renal Involvement in Bone Marrow Transplantation," *Nephrology* 10:530-536.

Pearce, L.R. et al. (2007). "Identification of Protor as a Novel Rictor-Binding Component of mTOR Complex-2," *Biochem. J.* 405:513-522.

Peng, H. et al. (Feb. 2001). "Antifibrotic Effects of N-Acetyl-Seryl-Aspartyl-Lysyl-Proline on the Heart and Kidney in Aldosterone-Salt Hypertensive Rats," *Hypertension* 37(Part 2):794-800.

Perez, F.A. et al. (Feb. 8, 2005). "Parkin-Deficient Mice are not a Robust Model of Parkinsonism," *Proceedings of the National Academy of Sciences of the United States of America* 102(6):2174-2179.

Peterson, L.E. (2003). "Partitioning Large-Sample Microarray-Based Gene Expression Profiles using Principal Components Analysis," *Comput. Methods Programs Biomed.* 70:107-119.

Petropavlovaskaia, M. et al. (2006). "Development of an in Vitro Pancreatic Tissue Model to Study Regulation of Islet Neogenesis Associated Protein Expression," *Journal of Endocrinology* 191:65-81.

Picksley, S.M. et al. (1994). "Immunochemical Analysis of the Interaction of p53 with MDM2;—Fine Mapping of the MDM2 Binding Site on p53 Using Synthetic Peptides," *Oncogene* 9:2523-2529.

Pinton, P. et al. (Feb. 2, 2007). "Protein Kinase C β and Prolyl Isomerase 1 Regulate Mitochondrial Effects of the Life-Span Determinant $p66^{Shc}$," *Science* 315:659-663.

Pinton, P. et al. (Feb. 1, 2008). "p66Shc, Oxidative Stress and Aging: Importing a Lifespan Determinant Into Mitochondria," *Cell Cycle* 7(3):304-308.

Porrini, M. et al. (Aug. 2005). "Promises and Perils of Lycopene/Tomato Supplementation and Cancer Prevention: What are Typical Lycopene Intakes?" *The Journal of Nutrition* 135:2042S-2045S.

Purcell, A.W. et al. (2003). "Association of Stress Proteins With Autoantigens: A Possible Mechanism for Triggering Autoimmunity," *Clinical and Experimental Immunology* 132:193-200.

Rao, R.D. et al. (Oct. 2005). "Disruption of Parallel and Converging Signaling Pathways Contributes to the Synergistic Antitumor Effects of Simultaneous mTDR and EGFR Inhibition in GBM Cells," *Neoplastia* 7(10):921-929.

Rashmi, R. et al. (2004). "Ectopic Expression of Hsp70 Confers Resistance and Silencing its Expression Sensitizes Human Colon Cancer Cells to Curcumin-Induced Apoptosis," *Carcinogenesis* 25(2):179-187.

Rhaleb, N-E. et al. (Jun. 26, 2001). "Long-Term Effect of N-Acetyl-Seryl-Aspartyl-Lysyl-Proline on Left Ventricular Collagen Deposition in Rats with 2-Kidney, 1-Clip Hypertension," *Circulation* 103:3136-3141.

Ricaniadis, N. et al. (Feb. 2001). "Long-Term Prognostic Significance of HSP-70, C-Myc and HLA-DR Expression in Patients With Malignant Melanoma," *European Journal of Surgical Oncology* 27:88-93.

Roberts, A.B. et al. (2006). "Smad3 is Key to TGF-β-Mediated Epithelial-to-Mesenchymal Transition, Fibrosis, Tumor Suppression and Metastasis," *Cytokine & Growth Factor Reviews* 17:19-27.

Ron, D. et al. (Oct. 13, 1995). "C2 Region-Derived Peptides Inhibit Translocation and Function of β Protein Kinase C in Vivo," *The Journal of Biological Chemistry* 270(41):24180-24187.

Rosenberg, L. (1998). "Induction of Islet Cell Neogenesis in the Adult Pancreas: The Partial Duct Obstruction Model," *Microscopy Research and Technique* 43:337-346.

Sahoo, S. et al. (Nov. 2005, e-pub. Oct. 24, 2005). "Coordinate Expression of the PI3-Kinase Downstream Effectors Serum and Glucocorticoid-Induced Kinase (SGK-1) and Akt-1 in Human Breast Cancer," *Eur. J. Cancer* 41(17):2754-2759. (Abstract Only).

Saif, M.W. et al. (Jul. 2005). "Hemolytic-Uremic Syndrome Associated with Gemcitabine: A Case Report and Review of Literature," *Journal of Pancreas* 6(4):369-374.

Salomon, R. et al. (2000). "Genetics of the Nephrotic Syndrome," *Current Opinions in Pediatrics* 12:129-134.

Scharf, J-G. et al. (Apr. 1996). "Synthesis of Insulinlike Growth Factor Binding Proteins and of the Acid-Labile Subunit in Primary Cultures of Rat Hepatocytes, of Kupffer Cells, and in Cocultures: Regulation by Insulin, Insulinlike Growth Factor, and Growth Hormone," *Hepatology* 23(4):818-827.

Schenone, S. et al. (2007). "Last Findings on Dual Inhibitors and Abl and Src Tyrosine-Kinases," *Mini-Reviews in Medicinal Chemistry* 7(2):191-201.

Schiaffonati, L. et al. (1997). "Gene Expression in Liver After Toxic Injury: Analysis of Heat Shock Response and Oxidative Stress-Inducible Genes," *Liver*. 17:183-191.

Sharma, K. et al. (Jun. 2003). "Diabetic Kidney Disease in the db/db Mouse," *Am. J. Physiol. Renal Physiol.* 284:F1138-F1144.

Shibuya, K. et al. (Mar. 2005). "N-Acetyl-Seryl-Aspartyl-Lysyl-Proline Prevents Renal Insufficiency and Mesangial Matrix Expansion in Diabetic db/db Mice," *Diabetes* 54:838-845.

Singh, B. et al. (Jan. 2, 2004). "Insulin-Like Growth Factor-Independent Effects Mediated by a C-Terminal Metal-Binding Domain of Insulin-Like Growth Factor Binding Protein-3," *The Journal of Biological Chemistry* 279(1):477-487.

Singh, B.K. et al. (2008, e-pub. Jun. 20, 2008). "Bioactive Peptides Control Receptor for Advanced Glycated End Product-Induced Elevation of Kidney Insulin Receptor Substrate 2 and Reduced Albuminuria in Diabetic Mice," *Am. J. Nephrol.* 28:890-899.

Singh, B.K. et al. (2010). "A Nuclear Complex of Rictor and Insulin Receptor Substrate-2 is Associated with Albuminuria in Diabetic Mice," *Metabolic Syndrome and Related Disorder* 8(4):1-9.

Slattery, C. et al. (Aug. 2005). "Cyclosporine A-Induced Renal Fibrosis. A Role for Epithelial-Mesenchymal Transition," *American Journal of Pathology* 167(2):395-407.

Stohwasser, R. et al. (Jan. 2003). "Hepatitis B Virus HBx Peptide 116-138 and Proteasome Activator PA28 Compete for Binding to the Proteasome Alpha 4/MC6 Subunit," *Biol. Chem.* 384:39-49.

Strik, H.M. et al. (2000). "Heat Shock Protein Expression in Human Gliomas," *Anticancer Research* 20:4457-4462.

Strnad, J. et al. (2006). "NEMO Binding Domain of IKK-2 Encompasses Amino Acids 735-745," *Journal of Molecular Recognition* 19:227-233.

Sun, C. et al (2005). "Solution Structure of Human Survivin and Its Binding Interface With Smac/Diablo," *Biochemistry* 44(1):11-17.

Sun, L. et al. (Nov. 2010, e-pub. Aug. 25, 2010). "p66Shc Mediates High-Glucose and Angiotensin II-Induced Oxidative Stress Renal Tubular Injury Via Mitochondrial-Dependent Apoptotic Pathway," *Am. J. Physiol. Renal Physiol.* 299:F1014-F1025.

Szabo, S.J. et al. (Mar. 17, 2000). "A Novel Transcription Factor, T-Bet, Directs Th1 Lineage Commitment," *Cell* 100:655-669.

Tai, L-J. et al. (Jan. 4, 2002). "Structure-Function Analysis of the Heat Shock Factor-Binding Protein Reveals a Protein Composed Solely of a Highly Conserved and Dynamic Coiled-Coil Trimerization Domain," *The Journal of Biological Chemistry* 227(1):735-745.

Tajima, H. et al. (2005). "A Humanin Derivative, S14G-HN, Prevents Amyloid-β-Induced Memory Impairment in Mice," *Journal of Neuroscience Research* 79(5):714-723.

Takada, Y. et al. (Apr. 9, 2004). "Identification of a p65 Peptide That Selectively Inhibits NF-kB Activation Induced by Various Inflammatory Stimuli and Its Role in Down-Regulation of NF-kB-Mediated Gene Expression and Up-Regulation of Apoptosis," *The Journal of Biological Chemistry* 279(15):15096-15104.

Tan, A.L.Y. et al. (Mar. 2007). "AGE, RAGE, and ROS in Diabetic Nephropathy," *Semin. Nephrol.* 27(2):130-143.

Tas, S.W. et al. (2006, e-pub. May 9, 2006). "Local Treatment with the Selective Iκb Kinase β Inhibitor NEMO-Binding Domain Peptide Ameliorates Synovial Inflammation," *Arthritis Research & Therapy* 8:1-9.

Thedieck, K. et al. (Nov. 2007). "PRAS40 and PRR5-Like Protein are New mTOR Interactors that Regulate Apoptosis," *PLoS ONE* 2(11):e1217.

Tsilibary, E.C. et al. (Jul. 2003). "Microvascular Basement Membranes in Diabetes Mellitus," *J. Pathol.* 200(4):537-546.

Tuttle, K.R. et al. (Sep. 2003). "A Novel Potential Therapy for Diabetic Nephropathy and Vascular Complications: Protein Kinase C β Inhibition," *Am. J. Kidney Dis.* 42(3):456-465.

Uchida, Y. et al (Apr. 2010). "A Common Origin: Signaling Similarities in the Regulation of the Circadian Clock and DNA Damage Responses," *Biol. Pharm. Bull.* 33(4)535-544.

Valles, P. et al. (2003). "Heat Shock Proteins HSP27 and HSP70 in Unilateral Obstructed Kidneys," *Pediatr Nephrol* 18:527-535.

Vermolen, B.J. et al. (2008, e-pub. Jul. 18, 2008). "Segmentation and Analysis of the Three-Dimensional Redistribution of Nuclear Components in Human Mesenchymal Stem Cells," *Cytometry Part A.* 73A:816-824.

Volloch, V.Z. et al. (1999). "Oncogenic Potential of Hsp72," *Oncogene* 18:3648-3651.

Wang, G. et al. (2004). "Essential Requirement for Both hsf1 and hsf2 Transcriptional Activity in Spermatogenesis and Male Fertility," *Genesis* 38:66-80.

Wang, J-H. et al. (2002). "Blocking HSF1 by Dominant-Negative Mutant to Sensitize Tumor Cells to Hyperthermia," *Biochemical and Biophysical Research Communications* 290(5):1454-1461.

Wautier, J-L. et al. (Aug. 1994). "Advanced Glycation End Products (AGEs) on the Surface of Diabetic Erythrocytes Bind to the Vessel Wall via a Specific Receptor Inducing Oxidant Stress in the Vasculature: A Link Between Surface-Associated AGEs and Diabetic Complications," *Proc. Nat. Acad. Sci. USA* 91:7742-7746.

Weisberg, S.P. et al. (Dec. 2003). "Obesity is Associated With Macrophage Accumulation in Adipose Tissue," *The Journal of Clinical Investigation* 112(12):1796-1808.

Wendt, T. et al. (2006). "RAGE Modulates Vascular Inflammation and Atherosclerosis in a Murine Model of Type 2 Diabetes," *Atherosclerosis* 185:70-77.

Williams, M.E. (2006). "New Potential Agents in Treating Diabetic Kidney Disease," *Drugs* 66(18):2287-2298.

Wolf, G. et al. (2005). "p27$^{Kip1}$ Knockout Mice are Protected From Diabetic Nephropathy: Evidence for p27$^{Kip1}$ Haplotype Insufficiency," *Kidney International* 68:1583-1589.

Woo, S-Y. et al. (Aug. 31, 2007). "PRR5, a Novel Component of mTOR Complex 2, Regulates Platelet-derived Growth Factor Receptor 8 Expression and Signaling," *J. Biol. Chem.* 282(35):25604-25612.

Xu, H. et al. (Dec. 2003). "Chronic Inflammation in Fat Plays a Crucial Role in the Development of Obesity-Related Insulin Resistance," *The Journal of Clinical Investigation* 112(12):1821-1830.

Xu, X. et al. (Oct. 2006). "Humanin is a Novel Neuroprotective Agent Against Stroke," *Stroke* 37:2613-2619.

Yamada, M. et al (Feb. 2005). "Parkin Gene Therapy for Alpha-Synucleinopathy: A Rat Model of Parkinson's Disease," *Human Gene Therapy* 16:262-270.

Yamagishi, S. et al. (2006). "Advanced Glycation End Products (AGEs) and Their Receptor (RAGE) System in Diabetic Retinopathy," *Current Drug Discovery Technology* 3(1):83-88.

Yamagishi, S. et al. (Oct. 2007). "Kinetics, Role and Therapeutic Implications of Endogenous Soluble Form of Receptor for Advanced Glycation end Products (sRAGE) in Diabetes," *Curr. Drug Targets* 8(10):1138-1143.

Yamaoka, T. et al. (1999). "Development of Pancreatic Islets (Review)," *International Journal of Molecular Medicine* 3:247-261.

Yang, F. et al. (Feb. 2004). "Ac-SDKP Reverses Inflammation and Fibrosis in Rats with Heart Failure After Myocardial Infarction," *Hypertension* 43:229-236.

Yang, G. et al. (Mar. 15, 2004). "Reduced Infiltration of Class A Scavenger Receptor Positive Antigen-Presenting Cells Is Associated With Prostate Cancer Progression," *Cancer Research* 64:2076-2082.

Yang, Q. et al. (2006). "Identification of Sin1 as an Essential TORC2 Component Required for Complex Formation and Kinase Activity," *Genes and Development* 20:2820-2832.

Yano, T. (1999). "Activation of Extracellular Signal-Regulated Kinase in Lung Tissues of Mice Treated With Carcinogen," *Life Sciences* 64(4):229-236.

Yonekura, H. et al. (2005). "Roles of the Receptor for Advanced Glycation Endproducts in Diabetes-Induced Vascular Injury," *Journal of Pharmacological Science* 97:305-311.

Zager, R.A. et al. (2006). "Acute Renal Failure: Determinants and Characteristics of the Injury-Induced Hyperinflammatory Response," *Am J Physiol Renal Physiol* 291:F546-F556.

Zhang, R. et al. (2004). "Fluorescence Polarization Assay and Inhibitor Design for MDM2/p53 Interaction," *Analytical Biochemistry* 331:138-146.

Zhang, Y. et al. (1998). "Expression of Eukaryotic Proteins in Soluble Form in *Escherichia coli*," *Protein Expression and Purification* 12:159-165.

Zimmermann, E.M. et al. (2000). "Cell-Specific Localization of Insulin-Like Growth Factor Binding Protein mRNAs in Rat Liver," *Am J. Physiol. Gastrointest. Liver Physiol.* 278:G447-G457.

Zou, Y. et al. (Dec. 16, 2003). "Heat Shock Transcription Factor 1 Protects Cardiomyocytes From lschemia/Reperfusion Injury," *Circulation* 108:3024-3030.

\* cited by examiner

Figure 4A.

| | REGULON 1 | | REGULON 2 | | REGULON 3 | | REGULON 4 | REGULON 5 | | REGULON 6 | |
|---|---|---|---|---|---|---|---|---|---|---|---|
| | p-AKT-S473 | p-JNK | Body Weight | Glucose | Albuminuria | AKT1 | IRS2 | COL-IV | p-AKT-S308 | p-IRS1-S307 | INSULIN | p-PKCa/bII |
| p-AKT-S473 | | | | | | | | | | | | |
| p-JNK(T183/Y185) | 0.42 | | | | | | | | | | | |
| Body Weight | 0.37 | 0.43 | | | | | | | | | | |
| Glucose | 0.33 | 0.48 | 0.87 | | | | | | | | | |
| Albuminuria | 0.32 | 0.44 | 0.45 | 0.56 | | | | | | | | |
| AKT1 | | | -0.58 | -0.60 | -0.56 | | | | | | | |
| IRS-2 | | | | | -0.52 | -0.34 | | | | | | |
| COLLAGEN-IV | | | | | | -0.34 | 0.73 | | | | | |
| p-AKT-S308 | | | | | | | 0.52 | 0.35 | | | | |
| p-IRS1-S307 | 0.47 | | | | | | 0.36 | 0.37 | 0.62 | | | |
| INSULIN | | | | | | | | | | | | |
| p-PKCa/bII(T638/641) | | | | | | | | | | | 0.44 | |
| IRS1 | | | | | | | | | | | | 0.72 |

Figure 14. Effect of sub-cutaneously administered nephrilin in Dahl rats.
[A]
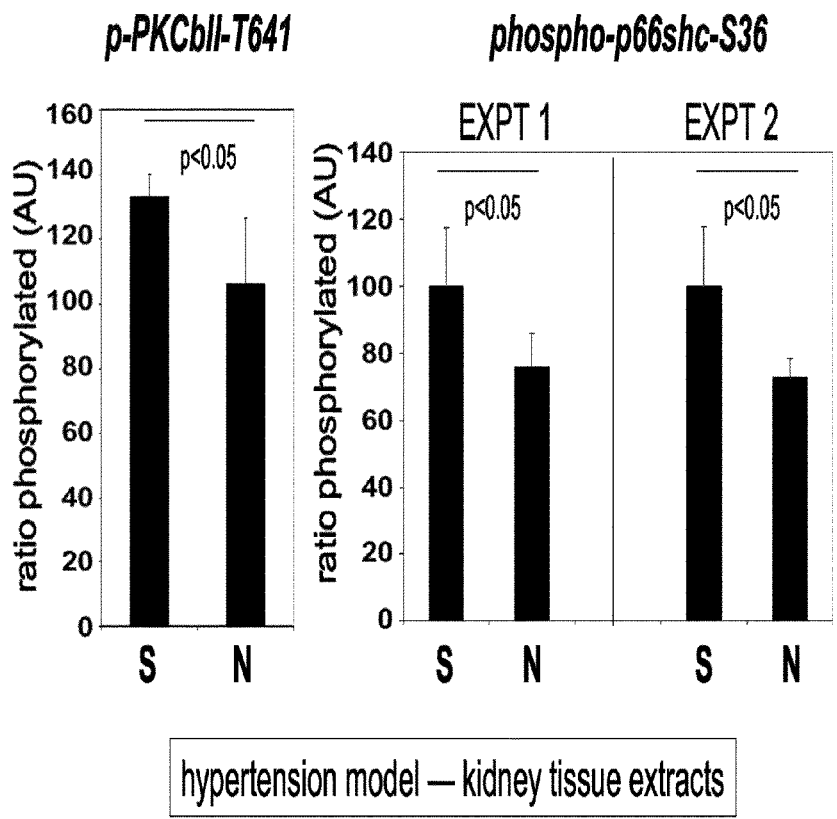

Figure 14 [B]
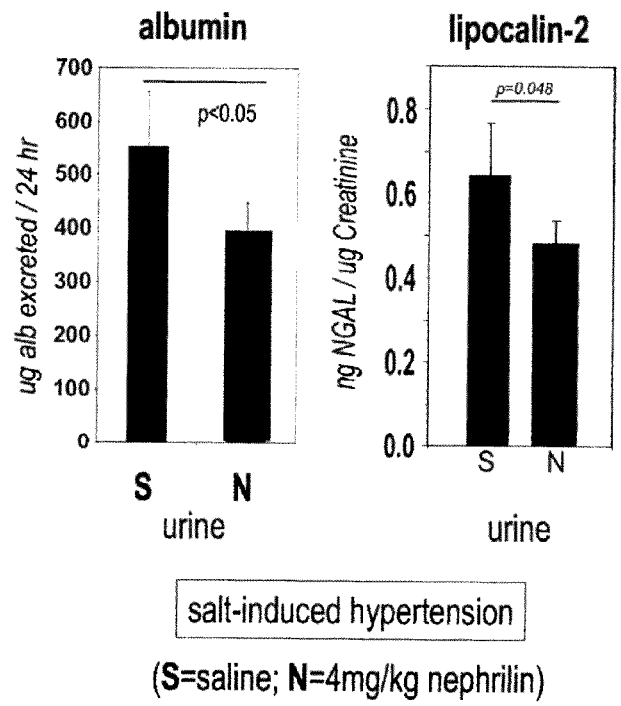

Figure 15. Effect of subcutaneously administered nephrilin in kidneys of Dahl rats.
[A]
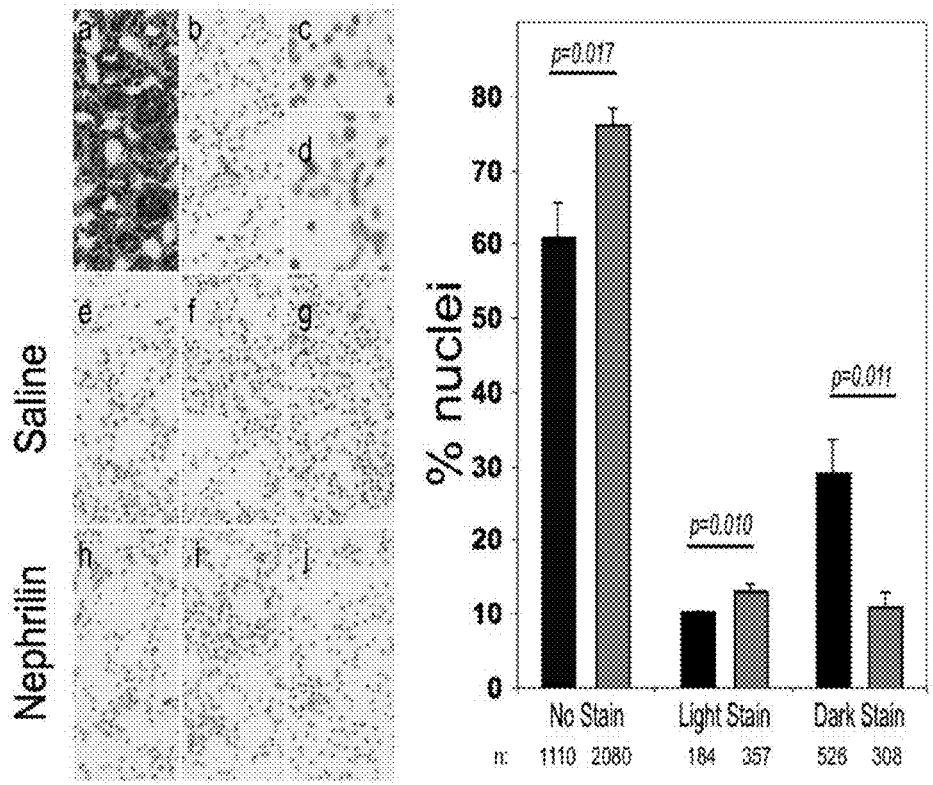

Figure 15 [B]
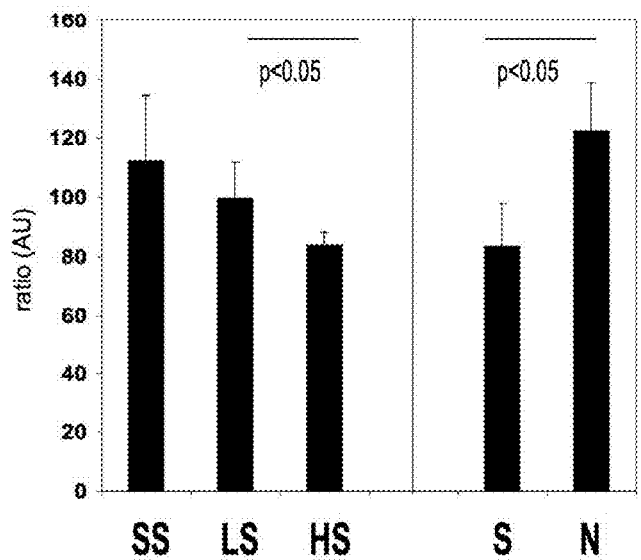

Figure 16. Effect of subcutaneously administered nephrilin in two models of AKI.
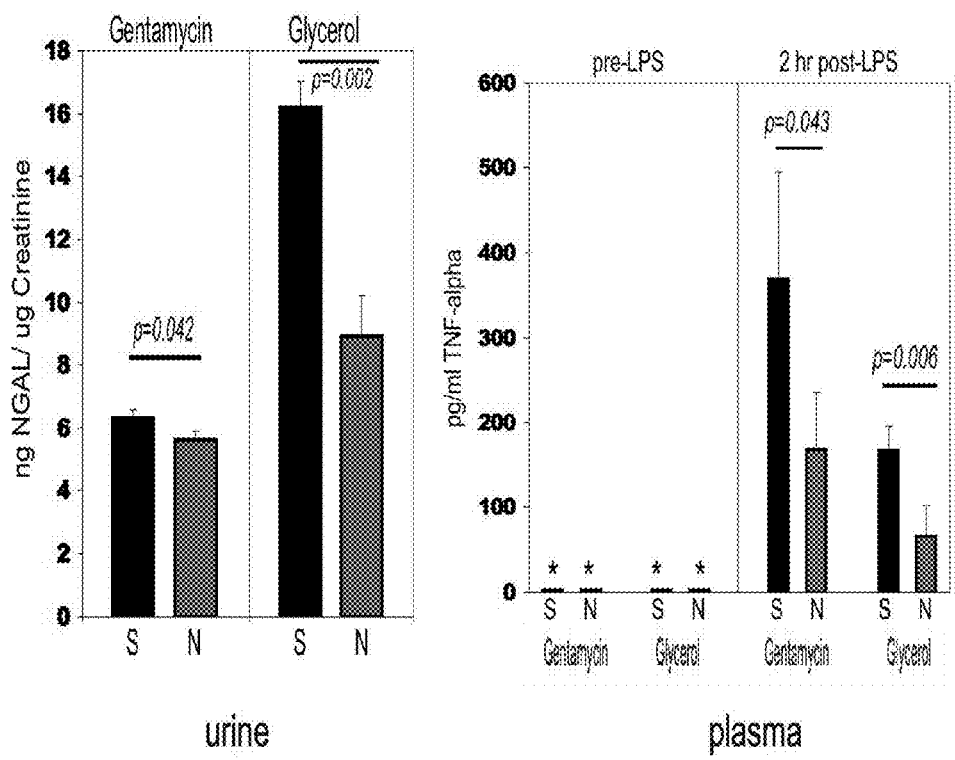

Figure 17 [A].

Gene Arrays: Pairwise Comparisons

MODEL / TISSUE

| | | | |
|---|---|---|---|
| Diabetes (db/db) | Kdn | 13wk db/wt vs. 13wk db/db | REG |
| Hypertension (Dahl) | Kdn | lo-salt diet vs hi-salt diet | REG |
| Hypertension (Dahl) | Kdn | hi-salt (saline) vs hi-salt (nephrilin) | COUNTER-REG |
| Rhabdomyolysis | Kdn | saline vs. glycerol | REG |
| Rhabdomyolysis | Hrt | saline vs. glycerol | REG |

| | DIABETES | HYPERTENSION |
|---|---|---|
| Total genetags | 25138 | 6204 (matching subset) |
| Significant signal | 10526 | 2103 |
| EMT: up-regulated | 73.3% | 48.3% |
| EMT: down-regulated | 25.0% | 48.8% |

EMT-related (common set, up-regulated)    11/16 genes (68.8%)

3 genes meeting criteria for disease-relatednedd and counter-regulation by mTORC2 inhibitor: UCHL1, PER2, B4galNT4

Figure 17 [B]
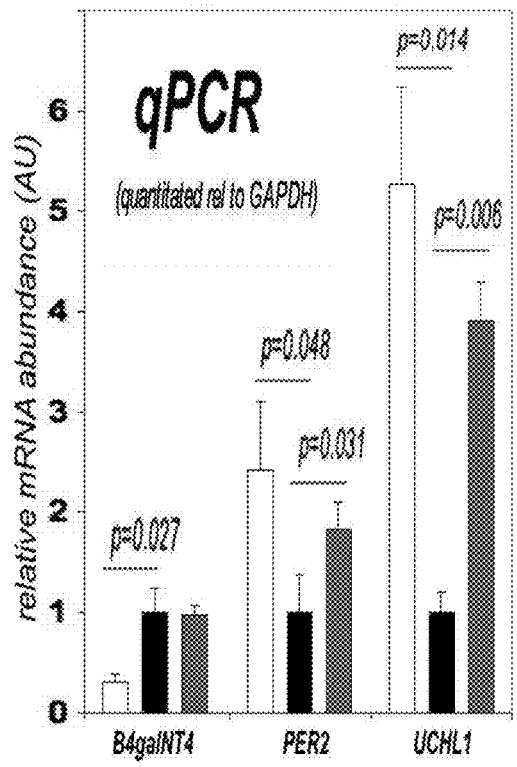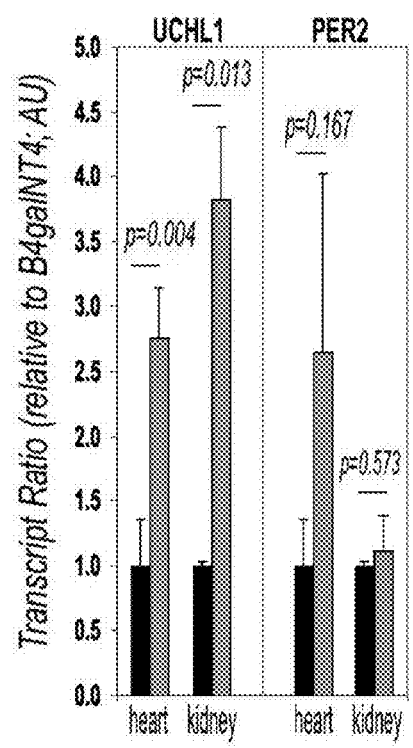

Figure 18. Effect of nephrilin treatment on metastasis.
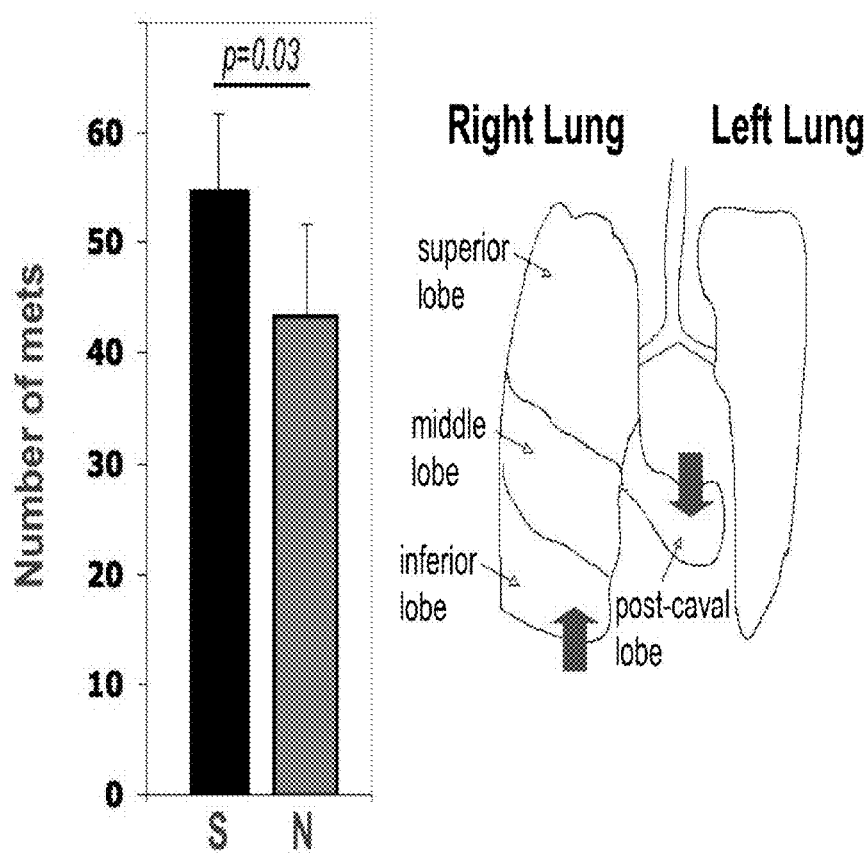

Figure 19. Reagents for screening candidate inhibitors and agonists of mTORC2 binding to its binding partners such as Protor/PRR5, Sin1, IRS1 or IRS2.
A. Map of reporter construct for mammalian cell line screening.
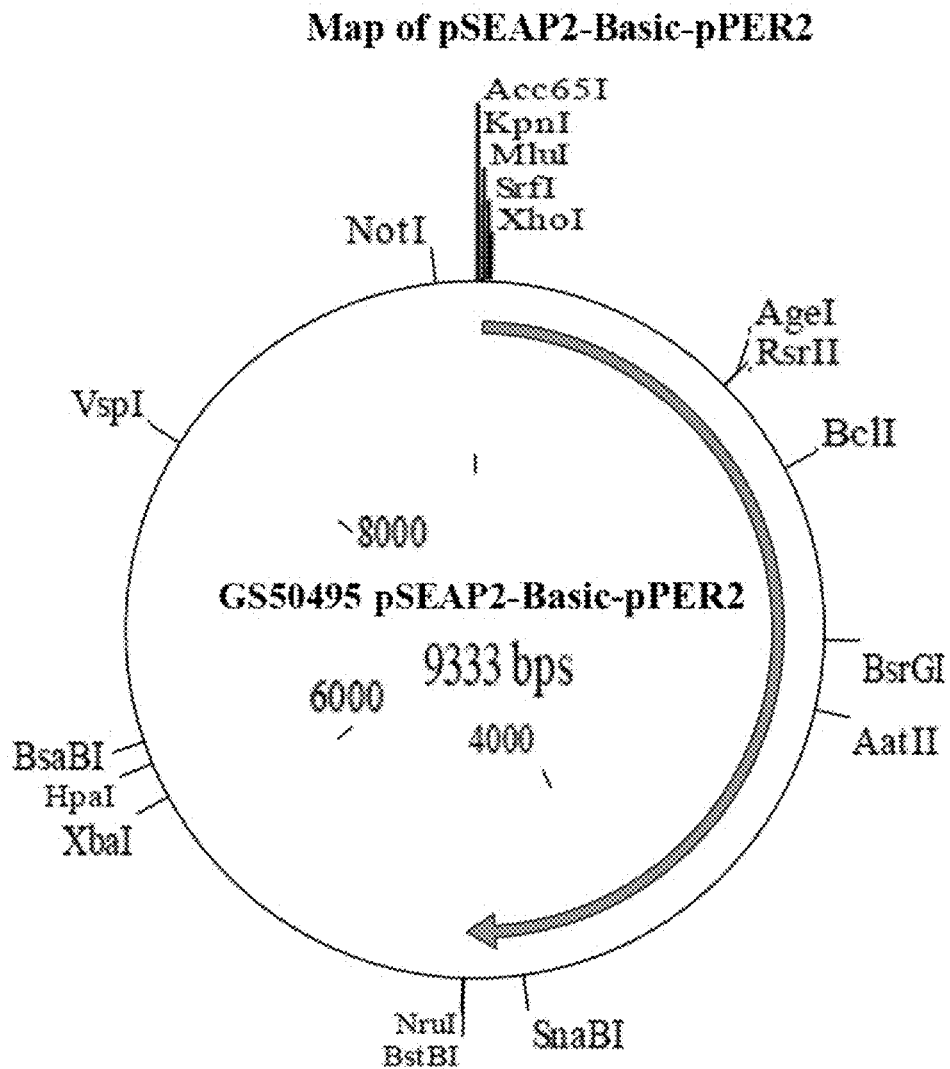
PCR amplified gene was cloned into HindIII/XhoI digested pSEAP2-Basic vector.

Figure 19 B

Predicted amino acid sequence of the RICT1 insert in pYZ85832.

```
GPKPYSLHLDHIIQKAIATHQKRDQYLRVQKDIFILKDTEEALLINLRDSQ
VLQHKENLEWNWNLIGTILKWPNVNLRNYKDEQLHRFVRRLLYFYKPSSKL
YANLDLDFAKAKQLTVVGCQFTEFLLESEEDGQGYLEDLVKDIVQWLNASS
GMKPERSLQNNGLLTTLSQHYFLFIGTLSCHPHGVKMLEKCSVFQCLLNLC
SLKNQDHLLKLTVSSLDYSRDGLARVILSKILTAATDACRLYATKHLRVLL
RANVEFFNNWGIELLVTQLHDKNKTISSEALDILDEACEDKANLHALIQMK
PALSHLGLNDIFEAQKIEWH
```

Figure 19 C

Expression of pRICT1 in BL21 cells at 33 degrees C.

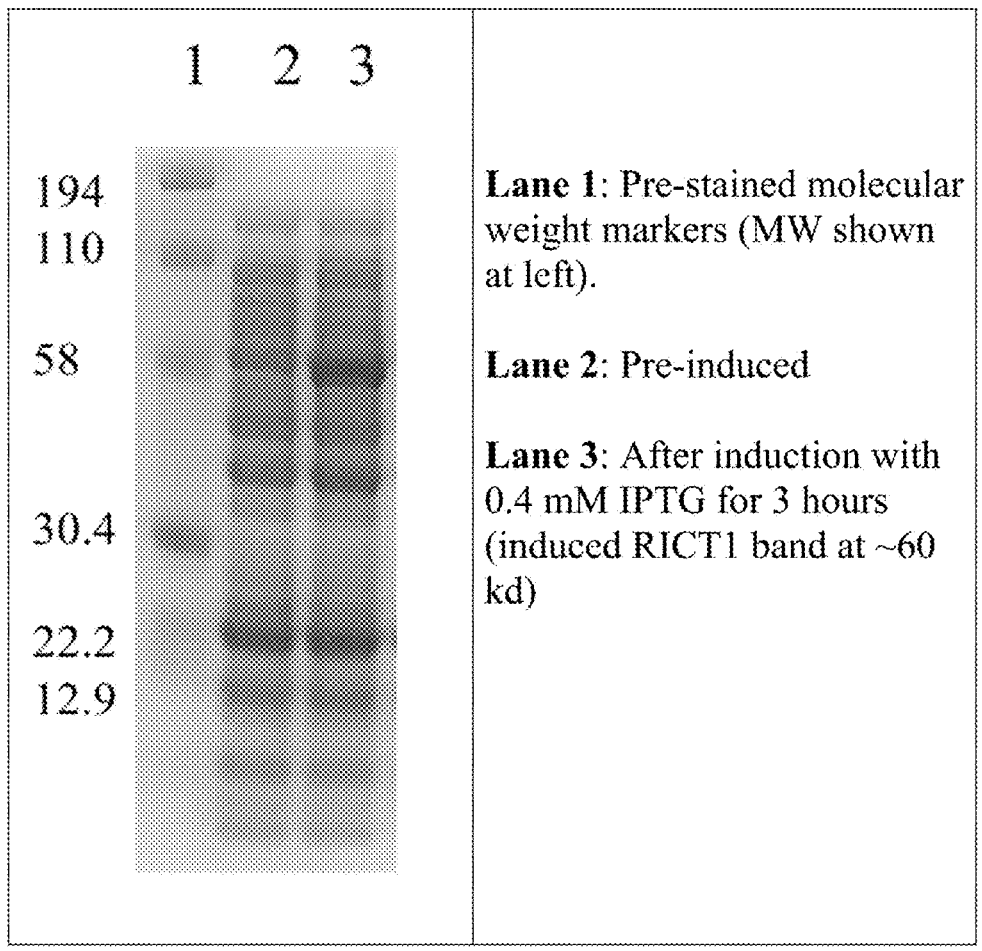

Lane 1: Pre-stained molecular weight markers (MW shown at left).

Lane 2: Pre-induced

Lane 3: After induction with 0.4 mM IPTG for 3 hours (induced RICT1 band at ~60 kd)

ADAPTIVE BIOCHEMICAL SIGNATURES

CROSS-REFERENCE TO RELATED APPLICATIONS

This application is a continuation-in-part of U.S. patent application Ser. No. 12/933,381, which was submitted under 35 U.S.C. §371 as a U.S. national stage application of International Application No. PCT/US09/37695, filed Mar. 19, 2009; International Application No. PCT/US09/37695 claims the benefit of U.S. Provisional Application Ser. No. 61/038,013, filed Mar. 19, 2008; U.S. Provisional Application Ser. No. 61/155,091, filed Feb. 24, 2009; and U.S. patent application Ser. No. 12/077,575, filed Mar. 19, 2008. Each application is hereby incorporated by reference in its entirety.

TECHNICAL FIELD

The invention relates to the field of medical diagnostics and therapeutics, and more particularly to methods for recognizing underlying mechanisms of disease and thereby identifying molecules that may be selectively active on human disease. The invention also relates to specific reagents and procedures of particular utility in the generation of therapeutic agents that regulate the binding of Rictor to its binding partners, thereby affecting the biochemical signatures characteristic of disease processes.

BACKGROUND ART

The so-called diseases of western civilization (chronic conditions such as arthritis, lupus, asthma, and other immune-mediated diseases, osteoporosis, atherosclerosis, other cardiovascular diseases, cancers of the breast, prostate and colon, metabolic syndrome-related conditions such as cardiovascular dysfunctions, diabetes and polycystic ovary syndrome (PCOS), neurodegenerative conditions such as Parkinson's and Alzheimer's, and ophthalmic diseases such as macular degeneration) are now increasingly being viewed as secondary to chronic inflammatory conditions which, in turn, may relate to oxidative stress. A correlation between oxidative stress and processes of aging may explain the rising incidence of these diseases as a direct consequence of an aging population. Lifestyle changes, such as increasingly sedentary habits resulting in the accumulation of fat, may also play a role in the rising significance of oxidative stress-proinflammatory states. A direct link between adiposity and inflammation has recently been demonstrated. Macrophages, potent donors of pro-inflammatory signals, are nominally responsible for this link: Obesity is marked by macrophage accumulation in adipose tissue (Weisberg S P et al [2003] *J. Clin Invest* 112: 1796-1808) and chronic inflammation in fat plays a crucial role in the development of obesity-related insulin resistance (Xu H, et al [2003] *J. Clin Invest.* 112: 1821-1830). Inflammatory cytokine IL-18 is associated with PCOS, insulin resistance and adiposity (Escobar-Morreale H F, et al [2004] *J. Clin Endo Metab* 89: 806-811). Systemic inflammatory markers such as CRP are associated with unstable carotid plaque, specifically, the presence of macrophages in plaque, which is associated with instability can lead to the development of an ischemic event (Alvarez Garcia B et al [2003] *J Vasc Surg* 38: 1018-1024). There are documented cross-relationships between these risk factors. For example, there is higher than normal cardiovascular risk in patients with rheumatoid arthritis (RA) (Dessein P H et al [2002] *Arthritis Res.* 4: R5) and elevated C-peptide (insulin resistance) is associated with increased risk of colorectal cancer (Ma J et al [2004] *J. Natl Cancer Inst* 96:546-553) and breast cancer (Malin A. et al [2004] *Cancer* 100: 694-700). The genesis of macrophage involvement with diseased tissues is not yet fully understood, though various theories postulating the "triggering" effect of some secondary challenge (such as viral infection) have been advanced. What is observed is vigorous crosstalk between macrophages, T-cells, and resident cell types at the sites of disease. For example, the direct relationship of macrophages to tumor progression has been documented. In many solid tumor types, the abundance of macrophages is correlated with prognosis (Lin E Y and Pollard J W [2004] *Novartis Found Symp* 256: 158-168). Reduced macrophage population levels are associated with prostate tumor progression (Yang G et al [2004] *Cancer Res* 64:2076-2082) and the "tumor-like behavior of rheumatoid synovium" has also been noted (Firestein G S [2003] *Nature* 423: 356-361). At sites of inflammation, macrophages elaborate cytokines such as interleukin-1-beta and interleukin-6.

A ubiquitous observation in chronic inflammatory stress is the up-regulation of heat shock proteins (HSP) at the site of inflammation, followed by macrophage infiltration, oxidative stress and the elaboration of cytokines leading to stimulation of growth of local cell types. For example, this has been observed with unilateral obstructed kidneys, where the sequence results in tubulointerstitial fibrosis and is related to increases in HSP70 in human patients (Valles, P. et al [2003] *Pediatr Nephrol.* 18: 527-535). HSP70 is required for the survival of cancer cells (Nylandsted J et al [2000] *Ann NY Acad Sci* 926: 122-125). Eradication of glioblastoma, breast and colon xenografts by HSP70 depletion has been demonstrated (Nylansted J et al [2002] *Cancer Res* 62:7139-7142; Rashmi R et al [2004] *Carcinogenesis* 25: 179-187) and blocking HSF1 by expressing a dominant-negative mutant suppresses growth of a breast cancer cell line (Wang J H et al [2002] *BBRC* 290: 1454-1461). It is hypothesized that stress-induced extracellular HSP72 promotes immune responses and host defense systems. In vitro, rat macrophages are stimulated by HSP72, elevating NO, TNF-alpha, IL-1-beta and IL-6 (Campisi J et al [2003] *Cell Stress Chaperones* 8: 272-86). Significantly higher levels of (presumably secreted) HSP70 were found in the sera of patients with acute infection compared to healthy subjects and these levels correlated with levels of IL-6, TNF-alpha, IL-10 (Njemini R et al [2003] *Scand. J. Immunol* 58: 664-669). HSP70 is postulated to maintain the inflammatory state in asthma by stimulating pro-inflammatory cytokine production from macrophages (Harkins M S et al [2003] *Ann Allergy Asthma Immunol* 91: 567-574). In esophageal carcinoma, lymph node metastasis is associated with reduction in both macrophage populations and HSP70 expression (Noguchi T. et al [2003] *Oncol.* 10: 1161-1164). HSPs are a possible trigger for autoimmunity (Purcell A W et al [2003] *Clin Exp Immunol.* 132: 193-200). There is aberrant extracellular expression of HSP70 in rheumatoid joints (Martin C A et al [2003] *J. Immunol* 171: 5736-5742). Even heterologous HSPs can modulate macrophage behavior: *H. pylori* HSP60 mediates IL-6 production by macrophages in chronically inflamed gastric tissues (Gobert A P et al [2004] *J. Biol. Chem* 279: 245-250).

In addition to immunological stress, a variety of environmental conditions can trigger cellular stress programs. For example, heat shock (thermal stress), anoxia, high osmotic conditions, hyperglycemia, nutritional stress, endoplasmic reticulum (ER) stress and oxidative stress each can generate cellular responses, often involving the induction of stress proteins such as HSP70.

One common feature of nearly all of the emerging diseases in the Western world is the complexity of the underlying biochemical dysfunctions. New methodology for identifying the core biochemical lesions in disease conditions is needed. Such methodology would provide a first step to the development of predictive diagnostics and adequately targeted interventions.

About 40,000 women die annually from metastatic breast cancer in the U.S. Current interventions focus on the use of chemotherapeutic and biological agents to treat disseminated disease, but these treatments almost invariably fail in time. At earlier stages of the disease, treatment is demonstrably more successful: systemic adjuvant therapy has been studied in more than 400 randomized clinical trials, and has proven to reduce rates of recurrence and death more than 15 years after treatment (Hortobagyi G N. (1998) *N Engl J Med.* 339 (14): 974-984). The same studies have shown that combinations of drugs are more effective than just one drug alone for breast cancer treatment. However, such treatments significantly lower the patient's quality of life, and have limited efficacy. Moreover, they may not address slow-replicating tumor reservoirs that could serve as the source of subsequent disease recurrence and metastasis. A successful approach to the treatment of recurrent metastatic disease must address the genetic heterogeneity of the diseased cell population by simultaneously targeting multiple mechanisms of the disease such as dysregulated growth rates and enhanced survival from (a) up-regulated stress-coping and anti-apoptotic mechanisms, and (b) dispersion to sequestered and privileged sites such as spleen and bone marrow. Cellular diversification, which leads to metastasis, produces both rapid and slow growing cells. Slow-growing disseminated cancer cells may differ from normal cells in that they are located outside their 'normal' tissue context and may up-regulate both anti-apoptotic and stress-coping survival mechanisms. Global comparison of cancer cells to their normal counterparts reveals underlying distinctions in system logic. Cancer cells display up-regulated stress-coping and anti-apoptotic mechanisms (e.g. NF-kappa-B, Hsp-70, MDM2, survivin etc.) to successfully evade cell death (Chong Y P, et al. (2005) *Growth Factors*. September; 23 (3): 233-44; Rao R D, et al (2005) *Neoplasia*. October; 7 (10): 921-9; Nebbioso A, et al (2005) *Nat Med*. January; 11 (1): 77-84). Many tumor types contain high concentrations of heat-shock proteins (HSP) of the HSP27, HSP70, and HSP90 families compared with adjacent normal tissues (Ciocca at al 1993; Yano et al 1999; Cornford at al 2000; Strik et al 2000; Ricaniadis et al 2001; Ciocca and Vargas-Roig 2002). The role of HSPs in tumor development may be related to their function in the development of tolerance to stress (Li and Hahn 1981) and high levels of HSP expression seem to be a factor in tumor pathogenesis. Among other mechanisms individual HSPs can block pathways of apoptosis (Volloch and Sherman 1999). Studies show HSP70 is required for the survival of cancer cells (Nylandsted J, Brand K, Jaattela M. (2000) *Ann NY Acad Sci*. 926: 122-125). Eradication of glioblastoma, breast and colon xenografts by HSP70 depletion has been demonstrated, but the same treatment had no effect on the survival or growth of fetal fibroblasts or non-tumorigenic epithelial cells of breast (Nylandsted J, et al (2002) *Cancer Res*. 62 (24): 7139-7142; Rashmi R, Kumar S, Karunagaran D. (2004) *Carcinogenesis*. 25 (2): 179-187; Barnes J A, et al. (2001) *Cell Stress Chaperones*. 6 (4): 316-325) and blocking HSF1 by expressing a dominant-negative mutant suppresses growth of a breast cancer cell line (Wang J H, et al. (2002) *Biochem Biophys Res Commun*. 290 (5): 1454-1461). Stress can also activate the nuclear factor kappa B (NF-kappa B) transcription factor family. NF-kappa-B is a central regulator of the inflammation response that regulates the expression of anti-apoptotic genes, such as cyclooxygenases (COX) and metalloproteinases (MMPs), thereby favoring tumor cell proliferation and dissemination. NF-kappa-B can be successfully inhibited by peptides interfering with its intracellular transport and/or stability (Butt A J, et al. (2005) *Endocrinology*. July; 146 (7): 3113-22). Human survivin, an inhibitor of apoptosis, is highly expressed in various tumors (Ambrosini G, Adida C, Altieri D C. (1997) *Nat. Med*. 3 (8): 917-921) aberrantly prolonging cell viability and contributing to cancer. It has been shown that ectopic expression of survivin can protect cells against apoptosis (Li F, et al. (1999) *Nat. Cell Biol*. 1 (8): 461-466). Tumor suppressor p53 is a transcription factor that induces growth arrest and/or apoptosis in response to cellular stress. Peptides modeled on the MDM2-binding pocket of p53 can inhibit the negative feedback of MDM2 on p53 commonly observed in cancer cells (Midgley C A, et al. (2000) *Oncogene*. May 4; 19 (19): 2312-23; Zhang R, et al. (2004) *Anal Biochem*. August 1; 331 (1): 138-46). The role of protein degradation rates and the proteasome in disease has recently come to light Inhibitors of HSP90 (a key component of protein degradation complexes) such as bortezomib are in clinical testing and show promise as cancer therapeutics (Mitsiades C S, et al. 2006 *Curr Drug Targets*. 7(10):1341-1347). A C-terminal metal-binding domain (MBD) of insulin-like growth factor binding protein-3 (IGFBP-3) can rapidly (<10 min) mobilize large proteins from the extracellular milieu into the nuclei of target cells (Singh B K, et al. (2004) *J Biol Chem*. 279: 477-487). Here we extend these observations to show that MBD is a systemic 'guidance system' that attaches to the surface of red blood cells and can mediate rapid intracellular transport of its 'payload' into the cytoplasm and nucleus of target cells at privileged sites such as spleen and bone marrow in vivo. The amino acid sequence of these MBD peptides can be extended to include domains known to inhibit HSP, survivin, NF-kappa-B, proteasome and other intracellular mechanisms. The MBD mediates transport to privileged tissues and intracellular locations (such as the nucleus) in the target tissue. In this study we ask whether such MBD-tagged peptides might act as biological modifiers to selectively enhance the efficacy of existing treatment modalities against cancer cells. Patients presenting with metastatic disease generally face a poor prognosis. The median survival from the time of initial diagnosis of bone metastasis is 2 years with only 20% surviving 5 years (Antman et al. (1999) *JAMA.;* 282: 1701-1703; Lipton A. (2005) *North American Pharmacotherapy:* 109-112). A successful systemic treatment for recurrent metastatic disease is the primary unmet medical need in cancer.

Part of the lack of success in treating metastatic disease may have to do with a lack of understanding of the metastatic disease process. Unlike the primary tumor event, which is primarily a dysfunction of unregulated growth, metastatic cells must generally adapt to unusual environments in body locations that are distant to the original tumor site. Thus, most traditional interventions designed to treat a primary tumor, which focus on controlling tumor cell growth, may be fundamentally unsuited to the treatment of metastatic disease, which is a disease of adaptation. Thus there is a need for identifying the biochemical correlates of cellular adaptivity.

Diabetes is a rapidly expanding epidemic in industrial societies. The disease is caused by the body's progressive inability to manage glucose metabolism appropriately. Insulin production by pancreatic islet cells is a highly regulated process that is essential for the body's management of carbohydrate metabolism. The primary economic and social damage of diabetes is from secondary complications that arise in the body after prolonged exposure to elevated blood sugar. These include cardiovascular complications, kidney disease and retinopathies. Most interventions so far developed for diabetic conditions focus on controlling blood sugar, the primary cause of subsequent complications. However, despite the availability of several agents for glycemic control, the population of individuals with poorly controlled blood sugar continues to explode. 40% of kidney failure is currently associated with diabetes, and that percentage is expected to rise.

One potential approach to treating the complications of diabetes is to focus on the cellular biochemistry of organs that are particularly sensitive to elevated blood sugar levels. Advanced glycosylation end products of proteins (AGEs) are non-enzymatically glycosylated proteins which accumulate in vascular tissue in aging and at an accelerated rate in diabetes. Cellular actions of advanced glycation end-products (AGE) are mediated by a receptor for AGE (RAGE), a novel integral membrane protein (Neeper M et al [1992] *J. Biol. Chem.* 267: 14998-15004). Receptor for AGE (RAGE) is a member of the immunoglobulin superfamily that engages distinct classes of ligands. The bioactivity of RAGE is governed by the settings in which these ligands accumulate, such as diabetes, inflammation and tumors. Vascular complications of diabetes such as nephropathy, cardiomyopathy and retinopathy, may be driven in part by the AGE-RAGE system (Wautier J-L, et al [1994] *Proc. Nat. Acad. Sci.* 91: 7742-7746; Barile G R et al [2005] *Invest. Ophthalm. Vis. Sci.* 46: 2916-2924; Yonekura H et al [2005] *J. Pharmacol. Sci.* 97: 305-311). Specific downstream cellular molecular events are now believed to mediate some of the damaging consequences of RAGE activation, and generate a rationale for chemical, biological and genetic interventions in these types of hypertrophic disease processes (Cohen M P et al [2005] *Kidney Int.* 68: 1554-1561; Cohen M P et al [2002] *Kidney Int.* 61: 2025-2032; Wendt T et al [2006] *Atherosclerosis* 185: 70-77; Wolf G et al [2005] *Kidney Int.* 68: 1583-1589). Soluble RAGE is associated with albuminuria in human diabetics (Humpert P M et al [2007] *Cardiovasc. Diabetol.* 6: 9) and in animal models of diabetic nephropathy such as the db/db mouse (Yamagishi S et al [2006] *Curr. Drug Discov. Technol.* 3: 83-88; Sharma K et al [2003] *Am J. Physiol. Renal Physiol.* 284: F1138-F1144). In the complex disease process of diabetic progression the causal interplay of hypertensive, glycemic, inflammatory and endocrinological factors is difficult to parse. Nevertheless, magnetic resonance imaging of the db/db mouse reveals progressive cardiomyopathic changes as diabetes progresses. Relatively early in the disease process (9 weeks), left ventricular hypertrophy (LVH) is observed. In human populations, LVH correlates with elevated levels of NT-pro-BNP and cardiac Troponin T (cTnT) in serum (Arteaga E et al [2005] *Am Heart J.* 150: 1228-1232; Lowbeer C et al [2004] *Scand J. Clin. Lab Invest.* 64: 667-676).

TOR (target of rapamycin) proteins are conserved Ser/Thr kinases found in diverse eukaryotes ranging from yeast to mammals. The TOR kinase is found in two biochemically and functionally distinct complexes, termed TORC1 and TORC2. mTORC1 contains mTOR phosphorylated predominantly on S2448, whereas mTORC2 contains mTOR phosphorylated predominantly on S2481 (Copp J et al [2009] *Cancer Res.* 69: 1821-1827). Aided by the compound rapamycin, which specifically inhibits TORC1, the role of TORC1 in regulating translation and cellular growth has been extensively studied. mTORC2 is rapamycin insensitive and seems to function upstream of Rho GTPases to regulate the actin cytoskeleton (Jacinto E, et al [2004] *Nat Cell Biol.* 6: 1122-1128). The physiological roles of TORC2 have remained largely elusive due to the lack of pharmacological inhibitors and its genetic lethality in mammals. PRR5 and related proteins are a new class of molecules found in association to mTORC2 complex, and may be required cofactors for the function of this central regulator of cellular biochemistry. The PRR5 gene encodes a conserved proline-rich protein predominant in kidney (Johnstone C N et al [2005] *Genomics* 85: 338-351). The PRR5 class of proteins is believed to physically associate with mTORC2 and regulate aspects of growth factor signaling and apoptosis (Woo S Y et al [2007] *J. Biol. Chem.* 282: 25604-25612; Pearce L R et al [2007] *Biochem J.* 405: 513-522; Thedieck K et al [2007] *PLoS ONE* 2: e1217). In this invention, the importance of a particular domain within PRR5 (referred to as the PRR5D sequence) comprising the sequence HESRGVTEDYLRLETLVQKVVSPYLGTYGL (SEQ ID NO:3) is demonstrated. This sequence is conserved in human PRR5 isoforms and PRR5L as well as in rat and mouse. Other obligate partners of Rictor, a central defining protein component of the mTORC2 complex, include Sin1 (also known as MIP1). Sin1 is an essential component of TORC2 but not of TORC1, and functions similarly to Rictor, the defining member of TORC2, in complex formation and kinase activity. Knockdown of Sin1 decreases Akt phosphorylation in both *Drosophila* and mammalian cells and diminishes Akt function in vivo. It also disrupts the interaction between Rictor and mTOR. Furthermore, Sin1 is required for TORC2 kinase activity in vitro (Yang Q et al [2006] *Genes Dev.* 20: 2820-2832). mTOR, SIN1 and Rictor, components of mammalian (m)TORC2, are required for phosphorylation of Akt, SGK1 (serum- and glucocorticoid-induced protein kinase 1), and conventional protein kinase C (PKC) at the turn motif (TM) site. This TORC2 function is growth factor independent and conserved from yeast to mammals. TM site phosphorylation facilitates carboxyl-terminal folding and stabilizes newly synthesized Akt and PKC by interacting with conserved basic residues in the kinase domain Without TM site phosphorylation, Akt becomes protected by the molecular chaperone Hsp90 from ubiquitination-mediated proteasome degradation (Facchinetti V et al [2008] *EMBO J.* 27: 1932-1943; García-Martínez J M and Alessi D R [2008] *Biochem J.* 416: 375-385; Jacinto E and Lorberg A. [2008] *Biochem J.* 410:19-37).

mTORC2 activity was elevated in glioma cell lines as well as in primary tumor cells as compared with normal brain tissue (Masri J et al [2007] *Cancer Res.* 67: 11712-11720). In these lines Rictor protein and mRNA levels were also elevated and correlated with increased mTORC2 activity. Protein kinase C alpha (PKC alpha) activity was shown to be elevated in rictor-overexpressing lines but reduced in rictor-knockdown clones, consistent with the known regulation of actin organization by mTORC2 via PKC alpha. Xenograft studies using these cell lines also supported a role for increased mTORC2 activity in tumorigenesis and enhanced tumor growth. These data suggest that mTORC2 is hyperactivated in gliomas and functions in promoting tumor cell proliferation and invasive potential. mTORC2 and its activation of downstream AGC kinases such as PKC-alpha, SGK1 and Akt have also been implicated in cancers of the prostate and breast (Guertin D A et al [2009] *Cancer Cell.* 15: 148-159; Sahoo S et al [2005] *Eur J Cancer.* 41: 2754-2759; Guo J, et al [2008] *Cancer Res.* 68: 8473-8481).

IRS-1 and IRS-2 are master traffic regulators in intracellular signal transduction pathways associated with growth and metabolism, playing key roles in the docking of accessory proteins to phosphorylated insulin and IGF receptors. Although similar in function, activated IRS-1 and IRS-2 proteins generate subtly different cellular outcomes, at least in part through the phosphorylation of different Akt (especially Akt 1 and Akt 2) and MAP kinase isoforms.

The significance of IRS-2 to IRS-1 ratios in inflammatory disease processes has never been explicitly cited. The possibility of using specific modulators of the IRS-2:IRS-1 to intervene in such disease processes has not been explicitly proposed. Such modulators might include, for example, treatments or compounds that preferentially reduce IRS-2 (versus IRS-1) signaling, or preferentially increase IRS-1 (versus IRS-2) signaling. Some unrelated observations of potential significance here are the use of a KRLB domain-specific inhibitor for IRS-2, the use of selected HIV protease inhibitors such as nelfinavir, saquinavir and ritonavir (previously shown to selectively inhibit IRS-2 over IRS-1). In this invention, the modulating effects of certain peptides such as humanin, PRR5 domain (PRR5D), and NPKC on IRS-2 versus IRS-1, both in vitro and in vivo, are described. The specific induction of IRS-2 in human kidney cells by a ligand of RAGE, first demonstrated here, and the modulation of that induction by humanin and NPKC peptides, further suggests the involvement of similar mechanisms of pathology in other RAGE-related proliferative or inflammatory conditions such as metastatic breast cancer, Alzheimer's disease, atherosclerosis, other cardiovascular conditions, arthritis, other autoimmune conditions and sepsis. Also shown here for the first time is the direct correlation between kidney IRS-2 levels, kidney collagen-IV levels and kidney function in diabetic db/db mice. Other peptides may also modulate IRS-2:IRS-1 ratios, including but not limited to MBD-KRLB (SEQ ID NO:3).

IRS-1 and IRS-2 are expressed in normal mammary epithelial cells and in breast carcinoma cells, where they have been implicated in mediating signals to promote tumor cell survival, growth and motility. Although IRS-1 and IRS-2 are homologous, some recent studies have revealed distinct functions for these adaptor proteins in regulating breast cancer progression. Specifically, IRS-2 is a positive regulator of metastasis, whereas IRS-1 may be a suppressor of metastasis and cell motility (Gibson S L et al [2007] Cell Cycle. 6: 631-637; Jackson J G et al [2001] Oncogene. 20: 7318-7325; Ibrahim Y H et al [2008] Mol Cancer Res. 6: 1491-1498). Other studies suggest that both IRS-1 and IRS-2 can promote metastasis (Dearth R K, et al [2006] Mol Cell Biol. 26: 9302-9314).

We have recently shown (Singh B K and Mascarenhas D D [2008] Am J Nephrol. 28: 890-899) that wild type humanin and other peptides can reduce albuminuria in db/db mice. The accompanying biochemical changes in mouse kidney tissue, as well as in cell culture systems using human kidney cells stimulated with glycated hemoglobin, suggest a tight correlation of albuminuria with elevated IRS-2 levels, higher PKC-alpha/beta phosphorylation and changes in Akt status. We now show that SGK1 is also elevated in diabetic kidneys. Upon treatment with humanin and related peptides, the perturbations in these markers are simultaneously ameliorated. Moreover, we show here for the first time that treatment with nephrilin, a peptide designed to compete with the PRR5-Rictor interface, also reduced albuminuria, phospho-PKC, IRS-2 and SGK1 in diabetic kidneys. The RAGE system has been implicated in cancer and metastasis (Logsdon C D et al [2007] Curr Mol Med. 7: 777-789). In our ELISA assays of extracts prepared from paired cell lines (each pair from a single patient) we have demonstrated for the first time that primary tumor cells differed from metastatic variants by virtue of the metastatic variants (but not the primary tumor cells) being able to dramatically enhance levels of IRS-2, phospho-PKC-alpha/beta and Akt status in response to glycated hemoglobin (RAGE ligand) stimulus. We also showed that breast cancer cells that successfully set up liver metastasis in mice have significantly elevated IRS2:IRS1 ratios compared to the original cultured human cancer cell line used in the experiment. Taken together with the observation made here for the first time that there is a physical association between Rictor and IRS proteins in kidney cells, and that this association is significantly reduced by treatment with nephrilin peptide (which reduces albuminuria in db/db mice) we propose a fundamentally new insight into the mechanism of key disease processes such as diabetes and cancer metastasis, and diseases involving a systemic inflammatory component. We further propose new intervention strategies for treating these disease processes. Specifically, we propose criteria for recognizing a global, disease-associated cellular biochemical signature characterized by distinctively altered (a) isotype levels, cellular location and phosphorylation status of IRS proteins (b) ratios of active mTORC2 to mTORC1; or (c) isotype levels and phosphorylation status of AGC family kinases such as Akt, SGK and PKC (for example, levels of SGK1 and Akt2, and phosphorylation of PKC-alpha/beta). These factors, taken together, constitute a signature of a global cellular response to stress, such as inflammatory stress mediated by the RAGE system.

In diabetic humans and db/db mice the receptor for advanced glycated end products (RAGE) is activated by systemic ligands such as amphoterin and glycated hemoglobin (Goldin A et al [2006] Circulation 114: 597-605). RAGE has been implicated in the development of kidney dysfunction consequent to elevated blood sugar (Tan A L et al [2007] Semin. Nephrol. 27:130-143). The intracellular biochemical events downstream of RAGE activation leading to the loss of kidney function and albuminuria in db/db mice are not well understood. RAGE blockade through the use of soluble RAGE decoys has been proposed as a method for controlling complications of diabetes in humans (Yamagishi S et al [2007] Curr. Drug Targets 8:1138-1143; Koyama H et al [2007] Mol Med 13:625-635). Kidney mesangial cell matrix expansion characterized by excessive deposition of collagen-IV and fibronectin is an often-cited correlate of disease progression (Tsilibary E C et al [2003] J. Pathol. 200: 537-546). However, effective interventions based on this hypothesis have yet to be developed. Recently, the inhibition of protein kinase C (PKC) isoforms has been proposed as a possible therapeutic intervention for kidney disease (Tuttle K R et al [2003] Am. J. Kidney Dis. 42: 456-465). A peptide capable of inhibiting PKC beta II in cultured cells has been described (Ron D et al [1995] J. Biol. Chem. 270: 24180-24187). Correlation matrices or dendograms (Peterson L E [2003] Comput. Methods Programs Biomed. 70: 107-119) constructed from RAGE-adaptive datasets gathered in cultured kidney cell and kidney tissue extracts can help identify reliable biochemical correlates of disease, and can guide the development of effective therapeutic interventions. Although correlations do not reveal causative links, the clustering of biochemical correlates can help define 'virtual regulons' around which hypothesis-driven interventions can be designed and tested. This invention describes methods for surveying a panel of intracellular biochemical readouts in cultured human embryonic kidney (HEK) 293 cells challenged with glycated hemoglobin and various chemical and peptide inhibitors. From these data a method is described for selecting a subset of readouts that are significantly impacted by RAGE ligand in these cells. Taken together, these readouts are referred to as an "adaptive signature". In this context, RAGE ligand is referred to as a "provocative agent" for the derivation of adaptive signatures. A provocative agent is a chemical or biological substance that provokes a change in cellular signaling that resembles, at least in part, the changes seen in a disease condition. Adaptive signature refers to the delta, or difference in readouts, between cells that are treated with a specific provocative agent and cells that are treated with control, such as saline. Similar methodology can be applied to tissues from animals or humans that have been exposed to varying levels of a provocative agent. As an example, kidney extracts from albuminuric db/db mice can be assayed for these selected biochemical markers and compared with a group of control animals who have not developed albuminuria. Correlation matrices constructed from these data can subsequently suggest possible modifications to our current understanding of diabetic kidney disease, based on the adaptive signatures revealed. Statistical clustering of deltas, suggesting common regulation, can be used to assign "virtual regulons." Three key features of this methodology are (a) the choice of provocative agent (b) the use of delta values as opposed to the more traditional approach of using actual biochemical assay values in profiling, and (c) the use of correlation matrices or dendograms to generate virtual regulon clusters based on related adaptive response, rather than logical pathway analysis.

Despite the worldwide epidemic of chronic kidney disease complicating diabetes mellitus, current therapies directed against nephroprogression are limited to angiotensin conversion or receptor blockade. Nonetheless, additional therapeutic possibilities are slowly emerging. The diversity of therapies currently in development reflects the pathogenic complexity of diabetic nephropathy. The three most important candidate drugs currently in development include a glycosaminoglycan, a protein kinase C (PKC) inhibitor and an inhibitor of advanced glycation (Williams M E [2006] *Drugs*. 66: 2287-2298). Treatment of hypertrophic conditions of the heart and kidney using protein kinase C-beta inhibitors (Koya D et al [2000] *FASEB J.* 14: 439-447) represents an alternative to RAGE blockade and TGF-beta-1 blockade approaches to new interventions in hypertrophic disease states.

Renal failure characterized by proteinuria and mesangial cell expansion is observed in a number of non-diabetic states. Many forms of renal disease that progress to renal failure are characterized histologically by mesangial cell proliferation and accumulation of mesangial matrix. These diseases include IgA nephropathy and lupus nephritis. Bone marrow transplantation (BMT) is an effective therapeutic strategy for leukemic malignancies and depressed bone marrow following cancer. However, its side effects on kidneys have been reported. (Otani M et al [2005] *Nephrology* 10: 530-536). Some hematological malignancies associated with nephrotic syndrome include Hodgkin's and non-Hodgkin's lymphomas and chronic lymphocytic leukemia (Levi I [2002] *Lymphoma*. 43: 1133-1136). Cancer drugs such as mitomycin, cisplatin, bleomycin, and gemcitabine (Saif M W and McGee P J [2005] *JOP.* 6: 369-374) and the anti-angiogenic agent bevacizumab (Avastin) (Gordon M S and Cunningham D [2005] *Oncology.* 69 Suppl 3: 25-33) and irradiation are also suggested to be nephrotoxic. Moreover, the observed cardiotoxicity of drugs such a 5-fluorouracil and capecitabine may be secondary to renal toxicity of these drugs (Jensen S A and Sorensen J B [2006] *Cancer Chemother Pharmacol.* 58: 487-493). There are a large number of glomerular diseases that may be responsible for a nephrotic syndrome, the most frequent in childhood being minimal change disease. Denys-Drash syndrome and Frasier syndrome are related diseases caused by mutations in the WT1 gene. Familial forms of idiopathic nephrotic syndrome with focal and segmental glomerular sclerosis/hyalinosis have been identified with an autosomal dominant or recessive mode of inheritance and linkage analysis have allowed to localize several genes on chromosomes 1, 11 and 17. The gene responsible for the Finnish type congenital nephrotic syndrome has been identified. This gene, named NPHS1, codes for nephrin, which is located at the slit diaphragm of the glomerular podocytes and is thought to play an essential role in the normal glomerular filtration barrier (Salomon R et al [2000] *Curr. Opin. Pediatr.* 12: 129-134).

Familial mutations in parkin gene are associated with early-onset PD. Parkinson's disease (PD) is characterized by the selective degeneration of dopaminergic (DA) neurons in the substantia nigra pars compacta (SNpc). A combination of genetic and environmental factors contributes to such a specific loss, which is characterized by the accumulation of misfolded protein within dopaminergic neurons. Among the five PD-linked genes identified so far, parkin, a 52 kD protein-ubiquitin E3 ligase, appears to be the most prevalent genetic factor in PD. Mutations in parkin cause autosomal recessive juvenile parkinsonism (AR-JP). The current therapy for Parkinson's disease is aimed to replace the lost transmitter, dopamine. But the ultimate objective in neurodegenerative therapy is the functional restoration and/or cessation of progression of neuronal loss (Jiang H, et al [2004] *Hum Mol Genet.* 13 (16): 1745-54; Muqit M M, et al [2004] *Hum Mol Genet.* 13 (1): 117-135; Goldberg M S, et al [2003] *J Biol Chem.* 278 (44): 43628-43635). Over-expressed parkin protein alleviates PD pathology in experimental systems. Recent molecular dissection of the genetic requirements for hypoxia, excitotoxicity and death in models of Alzheimer disease, polyglutamine-expansion disorders, Parkinson disease and more, is providing mechanistic insights into neurotoxicity and suggesting new therapeutic interventions. An emerging theme is that neuronal crises of distinct origins might converge to disrupt common cellular functions, such as protein folding and turnover (Driscoll M, and Gerstbrein B. [2003] *Nat Rev Genet.* 4(3): 181-194). In PC12 cells, neuronally differentiated by nerve growth factor, parkin overproduction protected against cell death mediated by ceramide Protection was abrogated by the proteasome inhibitor epoxomicin and disease-causing variants, indicating that it was mediated by the E3 ubiquitin ligase activity of parkin. (Darios F. et al [2003] *Hum Mol Genet.* 12 (5): 517-526). Overexpressed parkin suppresses toxicity induced by mutant (A53T) and wt alpha-synuclein in SHSY-5Y cells (Oluwatosin-Chigbu Y. et al [2003] *Biochem Biophys Res Commun.* 309 (3): 679-684) and also reverses synucleinopathies in invertebrates (Haywood A F and Staveley B E. [2004] *BMC Neurosci.* 5(1): 14) and rodents (Yamada M, Mizuno Y, Mochizuki H. (2005) Parkin gene therapy for alpha-synucleinopathy: a rat model of Parkinson's disease. *Hum Gene Ther.* 16(2): 262-270; Lo Bianco C. et al [2004] *Proc Natl Acad Sci USA.* 101(50): 17510-17515). On the other hand, a recent report claims that parkin-deficient mice are not themselves a robust model for the disease (Perez F A and Palmiter R D [2005] *Proc Natl Acad Sci USA.* 102 (6): 2174-2179). Nevertheless, parkin therapy has been suggested for PD (Butcher J. [2005] *Lancet Neurol.* 4(2): 82).

Variability within patient populations creates numerous problems for medical treatment. Without reliable means for determining which individuals will respond to a given treatment, physicians are forced to resort to trial and error. Because not all patients will respond to a given therapy, the trial and error approach means that some portion of the patients must suffer the side effects (as well as the economic costs) of a treatment that is not effective in that patient.

For some therapeutics targeted to specific molecules within the body, screening to determine eligibility for the treatment is routinely performed. For example, the estrogen antagonist tamoxifen targets the estrogen receptor, so it is normal practice to only administer tamoxifen to those patients whose tumors express the estrogen receptor. Likewise, the anti-tumor agent trastuzumab (HERCEPTIN®) acts by binding to a cell surface molecule known as HER2/neu; patients with HER2/neu negative tumors are not normally eligible for treatment with trastuzumab. Methods for predicting whether a patient will respond to treatment with IGF-I/IGFBP-3 complex have also been disclosed (U.S. Pat. No. 5,824,467), as well as methods for creating predictive models of responsiveness to a particular treatment (U.S. Pat. No. 6,087,090).

IGFBP-3 is a master regulator of cellular function and viability. As the primary carrier of IGFs in the circulation, it plays a central role in sequestering, delivering and releasing IGFs to target tissues in response to physiological parameters such as nutrition, trauma, and pregnancy. IGFs, in turn, modulate cell growth, survival and differentiation, additionally; IGFBP-3 can sensitize selected target cells to apoptosis in an IGF-independent manner The mechanisms by which it accomplishes the latter class of effects is not well understood but appears to involve selective cell internalization mechanisms and vesicular transport to specific cellular compartments (such as the nucleus, where it may interact with transcriptional elements) that is at least partially dependent on transferrin receptor, integrins and caveolin.

The inventor has previously disclosed certain IGFBP-derived peptides known as "MBD" peptides (U.S. patent application publication nos. 2003/0059430, 2003/0161829, and 2003/0224990). These peptides have a number of properties, which are distinct from the IGF-binding properties of IGFBPs, that make them useful as therapeutic agents. MBD peptides are internalized some cells, and the peptides can be used as cell internalization signals to direct the uptake of molecules joined to the MBD peptides (such as proteins fused to the MBD peptide).

Combination treatments are increasingly being viewed as appropriate strategic options for designed interventions in complex disease conditions such as cancer, metabolic diseases, vascular diseases and neurodegenerative conditions. For example, the use of combination pills containing two different agents to treat the same condition (e.g. metformin plus a thiazolidinedione to treat diabetes, a statin plus a fibrate to treat hypercholesterolemia) is on the rise. It is therefore appropriate to envisage combination treatments that include moieties such as MBD in combination with other agents such as other peptides, antibodies, nucleic acids, chemotherapeutic agents and dietary supplements. Combinations may take the form of covalent extensions to the MBD peptide sequence, other types of conjugates, or co-administration of agents simultaneously or by staggering the treatments i.e. administration at alternating times.

Humanin (HN) is a novel neuroprotective factor that consists of 24 amino acid residues. HN suppresses neuronal cell death caused by Alzheimer's disease (AD)-specific insults, including both amyloid-beta (betaAbeta) peptides and familial AD-causative genes. Cerebrovascular smooth muscle cells are also protected from Abeta toxicity by HN, suggesting that HN affects both neuronal and non-neuronal cells when they are exposed to AD-related cytotoxicity. HN peptide exerts a neuroprotective effect through the cell surface via putative receptors (Nishimoto I et al [2004] *Trends Mol Med* 10: 102-105). Humanin is also a neuroprotective agent against stroke (Xu X et al [2006] *Stroke* 37: 2613-2619). As has previously been demonstrated, it is possible to generate both single-residue variants of humanin with altered biological activity and peptide fusions of humanin to other moieties (Tajima H et al [2005] *J. Neurosci Res.* 79 (5): 714-723; Chiba T et al. [2005] *J. Neurosci.* 25: 10252-10261). This indicates the feasibility of combining humanin peptide sequences with, for example, MBD-based therapeutic peptides or, alternatively, the therapeutic segments of previously described MBD-linked therapeutic peptides. The solution structures of both native humanin and its S14G variant have been described (Benaki D et al [2005] *Biochem Biophys Res Comm* 329: 152-160; Benaki D et al [2006] *Biochem Biophys Res Comm* 349: 634-642) thereby potentially facilitating the design of mutant or derivative sequences. The amino acid sequence of humanin is MAPRGFSCLLLLT-SEIDLPVKRRA (SEQ ID NO: 1) and the amino acid sequence of the variant is MAPRGFSCLLLLT-GEIDLPVKRRA (SEQ ID NO:2). Humanin binds a C-terminal domain of IGFBP-3 (Ikonen M et al [2003] *Proc Nat Acad Sci.* 100: 13042-13047). The binding of Zinc(II) to humanin was recently described (Armas A et al [2006] *J. Inorg Biochem* 100: 1672-1678). Therefore humanin may be considered a metal-binding therapeutic peptide.

Potentially therapeutic peptide sequences have been disclosed in the scientific literature. Many of these require cell internalization for action, which limits their in vivo utility without an appropriate delivery system. Peptide sequences that bind and possibly inhibit MDM2 (Picksley S M et al [1994] *Oncogene.* 9: 2523-2529), protein kinase C-beta (Ron D et al [1995] *J Biol Chem.* 270: 24180-24187), p38 MAP kinase (Barsyte-Lovejoy D et al [2002] *J Biol Chem.* 277: 9896-9903), DOK1 (Ling Y et al [2005] *J Biol Chem.* 280: 3151-3158), NF-kappa-B nuclear localization complex (Lin Y Z et al [1995] *J Biol Chem.* 270: 14255-14258), IKK complex (May M J et al [2000] *Science.* 289:1550-1554) and calcineurin (Aramburu J et al [1999] *Science.* 285: 2129-33) have been described.

We have shown that MBD peptide-mediated delivery of bioactive molecules in vivo can be applied to disease processes such as cancer (Huq A, et al [2009] *Anti-Cancer Drugs* 20: 21-31) and diabetes, as described above. Nephrilin, a peptide containing the MBD scaffold, is bioactive in reducing albuminuria in diabetic mice. Nephrilin was designed to interfere with mTORC2 complex and has been shown to disrupt the association of IRS proteins with Rictor. Similar approaches may be used to disrupt mTORC2 and IRS protein activity in human disease by competing the physical interaction of Rictor with obligate cofactors such as PRR5/Protor and Sin1/MIP1. The competing molecule may be a cell-penetrating peptide, protein, antibody or nucleic acid, or a small chemical molecule. In this work we describe in vitro assay systems that facilitate rapid screening of candidate molecules for such a purpose. Any metabolic, systemic, degenerative, or inflammatory disease process may be a candidate for interventions using such molecules.

A noteworthy observation from this work is the previously undocumented elevation of SGK1 in the spleen tissue of db/db mice. Post-hoc subgroup analysis of control animals showed a small (~10%) but significant exacerbation of kidney disease marker elevation in the subgroup with higher spleen SGK1. Nephrilin, but not anephril, was able to reduce spleen SGK1 significantly. A possible subject for future study would be to see if SGK1 is elevated in the circulating leukocytes of animals that exhibit elevated spleen SGK1, and whether a diagnostic possibility exists for predicting the severity of disease based on SGK1 levels in white blood cells.

The central role played by mTORC2 in regulating diseases of aging has not been previously documented. Nephrilin, an inhibitor of the binding of Rictor—the canonical component of mTORC2 complex—to its binding partners or cofactors such as Protor/PRR5, Sin1 and IRS proteins, is the only specific inhibitor of its class described to date. The inventor has shown, for the first time, that nephrilin can reverse disease processes relating to complications of diabetes and hypertension; acute kidney injury from rhabdomyolysis or xenotoxic stress with platinum compounds such as cisplatin and carboplatin or aminoglycoside antibiotics such as gentamycin; and cancer metastasis. These results implicate mTORC2 as a central regulator of diseases of aging. Fundamental common mechanisms suggested for the gamut of diseases of aging—the so-called diseases of western civilization—include oxidative stress [Pinton P and Rizzuto R (2008) *Cell Cycle.* 7(3): 304-308], loss of circadian circuitry [Uchida Y et al (2010) *Biol. Pharm. Bull.* 33(4) 535-544], loss of selective protein turnover mechanisms [Hussain S et al (2009) *Cell Cycle* 8:11, 1688-1697], and the epithelial-mesenchymal transition, EMT [Slattery C et al (2005) *American Journal of Pathology,* 167(2): 395-407]. The inventor has shown that biochemical signatures associated with each of these pathways can be reversed by treatment with nephrilin and has demonstrated, for the first time, that specific inhibition of mTORC2 (which should not be confused with the much better-understood rapamycin-sensitive complex mTORC1) may be the key to controlling diseases of aging. Thus, therapeutic agents that disrupt binding of Rictor (the canonical component mTORC2) to its binding partners are of particular interest in the treatment of metabolic and cardiovascular diseases, especially those characterized by some underlying combination of insulin resistance, hyperglycemia, hypertension and hyperlipidemia; cancer progression and metastasis; acute kidney injury (AKI) in critical care settings (including sepsis, systemic inflammatory conditions such as shock, post-operative stress such as after cardiopulmonary bypass or transplant, burns, pancreatitis, rhabdomyolysis, xenobiotic stresses caused by cocaine, alcohol, aminoglycoside antibiotics, antiviral compounds or platinum compounds; neurodegenerative diseases such as Parkinson's Alzheimer's, Huntington's and ALS/Lou Gehrig's disease; ototoxicities; autoimmune conditions such as lupus erythematosus and multiple sclerosis; genetic diseases such as cystinosis, Fanconi's and other conditions affecting mitochondrial respiration; pulmonary diseases, especially COPD and asthma; ocular diseases such as cataracts and retinopathies, especially diabetic complications; and liver diseases, including chronic viral infections such as hepatitis. These disease states are now increasingly viewed as secondary to chronic inflammatory conditions that may, in turn, relate to oxidative stress. A correlation between oxidative stress and processes of aging may explain the rising incidence of these diseases as a direct consequence of an aging population.

A key regulator of oxidative damage and aging is the adapter protein p66shc. Activation of this molecule by phosphorylation at serine 36 leads to mitochodrial translocation and increased production of free oxygen radicals. P66shc gene knockout mice live significantly longer and are protected from many of the diseases of aging listed above [Pinton P and Rizzuto R (2008) *Cell Cycle.* 7(3): 304-308]. The inventor has shown for the first time, that mTORC2 directly regulates the activation of protein kinase C beta-II (PKC-beta-II) by phosphorylation at threonine 641. PKC-beta was shown to be the activator of p66shc by phosphorylation of S36 [Pinton, et al. (2007) *Science* 315: 659-663]. Nephrilin reverses both PKC-beta-II-T641 and p66shc-S36 phosphorylation events.

A recently recognized histological consequence of cellular stress is the formation of microscopically visible punctate structures in the nuclei of stressed cells [Bart J. et al (2008) *Cytometry* 73A: 816-824]. The inventor has shown, in diseased hypertensive animals, the presence of such structures in kidney cells by immunohistochemical staining. The incidence of such structures is much reduced in animals treated with the mTORC2 inhibitor, nephrilin.

Epithelial cells of renal proximal tubules (PTECs) are known to be exquisitely sensitive to p66shc-mediated oxidative stress [Sun L et al (2010) *Am J Physiol Renal Physiol.* 299(5): F1014-F1025]. Damage to PTECs can be monitored by measuring albumin or lipocalin-2/NGAL in urine by using commercially available kits. In many of the proinflammatory disease conditions listed above, elevated levels of NGAL or albumin have been documented. This is especially true of AKI settings such as those encountered in patients with burns, hypoperfusion, pancreatitis and sepsis [Cruz D et al (2010) *Intensive Care Med* 36:444-451]. In AKI, moreover, a proinflammatory condition reminiscent of human systemic inflammatory states encountered in critical care settings, as enumerated above, can be generated in experimental animals by placing artificial stress on kidneys, such as in rhabdomyolysis and gentamycin models [Zager R et al (2006) *Am J Physiol Renal Physiol* 291:F546-F556]. The inventor has shown, for the first time, that this type of proinflammatory state is regulated by mTORC2 and can be successfully treated by an inhibitor of mTORC2, nephrilin.

All references cited herein, including patent applications and publications, are incorporated by reference in their entirety.

SUMMARY OF THE INVENTION

The present invention provides methods of understanding, diagnosing and treating disease conditions in a mammal, especially inflammatory disease conditions, by generating adaptive signatures using a provocative agent. The invention provides compositions of molecules selected based on their impact upon adaptive signatures. In addition, the invention provides for inhibitors of mTORC2. Inflammatory and proinflammatory disease conditions include but are not limited to diabetes, gastrointestinal disease, obesity, metabolic and cardiovascular diseases (especially those characterized by some underlying combination of insulin resistance, hyperglycemia, hypertension and hyperlipidemia); cancer progression and metastasis; acute kidney injury (AKI) in critical care settings (including sepsis, systemic inflammatory conditions such as shock, post-operative stress such as after cardiopulmonary bypass or transplant, burns, pancreatitis, rhabdomyolysis, xenobiotic stresses caused by cocaine, alcohol, aminoglycoside antibiotics, antiviral compounds or platinum compounds; neurodegenerative diseases such as Parkinson's Alzheimer's, Huntington's and ALS/Lou Gehrig's disease; ototoxicities; autoimmune conditions such as lupus erythematosus and multiple sclerosis; genetic diseases such as cystinosis, Fanconi's and other conditions affecting mitochondrial respiration; pulmonary diseases, especially COPD and asthma; ocular diseases such as cataracts and retinopathies, especially diabetic complications; and liver diseases, including chronic viral infections such as hepatitis.

In some aspects, the invention provides a method useful for generating adaptive biochemical signatures, said method comprising contacting a live cell with a provocative agent and measuring the adaptive ratio of selected biochemical analytes in cell extracts, extracellular fluids or media; using clustering algorithms to recognize virtual regulons in said adaptive ratio data; hypothesis-based testing of therapeutic or diagnostic candidates based on virtual regulons selected using said clustering algorithms; and thereby developing new and effective diagnostic or therapeutic modalities for treating a live mammal. In some cases the provocative agent is a RAGE ligand. In some cases, the provocative agent is glycated hemoglobin. In some cases, the clustering algorithms involve the construction of Pearson correlation matrices or dendograms. In some cases the therapeutic candidates are peptides or proteins.

A key insight into fundamental disease processes is that the change (or delta) in the levels of key pathway intermediates can be a more useful diagnostic readout than the steady-state levels of those same intermediates in the diseased cell(s). Thus, this invention focuses of "delta signatures": a cluster of delta readouts in response to a particular, defined stimulus. For example, changed ratios of IRS-2 to IRS-1, or mTORC2 to mTORC1, or AKT2 to AKT1, or SGK1 to another SGK isoform; or changed ratios of phosphorylation events at AKT-Thr308 to AKT-Ser473; mTOR phosphorylated at Ser2448 versus Ser2481; or phosphorylation of PKC-alpha/beta at Thr638/641 compared to other PKC phosphorylation events; and other such analytes whose deltas can be observed when kidney cells are exposed to the provocative agent glycated hemoglobin at concentrations ranging from 20-125 ug/ml. Thus, "adaptive biochemical signature" is composed of delta values, whereas the more conventional "biochemical signature" is composed of steady-state values of selected analytes.

The invention provides methods for generating adaptive biochemical signatures for a disease indication, comprising contacting cells with a provocative agent capable of inducing the disease indication and measuring the adaptive ratio of selected biochemical analytes in cell extracts, extracellular fluids or media, using clustering algorithms to recognize virtual regulons in said adaptive ratio data followed by hypothesis-based testing of therapeutic or diagnostic candidates based on virtual regulons selected using said clustering algorithms and thereby developing diagnostic or therapeutic modalities for treating an individual with the disease condition. In some cases the provocative agent is a RAGE ligand, including but not limited to glycated hemoglobin. In some aspects of the invention, the clustering algorithms involve the construction of Pearson correlation matrices or dendograms. Examples of therapeutic or diagnostic candidates include but are not limited to peptides, proteins, small chemical molecules and nucleic acids.

In some aspects, the invention provides an agent capable of disrupting the physical association of Rictor protein with one of its obligate cofactors, thereby reversing the effects of an adaptive biochemical signature. Examples of agents include but are not limited to peptides, proteins, antibodies, nucleic acid and small chemical molecules.

The invention provides an adaptive biochemical signature expressing the alteration caused by a provocative agent to the intracellular ratios of isoforms and/or phosphorylation status of any two members of the group comprising IRS proteins, mTOR complexes, and AGC kinases following exposure of cells to the provocative agent; wherein IRS proteins comprise IRS-1 and IRS-2, mTOR complexes comprise mTORC1 and mTORC2, and AGC kinases comprise Akt, SGK and PKC; and wherein the ratio of analytes and/or phosphorylation patterns forms an adaptive biochemical signature.

The invention provides methods of generating an adaptive biochemical signature comprising contacting cells with a provocative agent and measuring two or more of the following: a) isotype levels or phosphorylation status of IRS-1 and IRS-2; b) ratio of active mTORC2 to mTORC1; c) phosphorylation of mTor at Ser2448 versus Ser2481; and d) isotype levels and phosphorylation status of ACG family kinases selected from Akt, SGK and PKC subfamilies; wherein the ratio of analytes and/or phosphorylation patterns form an adaptive biochemical signature. In some cases, the adaptive biochemical signature is compared to the biochemical signature formed by the ratio of analytes and/or phosphorylation patterns from the cells before treatment with the provocative agent. In some aspects of the invention the provocative agent is a RAGE ligand; for example, glycated hemoglobin or amphoterin. In some aspects of the invention the cells are kidney cells including but not limited to human embryonic kidney (HEK) 293 cells (also referred to as 293 cells) or a human kidney mesangial cells. In some aspects, the population of cells in further contacted with a therapeutic agent.

In some aspects, the invention provides methods of generating an adaptive biochemical signature for diabetes-associated kidney disease comprising contacting cells with a provocative agent capable of inducing kidney disease and measuring the levels or phosphorylation of one or more analytes in cell extracts, extracellular fluids or culture media. The analytes include but are not limited to IRS-1, IRS-2, mTOR, mTORC1, mTORC2, Raptor, Rictor, SGK1, SGK2, SGK3, collagen-IV, fibronectin, c-Jun, c-myc, Erk1/2, P38MAPK, JNK, P38-alpha, PKC-alpha, PKC-beta, PKC-Delta, PKC-gamma, PKC-Theta, PKC-zeta, PKC-lambda, PKC-iota, PKD, PKCmu, AKT, AKT1, AKT2, AKT3, MKK3, MKK6, ATF2, paxillin, GSK3B, Rac1, Sirt1, and cdc242. Adaptive ratio data may then be assigned into virtual regulons using clustering algorithms whereby the levels of analytes and/or phosphorylation patterns in the virtual regulons form the adaptive biochemical signature. In some cases, the provocative agent is a RAGE ligand. Examples of RAGE ligands include but are not limited to glycated hemoglobin and amphoterin. In some cases, the cells are kidney cells; for example, 293 cells or human kidney mesangial cells. In some cases, the cells are contacted with the provocative agent in vivo. In some aspects, the cells are further contacted with a therapeutic agent, including but not limited to peptides, proteins, antibodies, nucleic acids, and small chemical molecules.

The invention also provides methods of generating an adaptive biochemical signature for diabetes-associated kidney disease comprising contacting cells with a provocative agent capable of inducing kidney disease and measuring two or more of the following: a) isotype levels or phosphorylation status of IRS-1 and IRS-2; b) ratio of active mTORC2 to mTORC1; c) phosphorylation of mTor at Ser2448 versus Ser2481; and d) isotype levels and phosphorylation status of ACG family kinases selected from Akt, SGK and PKC subfamilies; wherein the ratio of analytes and/or phosphorylation pattern forms an adaptive biochemical signature for diabetes-associated kidney disease. In some cases, the adaptive biochemical signature is compared to the biochemical signature formed by the ratio of analytes and/or phosphorylation patterns from the cells before treatment with the provocative agent. In some cases, the provocative agent is a RAGE ligand; for example, glycated hemoglobin or amphoterin. In some aspects, the cells are kidney cells; for example, HEK 293 cells or human kidney mesangial cells. In some aspects of the invention, the cells are further contacted with a therapeutic agent.

In some aspects, the invention provides methods for screening a candidate therapeutic agent for the treatment of diabetes-associated kidney disease comprising contacting cells with a provocative agent capable of inducing kidney disease and the candidate therapeutic agent, and measuring levels or phosphorylation of one or more analytes in cell extracts, extracellular fluids or culture media, wherein the analytes are selected from the group consisting of IRS-1, IRS-2, mTOR, mTORC1, mTORC2, Raptor, Rictor, SGK1, SGK2, SGK3, collagen-IV, fibronectin, c-Jun, c-myc, Erk1/

2, P38MAPK, JNK, P38-alpha, PKC-alpha, PKC-beta, PKC-Delta, PKC-gamma, PKC-Theta, PKC-zeta, PKC-lambda, PKC-iota, PKD, PKCmu, AKT, AKT1, AKT2, AKT3, MKK3, MKK6, ATF2, paxillin, GSK3B, Rac1, Sirt1, and cdc242. Adaptive ratio data may then be assigned into virtual regulons using clustering algorithms whereby the levels of analytes and/or phosphorylation patterns in the virtual regulons form the adaptive biochemical signature. The adaptive biochemical signature from cells contacted with the RAGE ligand plus the candidate therapeutic agent may be compared with the adaptive biochemical signature from cells that had been contacted with RAGE ligand alone; whereby a statistically significant change in the adaptive biochemical signature following treatment with the provocative agent and the candidate therapeutic agent compared to the provocative agent alone is indicative of a therapeutic agent for the treatment of diabetes-associated kidney disease. In some cases, the provocative agent is a RAGE ligand; for example, glycated hemoglobin or amphoterin. In some aspects, the cells are kidney cells; for example, HEK 293 cells or human kidney mesangial cells. In some aspects, the cells are contacted with the provocative agent in vivo. Examples of candidate therapeutic agents include but are not limited to peptides, proteins, antibodies, nucleic acids, and small chemical molecules. In some aspects, the invention provides therapeutic agents identified by the methods of the invention.

In some aspects, the invention provides methods for random search or rational design of a therapeutic agent, said method comprising either (a) in vitro or in vivo inhibition of binding between Rictor and its binding partners selected from a group comprising Protor/PRR5, Sin1, IRS1 and IRS2; or (b) counter-regulation of a promoter-reporter gene construct in a cell line or live organism wherein the promoter is selected from a group of genes comprising B4galNT4, UCHL1, PER2, and their respective orthologs and paralogs.

In some aspects, the invention provides methods for treating an inflammatory condition in a mammal exhibiting a biochemical signature characterized by (a) a physiological attribute selected from the group comprising elevated urinary albumin, elevated urinary lipocalin-2/NGAL, and elevated plasma TNF-alpha response to inflammatory stimulus; and (b) a tissue phosphorylation attribute selected from the group comprising elevated PKC-beta-II-T641 and elevated p66shc-S36; and (c) an altered gene transcript level attribute selected from the group comprising elevated B4galNT4, down-regulated UCHL1, and downregulated PER2; said method comprising treating the mammal with a therapeutic agent that disrupts the binding of Rictor to a binding partner selected from the group comprising PRR5/Protor, Sin1, IRS1 and IRS2; thereby reducing or reversing the inflammatory condition.

In embodiments of the invention, the therapeutic agent is capable of disrupting the physical association of Rictor protein with one of its binding partners selected from the group comprising Protor/PRR5, Sin1, IRS1 and IRS2, thereby reversing the effects of a biochemical signature characteristic of an inflammatory condition.

In embodiments of the invention, the composition can be administered via any route including but not limited to intravenous, oral, subcutaneous, intraarterial, intramuscular, intracardial, intraspinal, intrathoracic, intraperitoneal, intraventricular, sublingual, transdermal, and inhalation.

In an embodiment of the invention, nucleic acids encoding fusion proteins are used in methods of diagnosing or treating an inflammatory disease condition. Inflammatory disease conditions include but are not limited to cancer, diabetes, cardiovascular disease, obesity, metabolic disease, neurodegenerative disease, gastrointestinal disease, autoimmune disease, rheumatological disease and infectious disease.

In some embodiments the invention provides nucleic acids of the fusion polypeptide and vectors comprising nucleic acids encoding the polypeptides of the invention.

In another aspect the invention provides methods of diagnosing or treating an inflammatory disease condition comprising administering an effective amount a polypeptide of the invention to a mammal. Inflammatory disease conditions include but are not limited to cancer, diabetes, cardiovascular disease, chronic kidney disease, acute kidney injury, retinopathy, obesity, metabolic disease, neurodegenerative disease, gastrointestinal disease, autoimmune disease, rheumatological disease, infectious disease, genetic disease, and xenotoxicity.

In certain aspects the invention provides a method of diagnosing or treating an inflammatory disease condition comprising administering an effective amount of humanin or humanin-S14G to a mammal Inflammatory disease conditions include but are not limited to cancer, cardiomyopathy, nephropathy, retinopathy, obesity, autoimmune disease, rheumatological disease and infectious disease.

The compositions of the invention may be administered by means which include but are not limited to intravenous, oral, subcutaneous, intraarterial, intramuscular, intracardial, intraspinal, intrathoracic, intraperitoneal, intraventricular, sublingual, transdermal, and inhalation. In some embodiments, the composition is administered to a mammal at less than about 20 mg/kg/day.

The invention includes methods to diagnose or treat inflammatory diseases conditions by administering nucleic acids and/or vectors encoding polypeptides of the invention to a mammal.

One aspect of the invention includes methods of diagnosing or treating a disease condition in a mammal comprising administering a provocative agent to a mammal or cultured cell, wherein the agent modulates the ratio of at least one key intracellular metabolic intermediate to another in said mammal Disease conditions include but are not limited to cancer, diabetes, cardiovascular disease, kidney disease, retinopathy, obesity, metabolic disease, neurodegenerative disease, gastrointestinal disease, autoimmune disease, rheumatological disease and infectious disease.

In one aspect, the invention provides methods for treating an inflammatory condition in a mammal exhibiting a biochemical signature characterized by (a) one or more of a physiological attribute selected from the group consisting of elevated urinary albumin, elevated urinary lipocalin-2/NGAL, and elevated plasma TNF-alpha response to inflammatory stimulus; and (b) one or more of an altered kidney gene transcript level attribute elevated B4galNT4, down-regulated UCHL1, and downregulated PER2; wherein the method comprising treating the mammal with a therapeutic agent that disrupts the binding of Rictor to a binding partner selected from the group consisting of PRR5/Protor, Sin1, IRS1 and IRS2; thereby reducing or reversing the inflammatory condition. In some embodiments, the inflammatory condition is selected from a group consisting of cancer, metabolic disease, acute kidney injury, neurodegenerative disease, autoimmune disease, infectious disease, genetic disease, and xenotoxicity.

In some aspects, the invention provides a therapeutic agent capable of disrupting the physical association of Rictor protein with one of its binding partners selected from the group consisting of Protor/PRR5, Sin1, IRS1 and IRS2, thereby reversing the effects of a biochemical signature characteristic of an inflammatory condition in a mammal exhibiting a biochemical signature characterized by (a) one or more of a physiological attribute selected from the group consisting of elevated urinary albumin, elevated urinary lipocalin-2/NGAL, and elevated plasma TNF-alpha response to inflammatory stimulus; and (b) one or more of an altered kidney gene transcript level attribute elevated B4galNT4, downregulated UCHL1, and downregulated PER2; wherein the therapeutic agent disrupts the binding of Rictor to a binding partner selected from the group consisting of PRR5/Protor, Sin1, IRS1 and IRS2; thereby reducing or reversing the inflammatory condition. In some embodiments the agent is a peptide, a protein, an antibody, a nucleic acid, or a small chemical molecule. In some embodiments, the therapeutic agent is nephrilin or a sequence variant thereof. For example, the variant may have 80%, 90%, 95% or 99% identity to nephrilin.

In another aspect, the invention provides methods to identify a therapeutic agent according to the invention, wherein the method comprising either (a) exposing rictor and one of its binding partners selected from the group consisting of Protor/PRR5, Sin1, IRS1 and IRS2 to a candidate therapeutic agent in vitro or in vivo; measuring binding of rictor to the binding partner, and comparing binding of Rictor and its partner in the presence of the candidate therapeutic agent with binding in the absence of the candidate therapeutic agent; or (b) exposing a cell to the candidate therapeutic agent, measuring expression of a promoter-reporter gene construct selected from the group consisting of B4galNT4, UCHL1, PER2, and their respective orthologs and paralogs, and comparing expression of the promoter-reporter gene construct in the presence of the candidate therapeutic agent with expression of the promoter-gene construct in the absence of the candidate therapeutic agent. As such, a therapeutic agent is identified by inhibition of binding of Rictor to its binding partner or by counter regulation of the promoter gene construct. In some embodiments, the cell is in vitro; for example, in a cell culture. In some embodiments, the cell is in vivo; for example, in an organism such as a mammal. In some embodiments, therapeutic agents are selected by random search prior to the identification steps outlined above. In some embodiments, the candidate therapeutic agent is first selected by rational design prior to the identification steps outlined above. In some embodiments, the invention provides a therapeutic agent identified by the methods outlined above.

DISCLOSURE OF THE INVENTION

The present invention provides a method for generating adaptive signatures, said method comprising contacting a provocative agent to live cells, whereby said contact results in altered biochemical readouts.

The invention also provides a method for obtaining diagnostic information from live cells comprising the steps of: (a) defining an adaptive signature; and (b) developing a convenient diagnostic readout for said signature. The diagnostic readout can be an algorithmic, enzymatic, colorimetric, or a fluorimetric readout.

The invention also provides a method for modifying a disease process or a cellular process, said method comprising the steps of: (a) administering a provocative agent to live cells and generating an adaptive signature; (b) selecting a candidate therapeutic agent by co-administering various test compounds with the provocative agent, to test their ability to modify the adaptive signature caused by the provocative agent; and (b) delivering said candidate therapeutic agent into said live cells, whereby said disease process or said cellular process in said live cells is modified. In some embodiments, the disease process is selected from the group consisting of neurodegenerative, cancer, autoimmune, inflammatory, cardiovascular, diabetes, osteoporosis and ophthalmic diseases. In some embodiments, the cellular process is selected from the group consisting of transcriptional, translational, protein folding, protein degradation and protein phosphorylation events.

A similar method may be used to select a diagnostic agent instead of a therapeutic agent. In some embodiments, the agent is a protein or a peptide. In some embodiments, the agent is a nucleic acid. In some embodiments, the agent is a small molecule.

In some embodiments, the live cells are in a subject, such as a mammal. For example, the live cells are in a human. In some embodiments, the live cells are in a tissue or in cell culture.

The invention provides methods for identifying individuals who are candidates for treatment with therapies.

Metastasis is the primary cause of cancer-related mortality in the world. Unlike the primary tumors from which they arise, metastases are diseases of adaptivity. It is a goal of this work to address this unmet need by developing agents that affect cellular adaptive responses, as opposed to growth and survival.

The human cancer and corresponding normal cell lines to be used in testing can be obtained from the American Type Culture Collection (ATCC). They are well characterized and have been extensively used in vitro and in vivo. Breast cancer cell lines (MCF7, MDA-MB-231, MX-1), leukemia cell lines (RPMI-8226, CCRF-CEM, MOLT-4), and prostate cancer cell lines (PC3, DU145, LNCAPs) were cultured in RPMI-1640 media supplemented with 10% FBS. Paired breast cancer and non-cancer cell lines (CRL7364/CRL7365, CRL7481/CRL7482, HTB-125/Hs578T) were cultured in DMEM media supplemented with 10% FBS. Normal cell lines such as MCF-10A, HMEC human T-cells were cultured in medias specified by the manufacturer. Cell line pairs of primary versus metastatic cells from the same individuals are also available from ATCC (CCL-228/CCL-227, CRL-1675/CRL-1676, CRL-7425/CRL-7426).

Animal models of metastatic disease are described in this invention. Successful engraftment of both human hematopoietic and non-hematopoietic xenografts requires the use of severe combined immunodeficient (SCID) mice as neither bone marrow involvement nor disseminated growth are regularly observed using thymectomized, irradiated or nude mice. The mice used to establish a human-mouse xenograft model were purchased from Taconic. Mice were bred by crossing C57BL/6J gc KO mice to C57BL/10SgSnAi Rag-2 deficient mice. The gc KO is a deletion of the X-chromosome linked gc gene resulting in a loss of NK cells, a loss of the common g receptor unit shared by an array of cytokines that include IL-2, IL-4, IL-7, IL-9, and IL-15, and as a result only a residual number of T and B cells are produced. To eliminate this residual number of T and B cells, the gc mouse KO mouse was crossed with a C57BL/10SgSnAi recombinase activating-2 (Rag-2) deficient mouse (a loss of the Rag-2 gene results in an inability to initiate V(D)J lymphocyte receptor rearrangements, and mice will lack mature lymphocytes). CCRF-CEM, MDA-MB-231 or MDA-MB-435 xenograft-bearing Rag-2 mice (10 mice per group, 3 groups, approx. $5 \times 10^5$ to $1 \times 10^7$ cancer cells injected per animal per group) are established through intra-cardiac injection. MBD-tagged peptide cocktails ("enhancers") and paclitaxel combinations are intraperitonially (IP) injected into the animals. The groups are divided as follows: saline (group 1), peptide (group 2), and peptide/paclitaxel combination (group 3). Treatment is started on Day 4 with a one-time IP dosage of paclitaxel (group 3). On Day 6, the paclitaxel dose (0.5 mg/kg) is followed by peptide treatment for 7 days (groups 2 and 3). On a daily basis, each mouse receives IP injection of MBD peptide cocktails (in one embodiment, 3 peptide sequences are combined in one cocktail, each peptide administered at a dose of 0.1-5.0 mg/kg). Blood sampling and PCR analysis are carried out at weekly intervals. Approximately 100 ul blood is collected from the saphenous vein. PCR analysis is used on peripheral blood (PB) on Days 3-7 post-injection to determine whether animals have successfully established leukemia/cancer. Cancer cell count levels are monitored during and after treatment as well as at termination. PCR analysis on PB, bone marrow, spleen, liver and lung is used to quantify the cancer cells. At Day 3, prior to treatment, high levels of cancer cells may be seen in PB in the case of leukemia models and low levels of human cancer cells in peripheral organs. Blood and peripheral organs are collected at termination and stored for further analysis (Day 18-45, depending on the experiment). If dietary compounds such as curcumin or lycopene are to be used in the experiment they may be included in the animal diet or force-fed daily or at other specified intervals. It has been shown that blood levels exceeding 20 nM can be achieved for these compounds when fed orally. Dietary supplements curcumin and lycopene were purchased from Sigma. Chemotherapeutics paclitaxel and 5-fluorouracil (5-FU) can be purchased from Sigma. Biphosphonates (Alendronate, Clodronate) have been obtained from EMD Biosciences. At termination of each animal experiment blood and organs are collected and stored at −80° C. To isolate genomic DNA (gDNA) from blood samples the blood & cell culture DNA kit (purchased from Qiagen Inc., Carlsbad, Calif.) can be used to isolate gDNA from tissue samples. gDNA concentrations are established based on spectrophotometer $OD_{260}$ readings. To determine human genomic DNA human-specific primers 5'-TAGCAATAATCCCCATCCTCCATATAT-3' (SEQ ID NO:4) and 5'-ACTTGTCCAATGATGG-TAAAAGG-3' (SEQ ID NO:5), which amplify a 157-bp portion of the human mitochondrial cytochrome b region can be used with 100-500 ng input genomic DNA per PCR reaction, depending on type of tissue. Good results can be achieved using the KOD hot start PCR kit (Novagen, Inc., Madison, Wis.). PCR is performed in a thermal cycler (Perkin Elmer) for 25 or 32 cycles of 30 s at 96° C., 40 s at 59° C., and 1 min at 72° C. The program can be optimized for genomic DNA isolated from mouse tissue.

BRIEF DESCRIPTION OF THE DRAWINGS

FIGS. 4A-B shows biochemical profiling of plasma and kidney tissue protein from 13-week old db/db mice treated with bioactive peptides. Biochemical analysis of plasma and left kidney tissue extracts prepared from 13-week old db/db mice that received daily subcutaneous bolus injections of the indicated peptides from weeks 8 through 13. Group sizes were 4, 8, 6, 6, 8 and 4 (groups A-F, respectively). The correlation matrix was prepared from pairwise correlations between the biochemical values obtained from the 30 animals in groups A, B, C, E and F. Correlations lower than 0.3 (or higher than −0.3) were ignored. p values were calculated relative to saline control group B: $*p<0.05$; $**p<0.01$. See text for discussion of regulons.

FIG. 14 shows the effect of subcutaneously administered nephrilin in Dahl rats. Panel A shows the effect of subcutaneous nephrilin in the Dahl rat model. S represents animals treated with saline, N represents 4 mg/kg nephrilin. Panel B shows the effect of subcutaneously delivered nephrilin on kidney injury in a Dahl model. S represents animals treated with saline, N represents 4 mg/kg nephrilin.

FIG. 15 shows the effects of subcutaneously administered nephrilin in kidneys of Dahl rats. Panel A shows the effect of subcutaneously administered nephrilin in Dahl rats with respect to nuclear bodies. Panel B shows the effect of subcutaneously administered nephrilin in Dahl rats with respect to transdifferentiation.

FIG. 16 shows the effects of subcutaneously administered nephrilin in two models of AKI. S represents animals treated with saline, N represents 4 mg/kg nephrilin.

FIG. 17 shows the pairwise comparisons from gene array analysis (panel A) and the transcript abundance (panel B) of mTORC2-regulated genes. UCHL1 is ubiquitin carboxyterminal hydrolase 1, PER2 is Period 2 a circadian clock gene, and B4galNT4.

FIG. 18 shows the effect of subcutaneously administered nephrilin in a B16 melanoma model.

FIG. 19 shows reagents for screening candidate inhibitors and agonists of mTORC2 binding to its binding partners such as Protor/PRR5, Sin1, IRS1 or IRS2. Panel A shows a map of pSEAP2-Basic-pPER2. Panel B shows the predicted sequence of the RICT1 insert (SEQ ID NO:9) in pYZ85832. Panel C shows the expression of pRICT1 in BL21 cells at 33° C. Lane 1, pre-stained molecular weight markers (MW shown at left); Lane 2, pre-induced; Lane 3, after induction with 0.4 mM IPTG for three hours (induced RICT1 band at ~60 kD).

MODES FOR CARRYING OUT THE INVENTION

Methods of Identifying Candidates for Treatment

Figure 1:
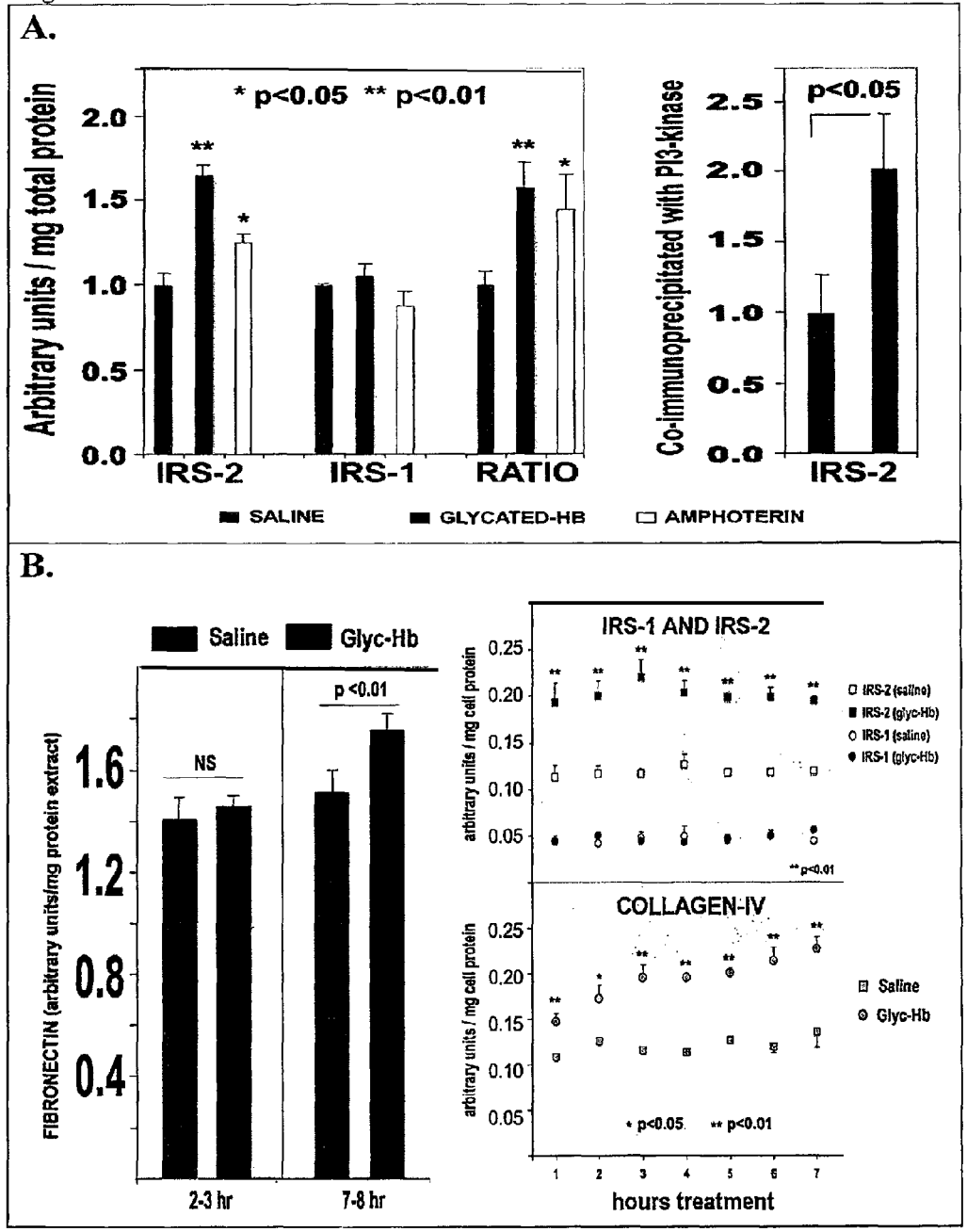
FIG. 1 shows RAGE-induced responses in 293 kidney cells. [A] Left panel: IRS-2 and IRS-1 levels after 4-hour treatment with RAGE ligands amphoterin and glycated hemoglobin. Right panel: PI3-kinase associated IRS-2. [B] Left panel: Fibronectin synthesis after treatment with glycated hemoglobin. Right panel: Time course of induction of IRS-2 and collagen-IV after treatment with glycated hemoglobin.

The invention provides methods for identifying candidates for treatment therapies.

As will be understood by those of skill in the art, the mode of detection of the signal will depend on the exact detection system utilized in the assay. For example, if a radiolabeled detection reagent is utilized, the signal will be measured using a technology capable of quantitating the signal from the biological sample or of comparing the signal from the biological sample with the signal from a reference sample, such as scintillation counting, autoradiography (typically combined with scanning densitometry), and the like. If a chemiluminescent detection system is used, then the signal will typically be detected using a luminometer. Methods for detecting signal from detection systems are well known in the art and need not be further described here.

When more than one biochemical readout is measured (i.e., measured values for two or more readouts are obtained), the sample may be divided into a number of aliquots, with separate aliquots used to measure different readouts (although division of the biological sample into multiple aliquots to allow multiple determinations of the levels of the readouts in a particular sample are also contemplated). Alternately the sample (or an aliquot therefrom) may be tested to determine the levels of multiple readouts in a single reaction using an assay capable of measuring the individual levels of different readouts in a single assay, such as an array-type assay or assay utilizing multiplexed detection technology (e.g., an assay utilizing detection reagents labeled with different fluorescent dye markers).

As will be understood by those in the art, the exact identity of a reference value will depend on the tissue that is the target of treatment and the particular measuring technology used. In some embodiments, the comparison determines whether the measured value is above or below the reference value. In some embodiments, the comparison is performed by finding the "fold difference" between the reference value and the measured value (i.e., dividing the measured value by the reference value).

Although some assay formats will allow testing of biological samples without prior processing of the sample, it is expected that most biological samples will be processed prior to testing. Processing generally takes the form of elimination of cells (nucleated and non-nucleated), such as erythrocytes, leukocytes, and platelets in blood samples, and may also include the elimination of certain proteins, such as certain clotting cascade proteins from blood.

Commonly, adaptive readouts will be measured using an affinity-based measurement technology. Affinity-based measurement technology utilizes a molecule that specifically binds to the readout protein being measured (an "affinity reagent," such as an antibody or aptamer), although other technologies, such as spectroscopy-based technologies (e.g., matrix-assisted laser desorption ionization-time of flight, or MALDI-TOF, spectroscopy) or assays measuring bioactivity (e.g., assays measuring mitogenicity of growth factors) may be used.

Affinity-based technologies include antibody-based assays (immunoassays) and assays utilizing aptamers (nucleic acid molecules which specifically bind to other molecules), such as ELONA. Additionally, assays utilizing both antibodies and aptamers are also contemplated (e.g., a sandwich format assay utilizing an antibody for capture and an aptamer for detection).

If immunoassay technology is employed, any immunoassay technology which can quantitatively or qualitatively measure the adaptive readout in a biological sample may be used. Suitable immunoassay technology includes radioimmunoassay, immunofluorescent assay, enzyme immunoassay, chemiluminescent assay, ELISA, immuno-PCR, and western blot assay.

Likewise, aptamer-based assays which can quantitatively or qualitatively measure the level of a relevant adaptive readout in a biological sample may be used in the methods of the invention. Generally, aptamers may be substituted for antibodies in nearly all formats of immunoassay, although aptamers allow additional assay formats (such as amplification of bound aptamers using nucleic acid amplification technology such as PCR (U.S. Pat. No. 4,683,202) or isothermal amplification with composite primers (U.S. Pat. Nos. 6,251,639 and 6,692,918).

A wide variety of affinity-based assays are known in the art. Affinity-based assays will utilize at least one epitope derived from the adaptive readout protein of interest, and many affinity-based assay formats utilize more than one epitope (e.g., two or more epitopes are involved in "sandwich" format assays; at least one epitope is used to capture the marker, and at least one different epitope is used to detect the marker).

Affinity-based assays may be in competition or direct reaction formats, utilize sandwich-type formats, and may further be heterogeneous (e.g., utilize solid supports) or homogenous (e.g., take place in a single phase) and/or utilize or immunoprecipitation. Most assays involve the use of labeled affinity reagent (e.g., antibody, polypeptide, or aptamer); the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA and ELONA assays.

In a heterogeneous format, the assay utilizes two phases (typically aqueous liquid and solid). Typically readout protein-specific affinity reagent is bound to a solid support to facilitate separation of the readout indicator protein from the bulk of the biological sample. After reaction for a time sufficient to allow for formation of affinity reagent/readout indicator protein complexes, the solid support containing the antibody is typically washed prior to detection of bound polypeptides. The affinity reagent in the assay for measurement of readout proteins may be provided on a support (e.g., solid or semi-solid); alternatively, the polypeptides in the sample can be immobilized on a support. Examples of supports that can be used are nitrocellulose (e.g., in membrane or microtiter well form), polyvinyl chloride (e.g., in sheets or microtiter wells), polystyrene latex (e.g., in beads or microtiter plates), polyvinylidine fluoride, diazotized paper, nylon membranes, activated beads, and Protein A beads. Both standard and competitive formats for these assays are known in the art.

Array-type heterogeneous assays are suitable for measuring levels of adaptive readout proteins when the methods of the invention are practiced utilizing multiple adaptive readout proteins. Array-type assays used in the practice of the methods of the invention will commonly utilize a solid substrate with two or more capture reagents specific for different Adaptive readout proteins bound to the substrate a predetermined pattern (e.g., a grid). The biological sample is applied to the substrate and Adaptive readout proteins in the sample are bound by the capture reagents. After removal of the sample (and appropriate washing), the bound Adaptive readout proteins are detected using a mixture of appropriate detection reagents that specifically bind the various Adaptive readout proteins. Binding of the detection reagent is commonly accomplished using a visual system, such as a fluorescent dye-based system. Because the capture reagents are arranged on the substrate in a predetermined pattern, array-type assays provide the advantage of detection of multiple Adaptive readout proteins without the need for a multiplexed detection system.

In a homogeneous format the assay takes place in single phase (e.g., aqueous liquid phase). Typically, the biological sample is incubated with an affinity reagent specific for the Adaptive readout protein in solution. For example, it may be under conditions that will precipitate any affinity reagent/antibody complexes which are formed. Both standard and competitive formats for these assays are known in the art.

In a standard (direct reaction) format, the level of Adaptive readout protein/affinity reagent complex is directly monitored. This may be accomplished by, for example, determining the amount of a labeled detection reagent that forms is bound to Adaptive readout protein/affinity reagent complexes. In a competitive format, the amount of Adaptive readout protein in the sample is deduced by monitoring the competitive effect on the binding of a known amount of labeled Adaptive readout protein (or other competing ligand) in the complex. Amounts of binding or complex formation can be determined either qualitatively or quantitatively.

Complexes formed comprising Adaptive readout protein and an affinity reagent are detected by any of a number of known techniques known in the art, depending on the format of the assay and the preference of the user. For example, unlabelled affinity reagents may be detected with DNA amplification technology (e.g., for aptamers and DNA-labeled antibodies) or labeled "secondary" antibodies which bind the affinity reagent. Alternately, the affinity reagent may be labeled, and the amount of complex may be determined directly (as for dye-(fluorescent or visible), bead-, or enzyme-labeled affinity reagent) or indirectly (as for affinity reagents "tagged" with biotin, expression tags, and the like).

As will be understood by those of skill in the art, the mode of detection of the signal will depend on the exact detection system utilized in the assay. For example, if a radiolabeled detection reagent is utilized, the signal will be measured using a technology capable of quantitating the signal from the biological sample or of comparing the signal from the biological sample with the signal from a reference sample, such as scintillation counting, autoradiography (typically combined with scanning densitometry), and the like. If a chemiluminescent detection system is used, then the signal will typically be detected using a luminometer. Methods for detecting signal from detection systems are well known in the art and need not be further described here.

When more than one Adaptive readout protein is measured, the biological sample may be divided into a number of aliquots, with separate aliquots used to measure different Adaptive readout proteins (although division of the biological sample into multiple aliquots to allow multiple determinations of the levels of the Adaptive readout protein in a particular sample are also contemplated). Alternately the biological sample (or an aliquot therefrom) may be tested to determine the levels of multiple Adaptive readout proteins in a single reaction using an assay capable of measuring the individual levels of different Adaptive readout proteins in a single assay, such as an array-type assay or assay utilizing multiplexed detection technology (e.g., an assay utilizing detection reagents labeled with different fluorescent dye markers).

It is common in the art to perform 'replicate' measurements when measuring Adaptive readout proteins. Replicate measurements are ordinarily obtained by splitting a sample into multiple aliquots, and separately measuring the Adaptive readout protein (s) in separate reactions of the same assay system. Replicate measurements are not necessary to the methods of the invention, but many embodiments of the invention will utilize replicate testing, particularly duplicate and triplicate testing.

In some aspects of the invention, the following adaptive readout proteins or markers include, but are not limited to: IRS-1 (insulin receptor substrate-1; IRS-1 [*Homo sapiens*] gi|386257|gb|AAB27175.1), IRS-2 (insulin receptor substrate-2 [*Homo sapiens*] gi|18652857|dbj|BAB84688.1), mTORC1 and mTORC2 complexes which are traditionally defined by the protein components Raptor and Rictor respectively, Rictor (RICTOR protein [*Homo sapiens*] gi|30704352|gb|AAH51729.1) >>mTORC2, Raptor (raptor [*Homo sapiens*] gi|21979456|gb|AAM09075.1)>>mTORC1; AKT SUB-FAMILY OF AGC KINASES: AKT1 protein [*Homo sapiens*] gi|18027298|gb|AAL55732.1, AKT2 protein [*Homo sapiens*] gi|111309392|gb|AAI20996.1, AKT3 protein [*Homo sapiens*] gi|62089468|gb|AAH20479.1 (NOTE:AKT is also known as Protein Kinase B, or PKB); SGK SUB-FAMILY OF AGC KINASES: SGK1 Serum/glucocorticoid regulated kinase 1 [*Homo sapiens*] gi|12654839|gb|AAH01263.1, SGK2 protein [Homo sapiens] gi|41351348|gb|AAH65511.1, SGK3 Serum/glucocorticoid regulated kinase 3 [Homo sapiens] gi|15929810|gb|AAH15326.1; PKC SUB-FAMILY OF AGC KINASES: PKC-alpha; Protein kinase C, alpha [Homo sapiens] gi|80479084|gb|AAI09275.1, PKC-beta; Protein kinase C, beta [Homo sapiens] gi|22209072|gb|AAH36472.1, PKC-beta; protein kinase C, beta isoform 1 [Homo sapiens] gi|47157322|ref|NP_997700.1, PKC-beta; protein kinase C, beta isoform 2 [Homo sapiens] gi|20127450|ref|NP_002729.2, PKC-delta; protein kinase C, delta [Homo sapiens] gi|47157325|ref|NP_997704.1, PKC-gamma; Protein kinase C, gamma [Homo sapiens] gi|28839171|gb|AAH47876.1, PKC-zeta 1; protein kinase C, zeta isoform 1 [Homo sapiens] gi|52486327|ref|NP_002735.3, PKC-zeta 2; protein kinase C, zeta isoform 2 [Homo sapiens] gi|75709226|ref|NP_001028753.1, PKC-epsilon; protein kinase C, epsilon [Homo sapiens] gi|4885563|ref|NP_005391.1, PKC-theta; protein kinase C, theta [Homo sapiens] gi|5453976|ref|NP_006248.1, PKC-iota; Homo sapiens protein kinase C, iota gb|NM_002740. In some aspects of the invention, the adaptive readout proteins or markers are from a non-human mammal.

Kits for Identification of Candidates for MBD Peptide Therapy

The invention provides kits for carrying out the methods of the invention. Kits of the invention comprise at least one probe specific for an Adaptive readout gene (and/or at least one affinity reagent specific for an Adaptive readout protein) and instructions for carrying out a method of the invention. More commonly, kits of the invention comprise at least two different Adaptive readout gene probes (or at least two affinity reagents specific for Adaptive readout proteins), where each probe/reagent is specific for a different Adaptive readout gene.

Kits comprising a single probe for an Adaptive readout gene (or affinity reagent specific for an Adaptive readout protein) will generally have the probe/reagent enclosed in a container (e.g., a vial, ampoule, or other suitable storage container), although kits including the probe/reagent bound to a substrate (e.g., an inner surface of an assay reaction vessel) are also contemplated. Likewise, kits including more than one probe/reagent may also have the probes/reagents in containers (separately or in a mixture) or may have the probes/affinity reagents bound to a substrate (e.g., such as an array or microarray).

A modified substrate or other system for capture of Adaptive readout gene transcripts or Adaptive readout proteins may also be included in the kits of the invention, particularly when the kit is designed for use in an array format assay.

In certain embodiments, kits according to the invention include the probes/reagents in the form of an array. The array includes at least two different probes/reagents specific for an Adaptive readout gene/protein (each probe/reagent specific for a different Adaptive readout gene/protein) bound to a substrate in a predetermined pattern (e.g., a grid). The localization of the different probes/reagents allows measurement of levels of a number of different Adaptive readout genes/.proteins in the same reaction.

The instructions relating to the use of the kit for carrying out the invention generally describe how the contents of the kit are used to carry out the methods of the invention. Instructions may include information as sample requirements (e.g., form, pre-assay processing, and size), steps necessary to measure the Adaptive readout gene(s), and interpretation of results.

Instructions supplied in the kits of the invention are typically written instructions on a label or package insert (e.g., a paper sheet included in the kit), but machine-readable instructions (e.g., instructions carried on a magnetic or optical storage disk) are also acceptable. In certain embodiments, machine-readable instructions comprise software for a programmable digital computer for comparing the measured values obtained using the reagents included in the kit.

Sequence "identity" and "homology", as referred to herein, can be determined using BLAST (Altschul, et al., 1990, *J. Mol. Biol.* 215(3):403-410), particularly BLASTP 2 as implemented by the National Center for Biotechnology Information (NCBI), using default parameters (e.g., Matrix 0 BLOSUM62, gap open and extension penalties of 11 and 1, respectively, gap x_dropoff 50 and wordsize 3). Unless referred to as "consecutive" amino acids, a sequence optionally can contain a reasonable number of gaps or insertions that improve alignment.

For testing efficacy of an agent believed to alter an adaptive signature, an effective amount of therapeutic agent is administered to a subject having a disease. In some embodiments, the agent is administered at about 0.001 to about 40 milligrams per kilogram total body weight per day (mg/kg/day). In some embodiments the agent is administered at about 0.001 to about 40 mg/kg/day.

The terms "subject" and "individual", as used herein, refer to a vertebrate individual, including avian and mammalian individuals, and more particularly to sport animals (e.g., dogs, cats, and the like), agricultural animals (e.g., cows, horses, sheep, and the like), and primates (e.g., humans).

The term "treatment" is used herein as equivalent to the term "alleviating", which, as used herein, refers to an improvement, lessening, stabilization, or diminution of a symptom of a disease. "Alleviating" also includes slowing or halting progression of a symptom.

For the purposes of this invention, a "clinically useful outcome" refers to a therapeutic or diagnostic outcome that leads to amelioration of the disease condition. "Inflammatory disease condition" means a disease condition that is typically accompanied by chronic elevation of transcriptionally active NF-kappa-B or other known intermediates of the cellular inflammatory response in diseased cells. The following intracellular molecular targets are suggested as examples:

"NF-kappa-B regulator domain" includes a binding domain that participates in transport of NF-kappa-B into the nucleus [Strnad J, et al. *J Mol Recognit.* 19(3):227-33, 2006; Takada Y, Singh S, Aggarwal B B. *J Biol Chem.* 279(15): 15096-104, 2004) and domains that participate in upstream signal transduction events to this transport. "P53 regulator domain" is the P53/MDM2 binding pocket for the regulatory protein MDM2 (Michl J, et al, *Int J Cancer.* 119(7): 1577-85, 2006). "IGF-signalling regulator domain" refers to the SH domain of Dok-1 which participates critically in IGF receptor signal transduction (Clemmons D and Maile L. *Mol Endocrinol.* 19(1): 1-11, 2005). "RAS active site domain" refers to the catalytic domain of the cellular Ras enzyme. "MYC regulator domain" refers to the amino-terminal regulatory region of c-myc or to its DNA-binding domain, both of which have been well-characterized (Luscher B and Larson L G. *Oncogene.* 18(19):2955-66, 1999). "HSP regulator domain" includes trimerization inhibitors of HSF-1 (Tai L. J et al. *J Biol Chem.* 277(1):735-45, 2002). "Survivin dimerization domain" refers to well-characterized sequences at the dimer interface of Survivin (Sun C, et al. *Biochemistry.* 44(1): 11-7, 2005). "Proteasome subunit regulator domain" refers to the target for hepatitis B virus-derived proteasome inhibitor which competes with PA28 for binding to the proteasome alpha4/MC6 subunit (Stohwasser R, et al. *Biol Chem.* 384(1): 39-49, 2003). "HIF1-alpha oxygen-dependent regulator domain" refers to the oxygen-dependent degradation domain within the HIF-1 protein (Lee J W, et al. *Exp Mol Med.* 36(1): 1-12, 2004). "Smad2" is mothers against decapentaplegic homolog 2 (*Drosophila*) (Konasakim K et al. J. Am. Soc. Nephrol. 14:863-872, 2003; Omata, M. et al. *J. Am. Soc. Nephrol.* 17:674-685, 2006). "Smad3" is mothers against decapentaplegic homolog 3 (*Drosophila*) (Roberts, A B et al *Cytokine Growth Factor Rev.* 17:19-27, 2006). "Src family kinases" refers to a group of proto-oncogenic tyrosine kinases related to a tyrosine kinase originally identified in Rous sarcoma virus (Schenone, S et al. *Mini Rev Med Chem* 7:191-201, 2007). Other suggested targets are PRR5 family proteins, IRS family proteins (including IRS-2 and IRS-1) and Akt family proteins (including Akt isoforms 1 to 4).

As used herein, "in conjunction with", "concurrent", or "concurrently", as used interchangeably herein, refers to administration of one treatment modality in addition to another treatment modality. As such, "in conjunction with" refers to administration of one treatment modality before, during or after delivery of the other treatment modality to the subject.

Techniques for the manipulation of recombinant DNA are well known in the art, as are techniques for recombinant production of proteins (see, for example, in Sambrook et al., Molecular Cloning: A Laboratory Manual, Vols. 1-3 (Cold Spring Harbor Laboratory Press, 2 ed., (1989); or F. Ausubel et al., Current Protocols in Molecular Biology (Green Publishing and Wiley-Interscience: New York, 1987) and periodic updates). Derivative peptides or small molecules of known composition may also be produced by chemical synthesis using methods well known in the art.

Homologous sequences are orthologous if they were separated by a speciation event: when a species diverges into two separate species, the divergent copies of a single gene in the resulting species are said to be orthologous. Orthologs, or orthologous genes, are genes in different species that are similar to each other because they originated from a common ancestor.

Homologous sequences are paralogous if they were separated by a gene duplication event: if a gene in an organism is duplicated to occupy two different positions in the same genome, then the two copies are paralogous. A set of sequences that are paralogous are called paralogs of each other. Paralogs typically have the same or similar function, but sometimes do not: due to lack of the original selective pressure upon one copy of the duplicated gene, this copy is free to mutate and acquire new functions.

Accordingly, the invention provides methods of treatment with fusions and/or conjugates of therapeutic or diagnostic molecules (such as agents) which are desired to be internalized into cells. The fusion partner molecules may be polypeptides, nucleic acids, or small molecules which are not normally internalized (e.g., because of large size, hydrophilicity, etc.). The fusion partner can also be an antibody or a fragment of an antibody. As will be apparent to one of skill in the art, such fusions/conjugates will be useful in a number of different areas, including pharmaceuticals (to promote internalization of therapeutic molecules which do not normally become internalized), gene therapy (to promote internalization of gene therapy constructs), and research (allowing 'marking' of cells with an internalized marker protein).

Therapeutic agents are preferably administered via oral or parenteral administration, including but not limited to intravenous (IV), intra-arterial (IA), intraperitoneal (IP), intramuscular (IM), intracardial, subcutaneous (SC), intrathoracic, intraspinal, intradermal (ID), transdermal, oral, sublingual, inhaled, and intranasal routes. IV, IP, IM, and ID administration may be by bolus or infusion administration. For SC administration, administration may be by bolus, infusion, or by implantable device, such as an implantable minipump (e.g., osmotic or mechanical minipump) or slow release implant. The agent may also be delivered in a slow release formulation adapted for IV, IP, IM, ID or SC administration. Inhaled agent is preferably delivered in discrete doses (e.g., via a metered dose inhaler adapted for protein delivery). Administration of a molecule comprising an agent via the transdermal route may be continuous or pulsatile. Administration of agents may also occur orally.

For parenteral administration, compositions comprising a therapeutic agent may be in dry powder, semi-solid or liquid formulations. For parenteral administration by routes other than inhalation, the composition comprising an agent is preferably administered in a liquid formulation. Compositions comprising an agent formulation may contain additional components such as salts, buffers, bulking agents, osmolytes, antioxidants, detergents, surfactants, and other pharmaceutical excipients as are known in the art.

A composition comprising an agent is administered to subjects at a dose of about 0.001 to about 40 mg/kg/day, more preferably about 0.01 to about 10 mg/kg/day, more preferably 0.05 to about 4 mg/kg/day, even more preferably about 0.1 to about 1 mg/kg/day.

As will be understood by those of skill in the art, the symptoms of disease alleviated by the instant methods, as well as the methods used to measure the symptom(s) will vary, depending on the particular disease and the individual patient.

Patients treated in accordance with the methods of the instant invention may experience alleviation of any of the symptoms of their disease.

EXAMPLES

Example 1

Adaptive Biochemical Signatures from Kidney Cells

Sixteen-week-old db/db mice exhibit significantly elevated blood glucose and albuminuria. Kidney mesangial cell matrix expansion and collagen-IV synthesis correlate with disease progression, but the underlying mechanism is unclear. Adaptive biochemical datasets were generated in cultured 293 kidney cells and in db/db mice.

Reagents: Humanin (WT) and S14G-Humanin were purchased from American Peptide Co, Sunnyvale, Calif. NPKC (AKKGFYKKKQCRPSKGRKRGFCWPSI-QITSLNPEWNET; SEQ ID NO:6) and P38 (AKKG-FYKKKQCRPSKGRKRGFCWAPSRKPALRVIIPQAGK; SEQ ID NO:7) peptides contain the MBD domain of IGFBP-3, which provides effective biodistribution, cell internalization and nuclear delivery for linked sequences were synthesized and purified by Genenmed Synthesis, Inc., S. San Francisco, Calif. Glycated-hemoglobin, amphoterin, TNF-alpha, EGF, resistin, insulin, SDKP, caffeine, rapamycin, and the antibodies anti-IRS1, anti-RAGE, anti-Fibronectin, anti-IRS1(Ser307) and anti-IRS2(Ser731) were purchased from Sigma Chemical Co., St Louis, Mo. The following reagents were obtained from EMD Chemicals, San Diego, Calif.: AKT (Ser473)-blocking peptide, AKT Inhibitors (II through IX), JNK Inhibitors II and III, SB203580, LY294002, PD98059. Phosphosafe tissue cell extract reagent was from Novagen, Madison, Wis. Cell culture reagents RPMI 1649, DMEM and FBS were from Hyclone, Logan, Utah. Protein Concentration Kit was purchased from Pierce Biotechnology, Rockford, Ill. Antibodies to the following antigens were purchased from the indicated suppliers: c-Jun(Ser63), c-Jun(ser73), c-myc (Ser62), c-myc(Thr58) (EMD Chemicals, San Diego Calif.); Erk1/2(Thr202/Tyr204), P38MAPK(T180/Y182), SAPK/JNK(Thr183/Ty185), P38-alpha/SAPK2a, c-myc (Thr58Ser52), PKC-betaII, phospho-PKC-alpha/betaII (Thr638/641), PKC-Delta, PKC-Delta/Theta, PKC-Theta, PKC-zeta/lambda, PKD/pKCmu (Ser916), PKD/PKCmu (Ser744/748), PKD/PKCmu, AKT(Thr308), AKT(Ser473), AKT1, AKT2, AKT3, MKK3/MKK6(Ser189/207), ATF2 (Thr71), paxillin (Y118), GSK3B(Ser9) (Cell Signaling, Danvers, Mass.); Collagen-IV and IRS-2 (RnD Systems, Minneapolis, Minn.).

293 kidney cell culture: Cells were passaged in DMEM plus 10% FBS and plated in 6-well plates. When 90-95% confluent, they were treated with different reagents for 4 hours. Cells were collected off plates and washed twice with 1×PBS. Extracts were made in 200 ul phosphosafe and diluted in 1×PBS to set up ELISAs.

Human mesangial cell culture: Human kidney mesangial cells and media were purchased from Lonza (Walkersville, Md.). Cells grown in mesangial cell basal media that were quiescent for two days were treated with glycosylated hemoglobin and peptides, and cell extracts were prepared and assayed by ELISA in exactly the same manner as described for 293 cells.

Animal studies: db/db mice were purchased from Jackson Laboratories. Animals with blood glucose below 200 mg/dL in Week 8 were sacrificed and used as null controls. Remaining animals were randomized into 4-8 animals per treatment group and were injected by subcutaneous bolus daily from week 8 through 13 (first experiment) or week 9 through 15 (second experiment). At the beginning and end of each experiment, each mouse was housed in an individual metabolic cage for a 24-hour urine collection. The volume of urine collected was recorded. Urine samples were assayed for albumin by ELISA and the total amount of albumin excreted calculated by multiplying the volume of urine by the concentration of albumin in the urine. Diabetes progression was monitored weekly during treatment by measuring blood glucose levels. Animals were sacrificed at week 13 (first experiment) or week 15 (second experiment). At termination, plasma and organs (right and left kidneys, pancreas, brain, heart, liver) were collected for preparation of tissue extracts and ELISA assays. Organ slices were ground in cell lysis buffer and total protein concentration was measured using a BCA protein assay kit.

Measurement of plasma glucose and insulin: Insulin levels were determined in plasma samples with the UltraSensitive Mouse Insulin ELISA from ALPCO Diagnostics (Windham, N.H.). Blood was collected in heparin-coated capillary tubes and red blood cells were separated by centrifugation at 5000 rpm for 5 minutes. Plasma glucose was assessed by pipetting 5 ul samples on glucometer strips and reading in the One Touch Basic Glucometer (LifeScan Canada Ltd., Burnaby, BC). Mice were fasted overnight prior to the glucose test.

ELISA assays: Extracts were diluted 1/25 and 100 ul of each sample was added to a 96-well plate. After 1 hour the plate was washed (3 times with 1×PBS+Tween). 3% BSA was added to the plates and incubated for 1 hour. The wash step was repeated and then primary antibody was added for 1 hour. Another wash step was followed by treatment with secondary antibody for 1 hour. Wash was then repeated and 100ul per well TMB added. After incubation for 15 minutes, the samples were read in a plate reader at 655 nm.

PI3-kinase-associated IRS-2 immunoprecipitation: Immunoprecipitation was done using the Catch and Release IP Kit (Millipore, Billerica Mass.) according to the manufacturer's specifications. Briefly, HEK 293 cells were treated with either saline, glycated hemoglobin or amphoterin for 4 hours. The cells were collected and washed 2 times and whole cell extracts were prepared in phosphosafe buffer. 300 ul of each extract was mixed with 10 ul anti-PI3-kinase antibody for 60 minutes at 4 degrees C. with gentle rocking. The samples were then applied to the column and centrifuged for 30 seconds. The column was washed 3 times and then 400 ul of elution buffer was added to the column and centrifuged at 5000 rpm for 30 seconds to collect all samples. The purified material was assayed for IRS-2 by ELISA.

Statistical analysis: Probability values (p values) were computed using Student T-test. Unless otherwise stated, p values are expressed relative to saline-treated controls. For two-dimensional dendograms, each biochemical marker was normalized over all 24 mice as $|x_i-\mu|/\sigma$, where $x_i$ is the biochemical marker for mouse i, and $\mu$ and $\sigma$ are the mean and standard deviation for that marker over all 24 mice. Biochemical markers were grouped into three categories: primary (3 markers: body weight, glucose, and albuminuria), kidney (14 markers), and spleen (8 markers). This resulted in three normalized matrices of markers: P (primary) of size 24×3, K (kidney) of size 24×14, and S (spleen) of size 24×8. Mice were grouped into four categories: control (mice 1-8), nephrilin (mice 9-15) and anephrilin (mice 18-24). To examine variation between groups of markers and variation between groups of mice, we hierarchically clustered (J. A. Hartigan, Clustering Algorithms. Wiley, N.Y., 1975) each of these three matrices P, K, and S along both markers and mice, using correlation distance (1—sample correlation between observations) and Ward's linkage in Matlab (The Mathworks, Natick, Mass.). Subsequently, concatenated matrices [P,K] and [P,S], along with concatenated submatrices were also hierarchically clustered using the same parameters.

Figure 2:
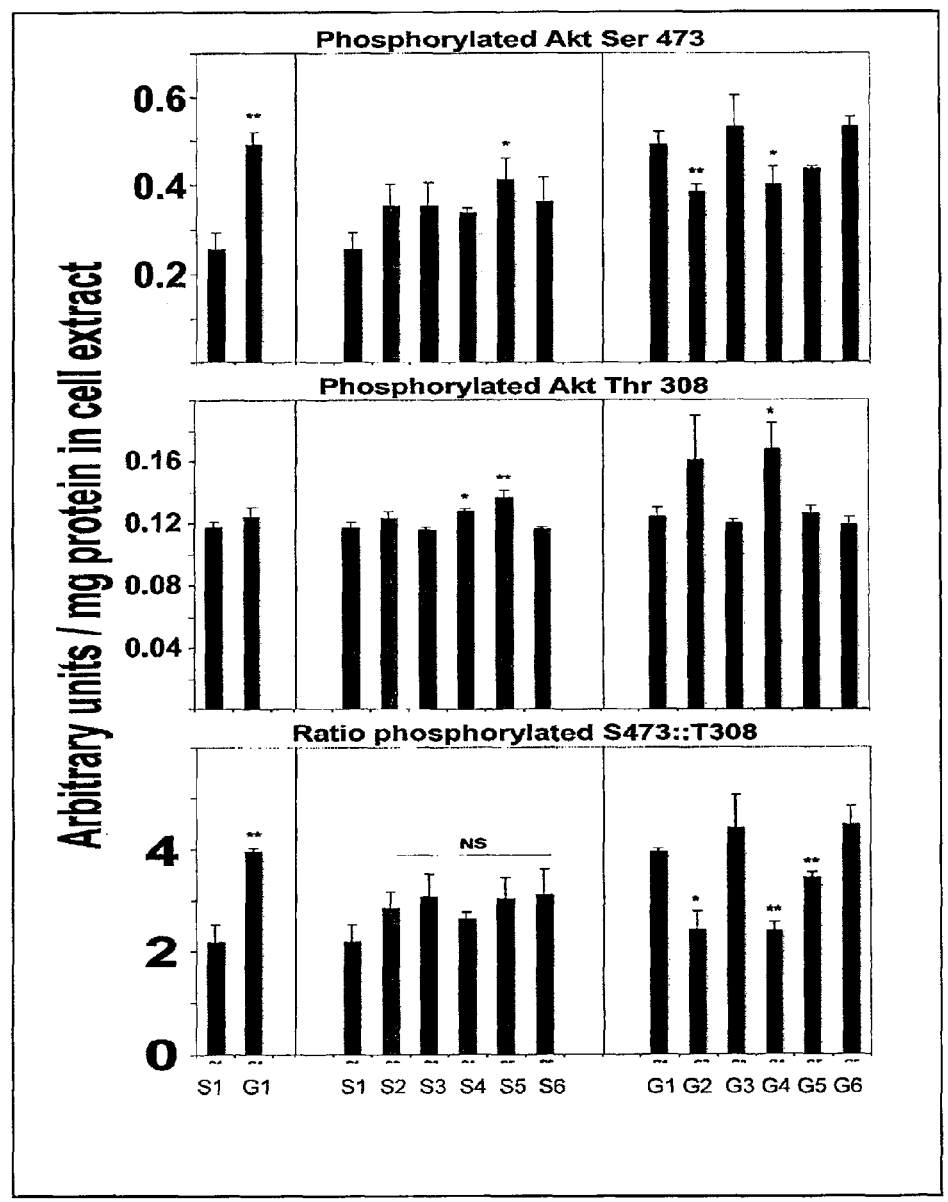
FIG. 2 shows altered patterns of phosphorylation of Akt/S473 and Akt/T308 in 293 kidney cells in response to metabolic and growth factors after 4-hour pre-treatment with glycated hemoglobin. Cells were treated and cell extracts prepared and assayed by ELISA as described in Materials and Methods. Grey bars=pre-treated with saline for 4 hours; Black bars=pretreated with glycated hemoglobin for 4 hours. Post-treatments (60 minutes): 1=Saline; 2=Insulin (10 uM); 3=IGF-I (100 ng/ml); 4=EGF (100 ng/ml); 5=TNF-alpha (10 ng/ml); 6=Resistin (50 ng/ml). $*p<0.05$; $**p<0.01$.

RAGE-adaptive elevation of IRS-2 and collagen-IV in 293 kidney cells: FIG. 1A shows that HEK293 kidney cells cultured in the presence of RAGE ligands amphoterin and glycated hemoglobin for 4 hours exhibit marked and sustained elevations of total cellular IRS-2 (but not IRS-1) and PI3-kinase-associated IRS-2. Fibronectin is significantly elevated only after 7-8 hours of treatment but collagen-IV elevation is sustained over several hours and parallels that of IRS-2 (FIG. 1B). A preliminary survey of cell extracts by ELISA (31 markers tested, data not shown) revealed an unusual pattern of sustained intracellular phosphorylation events affecting several key molecules including a remarkable and selective activation of PKB/Akt at Ser473 (but not Thr308), inactivation of IRS-1 (Ser307) but not IRS-2 (Ser731), and activation of PKCa/bII (Ser638/641) but not PKCmu (Ser916). In addition, JNK (Thr183/Tyr185) and the P38MAPK target ATF2 (Ser71) were selectively phosphorylated but ERK (Thr202/Tyr204) was not. These data are summarized in Table 1. In order to show that this set of RAGE-responsive adaptations in intracellular biochemistry leads to significantly modified responses to extracellular milieu we showed dramatically altered phosphorylation of key residues Thr308 and Ser473 in Akt in response to a range of growth, metabolic and inflammatory signals in cells that had been pre-treated with glycated hemoglobin (FIG. 2).

TABLE 1

Selected RAGE-induced biochemical readouts in 293 kidney cells.

| RAGE-Adaptive Marker | | Reference Marker | |
|---|---|---|---|
| ELISA | RAGE (4 hr) | ELISA | RAGE (4 hr) |
| Total IRS-2 | 1.47 ± 0.12 * | Total IRS-1 | 1.07 ± 0.02 |
| Total Akt1 | 1.27 ± 0.12 * | Total Akt2 | 0.81 ± 0.02 * |
| Total collagen-IV | 1.34 ± 0.06 ** | | |
| Phospho-Akt (S473) | 1.92 ± 0.11** | Phospho-Akt (T308) | 1.06 ± 0.05 |
| Phospho-IRS1 (S307) | 1.56 ± 0.10 * | Phospho-IRS2 (S731) | 1.03 ± 0.04 |
| Phospho-PKCα/bII (T638/641) | 1.52 ± 0.05 ** | Phospho-PKCmu (S916) | 0.95 ± 0.02 |
| Phospho-JNK (T183/Y185) | 1.38 ± 0.02 * | Phospho-ERK (T202/Y204) | 1.00 ± 0.09 |
| Phospho-ATF2 (T71) | 1.61 ± 0.08 * | | |

Cells were treated with glycated hemoglobin for 4 hours and ELISA values expressed relative to saline-treated controls, which were set to 1.0 arbitrary unit for each assay. Data are shown for a single representative experiment from 3 to 12 comparable experiments for each marker.
* $p < 0.05$
** $p < 0.01$ relative to saline controls.

Figure 3:
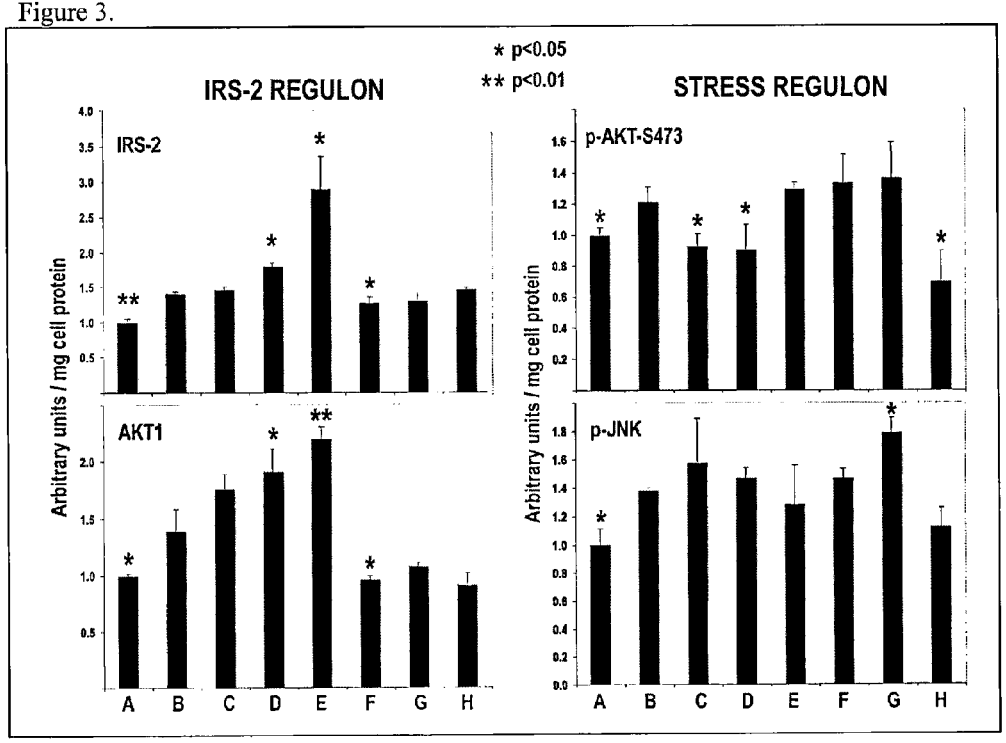
FIG. 3 shows the effect of selected inhibitors and bioactive peptides on RAGE-responsive biochemical indicia. 293 cells were incubated with saline (sample A in each panel) or glycated hemoglobin (samples B through H) for 4 hours either in the absence (sample B in each panel) or presence of inhibitors and bioactive peptides: C=Akt Inhibitor-IV, 10 uM; D=Rapamycin, 200 ng/ml; E=LY294002, 10 uM; F=wild type humanin, 20 ug/ml; G=NPKC peptide, 20 ug/ml; H=Akt-Ser473-blocking peptide, 10 ug/ml. Statistical significance shown versus the control sample B: $*p<0.05$; $**p<0.01$. See text for discussion of regulons.

Modulation of RAGE-activated biochemical changes by bioactive peptides and chemical inhibitors: The influence of selected inhibitors (Akt inhibitor IV, rapamycin and LY290004) and of the bioactive peptides humanin, NPKC and Akt-Ser473-blocking peptide on a selected set of RAGE-activated biochemical events is shown in FIG. 3. Humanin and NPKC peptides partially reverse the elevations in IRS-2 and Akt1 levels but not the selective phosphorylation of Akt-Ser473. Conversely, the latter can be blocked by Akt-Ser473-blocking peptide, without affecting IRS2 and Akt1 levels. LY290004, a selective inhibitor of PI3-kinase, and rapamycin, an mTORC1 inhibitor, further elevates IRS-2 and Akt, suggesting that these events are independent of the PI3-kinase pathway and mTORC1. Taken together, the pattern of inhibition and stimulation suggests the presence of two regulons, one defined by IRS-2 and Akt1 (IRS-2 regulon), and one by the selective phosphorylation of Akt-Ser473 and JNK-Thr183/Tyr185 (designated "stress regulon" because of JNK stress kinase). In human kidney mesangial cells pre-treated with glycated hemoglobin, IRS-2 levels are significantly reduced by exposure to either humanin-S14G or NPKC peptides (Table 2).

TABLE 2

IRS-2 levels in human kidney mesangial cells pre-treated with glycated hemoglobin are reduced by treatment with humanin and NPKC peptides.

| Peptide added | IRS-2 protein* | p value vs saline control |
|---|---|---|
| None (saline control) | 0.219 ± 0.002 | |
| 20 ug/ml humanin-S14G | 0.207 ± 0.001 | 0.0031 |
| 20 ug/ml NPKC | 0.193 ± 0.002 | 0.0001 |

*arbitrary units
Cells were treated with glycated hemoglobin, exposed to the indicated peptides for 24 hours, and whole cell extracts assayed for total IRS-2 protein as described in Materials and Methods.

Figure 4B:
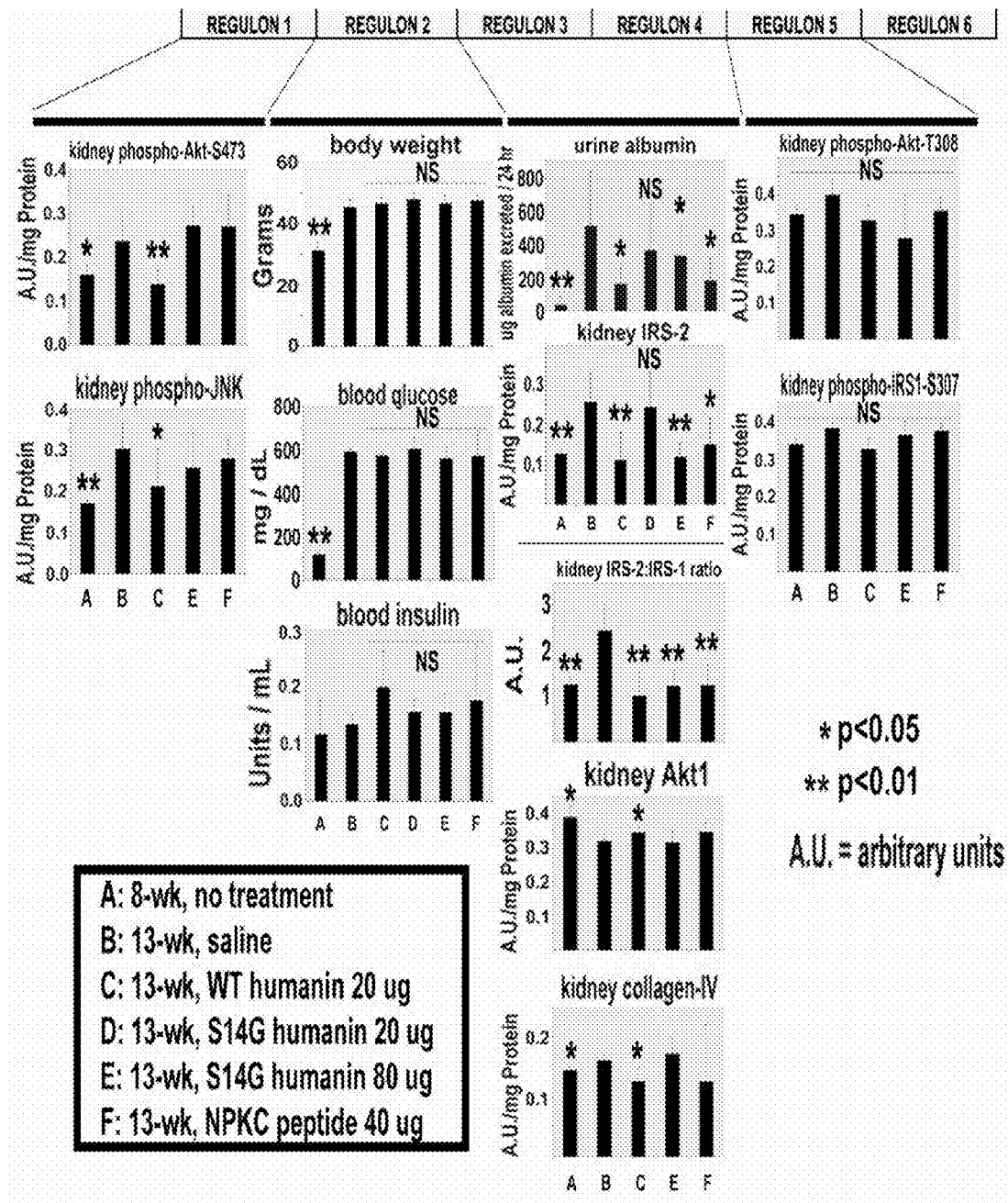

Effects of Humanin and NPKC peptides in vivo: In order to test the effect of subcutaneously-injected peptides in diabetic mice, 8-week old db/db mice were treated daily for 5 weeks with the indicated subcutaneous bolus doses of humanin or NPKC peptide. Wild type humanin was compared with the S14G substitution mutant (previously reported by others to be more active) and the wild type peptide was surprisingly found to be more effective. FIG. 4 shows the results obtained from measurement of (a) physiological markers such as urine albumin excretion, body weight, plasma glucose and insulin; and (b) ELISAs of kidney tissue extracts assayed for the markers defined in the RAGE-inducible set derived from 293 cell culture experiments, as summarized in Table 1. Peptide-mediated improvements in albuminuria occurred in the absence of any significant effect on body weight or on the elevated circulatory levels of glucose and insulin. For the purpose of displaying the data, kidney tissue markers are organized into six 'virtual regulons' defined by pairwise Pearson correlation analysis using ELISA value sets derived from 30 individual animals. The boundaries of each tightly correlated cluster defining a 'virtual regulon' are defined arbitrarily. Humanin and NPKC help normalize kidney IRS-2 levels and albuminuria. Humanin additionally influences collagen-IV and Akt1 (regulons 3 and 4), as seen in short-term cell culture experiments, but the direction of Akt1 modulation in chronic kidney disease is the opposite of what is observed with short-term treatment of 293 cells. Unlike the observed lack of effect in 293 kidney cell culture, chronic treatment of db/db mice with humanin helps normalize p-Akt-Ser473 and p-JNK-T183/Y185 levels, two tightly linked markers in regulon 1 ("stress regulon").

Uncoupling of collagen-IV synthesis from albuminuria in P38-peptide treated mice: In order to examine the possibility of an obligate relationship between collagen-IV synthesis and albuminuria, 9-week-old db/db mice were treated for 5 weeks with 40 ug/day subcutaneous bolus P38 peptide (an intracellular inhibitor of activated P38MAPK target ATF2 that includes an MBD domain sequence for cell internalization and nuclear delivery of the peptide in vivo) or humanin peptide. The results (Table 3) show a marked reduction of collagen-IV in P38 peptide-treated animals, but in these animals a significant exacerbation of albuminuria is observed. Kidney tissue IRS-2 is also elevated in P38-treated animals relative to saline treated controls (0.205±0.007 versus 0.184±0.009 arbitrary units; p=0.028). As in the first experiment, humanin reversed albuminuria.

TABLE 3

Modulation of collagen-IV in kidneys of 15-week old db/db mice treated with P38 peptide.

| TREATMENT | SALINE | HN-S14G (20 ug) | P38 (40 ug) |
|---|---|---|---|
| Group size (n) | 7 | 4 | 8 |
| Body weight (g) | 47.2 ± 2.4 | 46.9 ± 2.4 | 48.3 ± 2.4 |
| Glucose (mg/dL) | 604 ± 91 | 627 ± 100 | 609 ± 78 |
| Urinary Albumin | 1.22 ± 0.08 | 0.99 ± 0.12* | 1.44 ± 0.13** |
| Collagen-IV (a.u.) | 177 ± 20 | 149 ± 16* | 119 ± 38** |

Animals received daily subcutaneous bolus injection of P38 peptide (40 ug) or humanin-S14G (20 ug) between 9 and 14 weeks. At week 15, tissues were analyzed as described in Materials and Methods.
*p < 0.05;
**p < 0.01 relative to saline controls.

Conclusions: Treatment of db/db mice with bioactive peptides humanin and NPKC ameliorates albuminuria. Kidney tissue extracts were used to generate an adaptive dataset of biochemical markers. Correlation matrices based on these datasets reveal tightly clustered readouts which may, in turn, provide potentially fundamental insights into the adaptive circuitry of kidney cells. Readout clusters may be considered 'virtual regulons' for the purpose of guiding the hypothesis-driven design and development of novel and targeted therapeutic approaches to disease. The underlying assumption of this approach is that cellular responses to environmental insults are adaptive (or maladaptive, in the case of disease) and may expose universal aspects of adaptive logic such as characteristic responses to stress, enhanced plasticity or increased internality of decision-making as revealed, for example, by the temporarily modified response to endocrine and metabolic signals summarized in FIG. 2.

IRS-1 and IRS-2 proteins are central integrators of signaling traffic from cell membrane receptor tyrosine kinases responding to metabolic and growth signals, especially insulin and insulin-like growth factors and may be of particular relevance in diabetes. Although selective action of IRS isoforms has been proposed for specialized settings such as metastasis, the existence of a universal cellular logic switch based on the ratio of total active IRS-2 to IRS-1 has not been previously postulated. We show that in cultured 293 kidney cells challenged with glycated hemoglobin, as well as in kidney extracts from diabetic mice, a marked elevation in total IRS-2—but not IRS-1—levels is observed, accompanied by higher levels of phosphorylated IRS-1/Ser 307, which has been linked to insulin-resistance, but not of phosphorylated IRS-2/Ser 731. These types of changes would be expected to result in an increased involvement of IRS-2 in signaling events through the PI3 kinase pathway leading to activation of protein kinase B/Akt. We show a significantly elevated level of IRS-2 associated with PI3-kinase in cells treated with RAGE ligand.

Akt is a central consolidator of cellular logic. Fully-activated Akt is phosphorylated at two key residues, Thr308 and Ser473. Differential phosphorylation of Akt at these residues has been previously described. RAGE-mediated changes in 293 kidney cells involve altered signaling in the IRS-Akt axis. In db/db mice exhibiting elevated albuminuria, Akt1 levels are coupled to albumin excretion which is, in turn, coupled to Akt/Ser473 (but not Akt/Thr308) phosphorylation. In cultured 293 cells challenged with glycated hemoglobin, similarly linked responses are observed, with differential phosphorylation at Ser473 (inhibited by Ser473-blocking peptide), and consequently altered responses to insulin and EGF signaling. LY20004, a specific inhibitor of PI3-kinase, enhances the preferential phosphorylation of Ser473, suggesting that the event is independent of the PI3-kinase cascade. Although the rapamycin-insensitive mTOR complex mTORC2, which contains Rictor, has been recently implicated as the elusive PDK2 responsible for the phosphorylation of Akt-Ser473, rapamycin appears to reduce Ser473 phosphorylation in kidney cells. Other enzymes, such as PKC, have also been implicated as potential kinases for Akt-Ser473. Preferential phosphorylation of Akt-Ser473 in a PI3-kinase-independent manner may be part of the adaptive response characterized by elevated IRS-2 levels.

In this work we have surveyed a panel of intracellular biochemical readouts in cultured 293 kidney cells challenged with glycated hemoglobin and various chemical and peptide inhibitors. As shown in Table 2, similar data can be obtained from cultured human kidney mesangial cells. We elected to use 293 cells for most experiments because of better assay reproducibility, ease of culture and handling, and lower cost of materials for routine assay use.

Treatment of db/db mice with 20 ug/day subcutaneous bolus humanin or 40 ug/day NPKC peptide for 5 weeks ameliorates albuminuria and lowers IRS-2 levels. In addition, humanin helps normalize a cluster of RAGE-mediated biochemical effects, without affecting circulatory levels of glucose or insulin. Similar effects of humanin on biochemical markers can be observed as a result of short-term treatment of cultured kidney cells, except that the modulation of Akt1 is in the reverse direction. Treatment with wild type humanin is more effective than with the S14G variant, which has been shown to be more active in models of neurodegenerative disease.

In order to further understand the linkage between albuminuria and the biochemical readouts that may be significantly altered by disease, correlation matrices were generated from a dataset derived from ELISAs of kidney extracts prepared from 30 dbldb mice. In these matrices, biochemical readouts cluster into distinct 'virtual regulons'. Humanin and NPKC appear to influence the readouts that correlate most closely with albuminuria.

Inhibition of PKC using the NPKC peptide ameliorates albuminuria and reduces IRS-2 levels in the kidneys of treated mice. However, unlike humanin, NPKC does not normalize the elevation in phospho-Akt-Ser473 and phospho-JNK-Thr183/Tyr185, two markers comprising the so-called "stress regulon". In kidney extracts ($r=0.419$) and in 293 kidney cell culture ($r=0.502$), these two markers co-vary in response to environmental stimuli (data not shown). The uncoupling of responses to humanin and NPKC with respect to these markers suggests a distinction between indicia directly linked to albuminuria and other, more generalized, stress responses generated perhaps by exposure to hyperglycemic or hyperinsulinemic stress. Moreover, treatment of diabetic mice with peptide P38 (designed as an intracellular inhibitor of activated p38 MAPK), exacerbates albuminuria despite inhibiting collagen-IV production. This observation is consistent with the hypothesis that biochemical changes linked to a generalized stress response may not be as closely linked to albuminuria as are dysregulated IRS-2 levels.

Taken together, our data from kidney extracts and cultured kidney cells suggests that humanin acts by modifying biochemical parameters most closely associated with kidney disease as well as those associated with a more generalized stress response. On the other hand, NPKC may act on a more limited subset of biochemical indices. Collagen-IV synthesis, a canonical marker of matrix expansion, can be uncoupled from albuminuria in animals treated with P38 peptide: the peptide dramatically inhibits collagen synthesis but exacerbates protein excretion.

Although albuminuria is itself tightly linked to plasma glucose and body weight, humanin dramatically ameliorates protein excretion in the urine without exerting any significant impact on plasma glucose and insulin levels or body weight. Thus, markers driven by hyperglycemic or hyperinsulinemic stress may be separable from those that have a primary causal connection to kidney disease. Although a causal connection between IRS-2 elevation and albuminuria are not established by our data, we propose that the adaptive uncoupling of cellular IRS-2 levels from those of IRS-1 constitutes a potentially useful biochemical correlate of kidney disease in diabetic mice. The human peptide humanin, previously thought to have a function in neurodegenerative disease, has a profound effect on IRS-2 elevation both in vitro and in vivo, and may be a candidate for therapeutic intervention in kidney disease.

Example 2

Adaptive Signatures from Cancer Cells

Cell lines were challenged with glycated hemoglobin as described for human kidney cells in Example 1. Deltas (difference readings) of selected biochemical readouts were collected and analyzed to generate adaptive signatures.

Cells and cell culture. All cell lines were obtained from Cambrex or the American Type Culture Collection (ATCC).

They are well characterized and have been extensively used in vitro and in vivo. Breast cancer cell lines (MCF7, MDA-MB-435, MDA-MB-231, MX-1), leukemia cell lines (RPMI-8226, CCRF-CEM, MOLT-4), and prostate cancer cell lines (PC3, DU145, LNCAPs) were cultured in RPMI-1640 media supplemented with 5% FBS. Paired non-cancer and breast cancer cell lines (CRL-7481/CRL-7482, CRL-7364/CRL-7365) were cultured in DMEM media supplemented with 10% FBS. Normal cell lines such as MCF-10A, HMEC and HTB-125 were cultured in A, B, C media, serum-free, respectively. Cancer and metastatic cancer cell pairs (CCL-227/CCL-228, CRL-7425/CRL-7426, and CRL-1675/CRL-1676) were cultured in L-15 or MEM media with 10% FBS.

ELISA. Cells were lysed using cell lysis buffer (Clontech) or phospho-safe extraction reagent (Novagen) and lysate dilutions of 1:10 or 1:20 were loaded in triplicate in a 96-well plate format. Protein contained in the lysate was allowed to attach to coated plates for 1 hour at room temperature. The plates were then incubated for 1 hour at room temperature (or over night at 4° C.) in blocking buffer, consisting of 3% BSA in PBS with 0.05% Tween-20. The plates were washed and incubated with the diluted primary antibody for 1 hr on the shaker at room temperature. The plates were washed and then incubated with horseradish peroxidase—conjugated secondary antibody (Sigma Chemical Co, St. Louis, Mo.) for 45 minutes at room temperature. The antibody-antigen complex was visualized with Tetramethylbenzidine (TMB) liquid substrate system (Sigma) according to the manufacturer's protocol. Plates were read at 655 nm on the ELISA plate reader (Molecular Devices).

Mouse model. Successful engraftment of both human hematopoietic and non-hematopoietic xenografts requires the use of severe combined immuno deficient (scid) mice as neither bone marrow involvement nor disseminated growth are regularly observed using thymectomized, irradiated or nude mice. The mice used to establish a human-mouse xenograft model were purchased from Taconic. Mice were bred by crossing C57BL/6J gc KO mice to C57BL/10SgSnAi Rag-2 deficient mice. The gc KO is a deletion of the X-chromosome linked gc gene resulting in a loss of NK cells, a loss of the common g receptor unit shared by an array of cytokines that include IL-2, IL-4, IL-7, IL-9, and IL-15, and as a result only a residual number of T and B cells are produced. To eliminate this residual number of T and B cells, the gc mouse KO mouse was crossed with a C57BL/10SgSnAi recombinase activating-2 (Rag-2) deficient mouse (a loss of the Rag-2 gene results in an inability to initiate V(D)J lymphocyte receptor rearrangements, and mice will lack mature lymphocytes). MDA-MB-231 xenograft-bearing Rag-2 mice (10 mice per group, 3 groups, approx. 5×105 cancer cells injected per animal per group) are established through intra-cardial injection. Blood sampling and PCR analysis are carried out at weekly intervals. Approximately 100 ul blood is collected from the saphenous vein. PCR analysis is used on peripheral blood (PB) on Day 3 post-injection to determine whether animals have successfully established leukemia/cancer. Cancer cell count levels are monitored during and after treatment as well as at termination. PCR analysis on PB, bone marrow, spleen, liver and lung is used to quantify the cancer cells. At Day 3, prior to treatment, high levels of cancer cells should be seen in PB and low or no levels of human cancer cells in peripheral organs. Blood and peripheral organs were collected at termination and stored for further analysis (Day 18).

Figure 5:
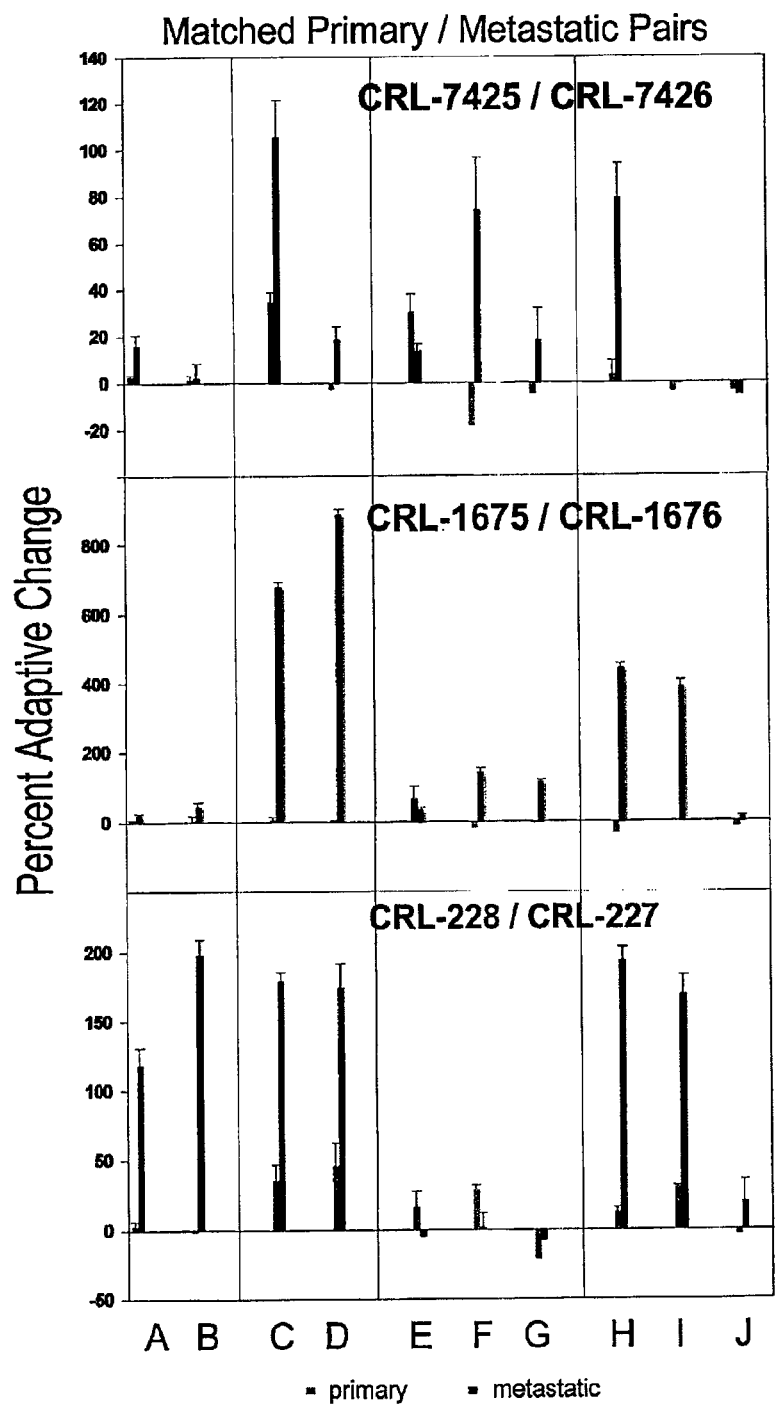
FIG. 5 shows adaptive signatures of primary versus metastatic cancer cells.

The results of an experiment comparing 3 matched pairs of primary tumor and metastatic cell lines derived from the same patient in each case are summarized in FIG. 5. The biochemical readouts are A: IRS-2; B: Akt2; C: phospho-Akt (Thr308); D: phospho-PKC a/bII; E: phospho-Akt (Ser473); F: phospho-JNK (Thr180/Tyr182); G: Akt1; H: ratio phospho-Akt T308/S473; I: phospho-IRS-1 (Ser307); J: IRS-1.

Figure 6:
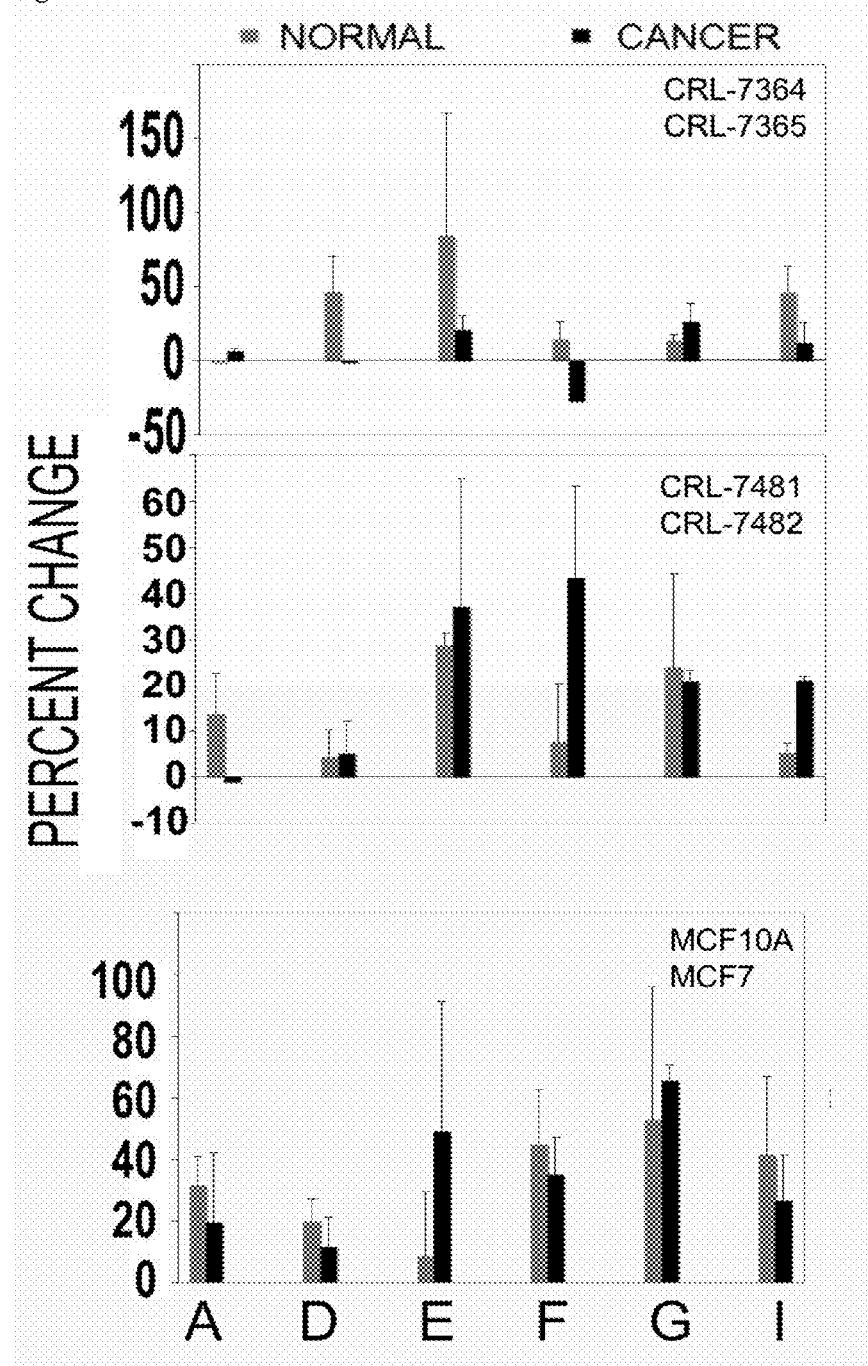
FIG. 6 shows adaptive signatures of matched normal versus cancer pairs.

As a control, the results of a similar experiment comparing 3 matched pairs of cancer/non-cancer cell lines are shown in FIG. 6. The biochemical readouts were labelled as in the experiment shown in FIG. 6.

Figure 7:
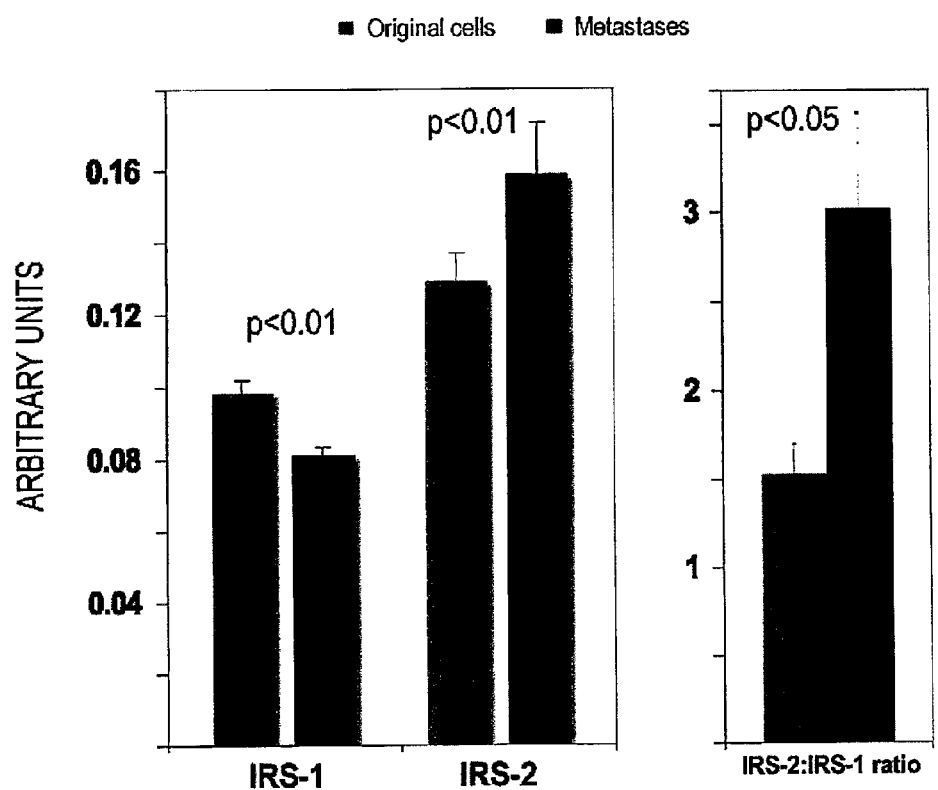
FIG. 7 shows adaptive signature of MDA-MB-231 metastases.

As a final control, MDA-MB-231 breast cancer cells were intracardially implanted in mice as described above. Visible liver metastases were recovered from 3 animals and cell extracts (assayed with human-specific antibodies) were compared with those from the original MDA-MB-231 cells in culture. The results of the comparison are shown in FIG. 7.

Example 3

Novel Inhibitors of Albuminuria

Derivation of nephrilin peptide. The peptide nephrilin was derived by fusing PRR-5/Protor sequences to the metal-binding domain (MBD) of IGFBP-3 which specifies cell targeting and internalization. Overlapping sequences from the PRR5-Rictor interaction domain were fused to MBD and tested for bioactivity. Peptide (20 ug/ml) bioactivity was measured in cultured human HEK293 kidney cells as previously described (Singh B K and Mascarenhas D D [2008] *Am J Nephrol.* 28: 890-899). Effectiveness was determined relative to 20 ug/ml humanin by measuring reversal of the elevation in levels of IRS-2, Aka1 and collagen-IV caused by treatment of HEK293 cells with glycated hemoglobin for 24 hours. Activities statistically different from the humanin control are reported (Table 4). The peptide nephrilin was selected for further study.

TABLE 4

Bioactivity of PRR5 peptides in HEK293 cells.

| | | RELATIVE ACTIVITY | | |
|---|---|---|---|---|
| Peptide | Sequence | IRS-2 | AKT1 | Col-IV |
| PEP11 | Ac-HESRGVTEDYLRLETLVQKVVGFYKKKQCRPSKGRKRGFCW-amide (SEQ ID NO: 10) | 1.14* | 1.10* | NS |
| PEP12 | Ac-GVTEDYLRLETLVQKVVSPYLGFYKKKQCRPSKGRKRGFCW-amide (SEQ ID NO: 11) | NS | 1.30* | 1.33* |

TABLE 4-continued

Bioactivity of PRR5 peptides in HEK293 cells.

| Peptide | Sequence | RELATIVE ACTIVITY | | |
|---|---|---|---|---|
| | | IRS-2 | AKT1 | Col-IV |
| PEP13 | Ac-LRLETLVQKVVSPYLGTYGLHGFYKKKQCRPSKGRKRGFCW-amide (SEQ ID NO: 12) | NS | NS | NS |
| nephrilin | Ac-RGVTEDYLRLETLVQKVVSKGFYKKKQCRPSKGRKRGFCW-amide (SEQ ID NO: 13) | 1.17* | 1.12* | 1.26* |
| humanin | Ac-*MAPRGFSCLLLLTSEIDLPVKRRA*-amide (SEQ ID NO: 1) | 1.00 | 1.00 | 1.00 |

Overlapping sequences from the Rictor: PRR5 interaction domain were fused to the MBD transporter and tested in human kidney cells. Activity is shown relative to humanin control. Significantly different results are shown. Amino acid residues in bold type are from the MBD sequence. (NS = not significantly different from humanin; * = p < 0.05).

Figure 8:
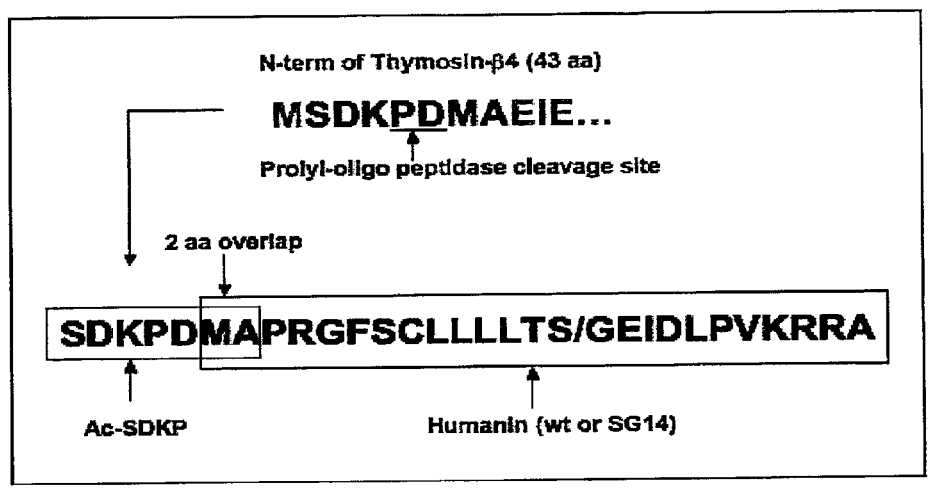
FIG. 8 shows an N-terminal fusion of SDKP tetrapeptide to humanin sequence. The natural cleavage site present in the thymosin-beta-4 precursor is preserved in the fusion sequence.

In a preliminary experiment in db/db mice, a full-length fusion of the Ac-SDKP tetrapeptide to the amino terminus of humanin (FIG. 8) was compared with humanin and Ac-SDKP. Table 5 shows 24-hr albumin excreted in urine. Although humanin was active at reducing albuminuria, neither Ac-SDKP alone nor full-length Ac-SDKP-humanin fusion was able to significantly reduce proteinuria in these animals. In order to test whether efficient cleavage of the tetrapeptide by prolyl oligopeptidase in vivo might require optimization of substrate length, we constructed and tested a series of peptide fusions of the Ac-SDKP tetrapeptide to the amino terminus of humanin followed by subsequent deletion of non-essential amino acid residues from the C-terminus of the humanin sequence. Table 6 shows the result of this screen in human kidney cells (Singh B K and Mascarenhas D D [2008] *Am J Nephrol.* 28: 890-899). Anephril (Ac-SDKPD-MAPRGFSCLLLLTGEIDLPV-amide; SEQ OD NO:14) was selected for further study as it is more active than humanin in cell culture assays.

TABLE 5

Albumin excreted in urine of 13-week old db/db mice.

| | | PERCENT ALBUMIN EXCRETED/24 HR | | |
|---|---|---|---|---|
| Peptide | n | MEAN | STDEV | P vs CONTROL |
| none (control) | 8 | 100.0 | 30.3 | |
| humanin | 6 | 53.0 | 20.9 | p < 0.01 |
| ac-SDKP | 4 | 78.8 | 13.7 | NS |
| ac-SDKP-humanin | 8 | 97.6 | 59.2 | NS |

Albumin excreted in urine of 13-week old db/db mice that had been treated for 5 weeks with humanin, SDKP or full-length SDKP-humanin fusion peptide administered once daily by subcutaneous bolus at 1 mg/kg from week 8 to week 13. Albumin numbers are standardized as a percentage by setting the control group to 100

(NS = not significantly different from control).

TABLE 6

Bioactivity of SDKP fusion peptides in HEK293 cells.

| Peptide | Sequence | Relative Activity | | |
|---|---|---|---|---|
| | | IRS-2 | AKT1 | Col-IV |
| PEP24-1 | Ac-SDKPD*MAPRGFSCLLLLTSEIDLPVKRRA*-amide (SEQ ID NO: 15) | NS | NS | NS |
| PEP24-2 | Ac-SDKPD*MAPRGFSCLLLLTGEIDLPVKRRA*-amide (SEQ ID NO: 16) | NS | NS | NS |
| PEP24-3 | Ac-SDKPD*MAPRGFSCLLLLTGEIDLPVKRR*-amide (SEQ ID NO: 17) | NS | NS | NS |
| PEP24-4 | Ac-SDKPD*MAPRGFSCLLLLTGEIDLPVKR*-amide (SEQ ID NO: 18) | 1.37* | NS | NS |
| PEP24-5 | Ac-SDKPD*MAPRGFSCLLLLTGEIDLPVK*-amide (SEQ ID NO: 19) | 1.37* | 1.23* | 1.30* |
| anephril | Ac-SDKPD*MAPRGFSCLLLLTGEIDLPV*-amide (SEQ ID NO: 14) | 1.51* | NS | 1.34* |
| humanin | Ac-*MAPRGFSCLLLLTSEIDLPVKRRA*-amide (SEQ ID NO: 1) | 1.00 | 1.00 | 1.00 |
| HN-S14G | Ac-*MAPRGFSCLLLLTGEIDLPVKRRA*-amide (SEQ ID NO: 2) | NS | NS | NS |

Activity is shown relative to humanin. Significantly different results are shown. Amino acid residues in italics are from the humanin sequence (NS = not significantly different from humanin; * = p < 0.05).

Figure 9:
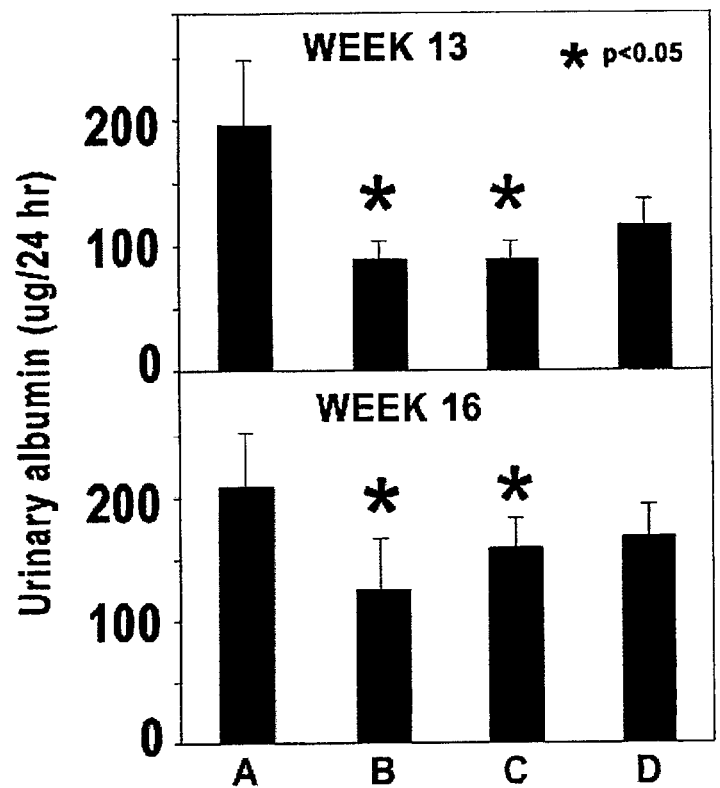
FIG. 9 shows Nephrilin and anephril reduce albuminuria in db/db mice. Urine collection and albumin assays were performed as described. A=saline; B=nephrilin (20 ug/day); C=anephril (20 ug/day); D=nephrilin+anephril (10 ug/day each peptide). Significance is shown relative to saline group.
Figure 10:
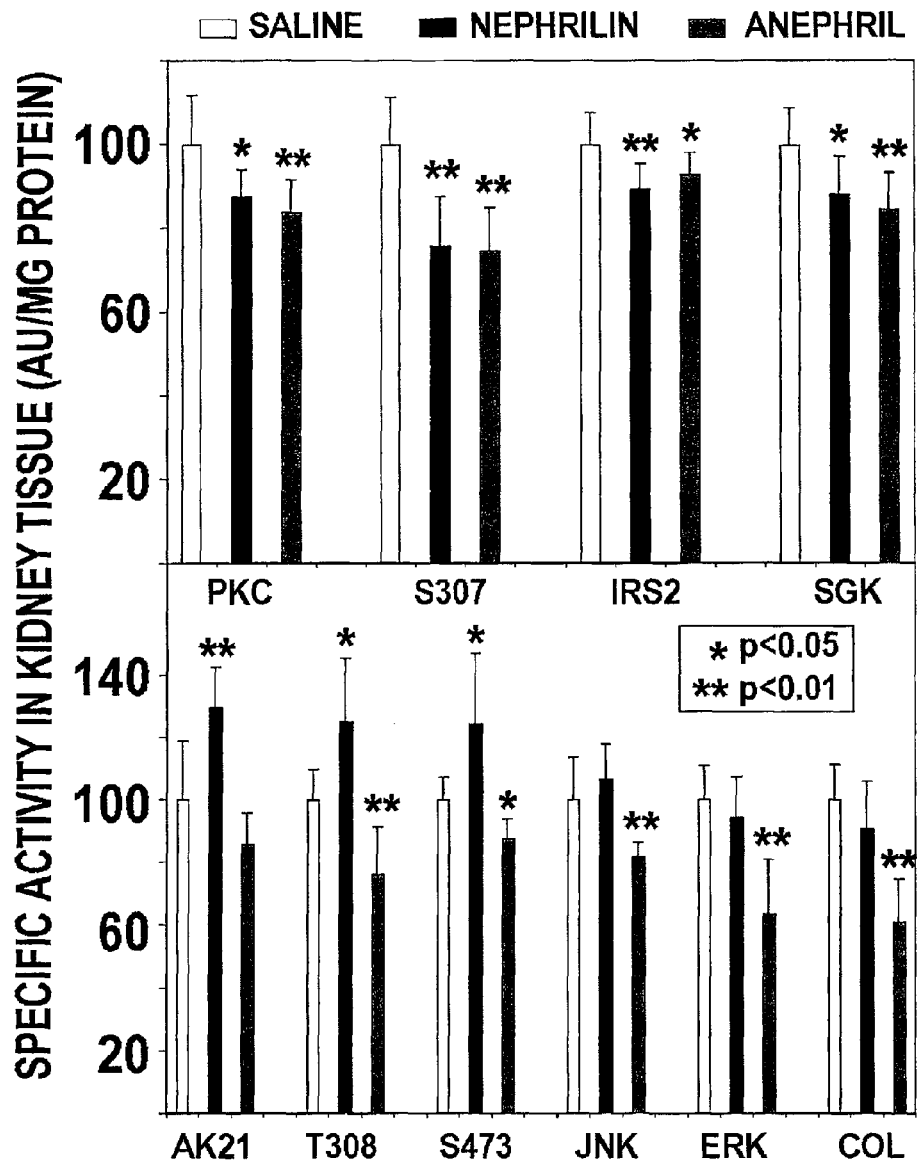
FIG. 10 shows biochemical analysis of kidney tissue extracts. Average values obtained from ELISA of left kidney tissue (8 animals per group). Groups A-C are shown. Results are expressed as specific activity (arbitrary units) per mg of total protein. PKC=phospho-PKCalpha/beta-Thr638/641; S307=phospho-IRS-1-Ser307; IRS2=total IRS-2; SGK=total SGK1; AK21=ratio of total Akt2::Akt1; T308=phospho-Akt-Thr308; S473=phospho-Akt-Ser473; JNK=phospho-JNK-Thr183/Ty185; ERK=phospho-Erk1/2-Thr202/Tyr204; COL=collagen-IV. Significance is shown relative to saline group.
Figure 11:
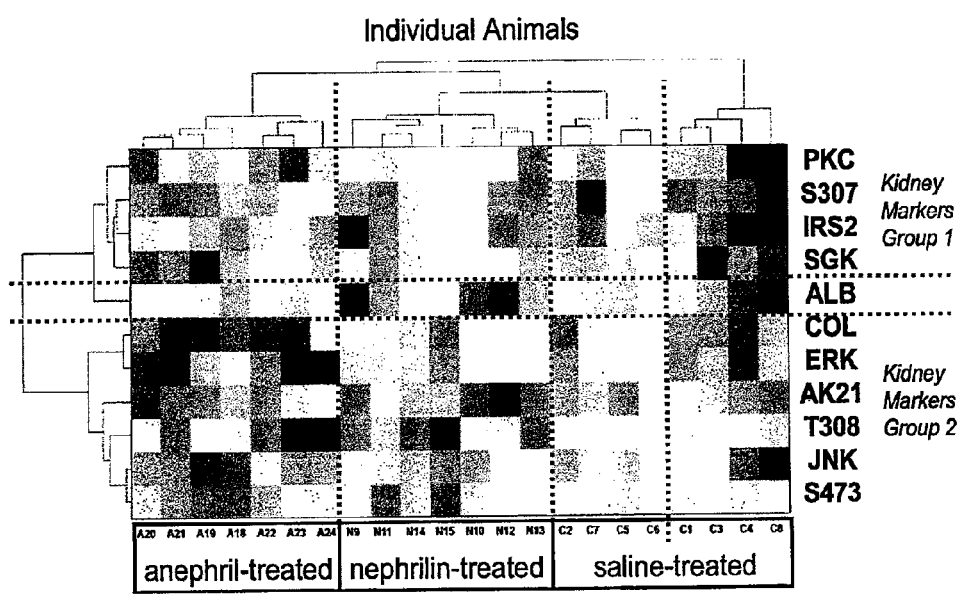
FIG. 11 shows a two-dimensional dendogram showing the clustering of animals and biochemical markers. Specific activity of each analyte was obtained by assaying left kidney tissue extracts from 16-week old db/db mouse groups A-D by ELISA. ALB=urinary albumin excreted in 24 hours; legend for biochemical markers same as for FIG. 10.
Figure 12:
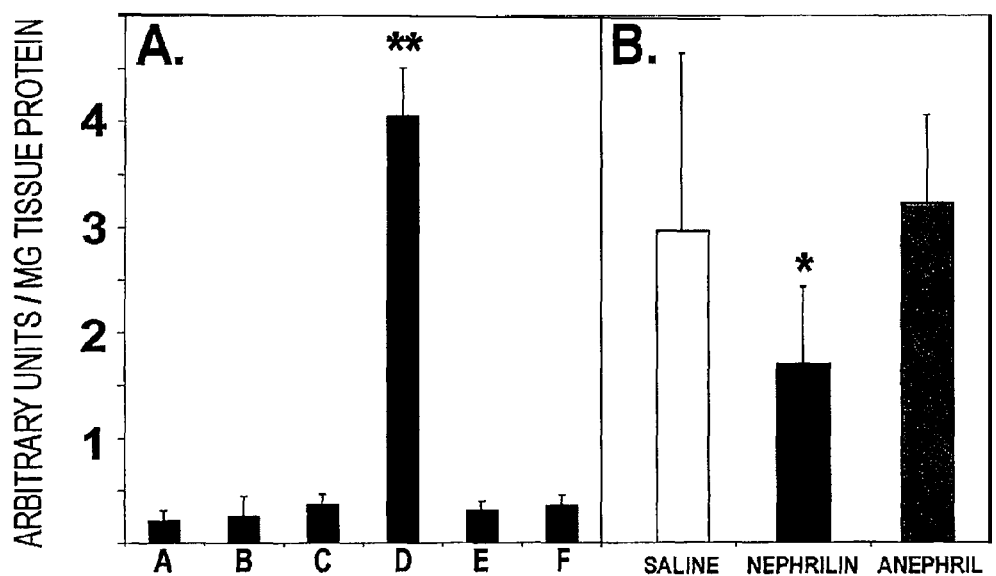
FIG. 12 shows elevated levels of SGK1 in spleens of db/db mice. Panel A. Average tissue specific activities of SGK1 by ELISA from all animals in study. A=kidney; B=liver; C=pancreas; D=spleen; E=heart; F=brain. Panel B. Average spleen SGK1 in each group (A-C); 8 animals per group. Significance is shown relative to saline group.

Peptides were injected by subcutaneous bolus injection into db/db mice as previously described (Singh B K and Mascarenhas D D [2008] *Am J Nephrol.* 28: 890-899). Briefly, peptide was administered to 9-week-old db/db mice (8 animals per group) by daily subcutaneous bolus injection. The treatment groups were as follows: saline, nephrilin (20 ug/day), anephril (20 ug/day) and nephrilin+anephril (10 ug each per day). Peptides were injected daily from week 9 through 15. Animals were sacrificed at Week 16. Albuminuria measurements were made at weeks 13 and 16 by housing animals in individual metabolic cages for a 24-hour urine collection. At termination, blood and organs (kidney, pancreas, spleen, liver, brain, heart) were collected for ELISA assays. Results of albumin measurements are shown in FIG. 9. Potent inhibition of albuminuria is observed in the case of animals treated with either nephrilin or anephril but the combination treatment was not as effective. No significant differences were found between groups in body weight, insulin or blood glucose (Table 7). Kidney tissue extracts were assayed by ELISA as previously described (Singh B K and Mascarenhas D D [2008] *Am J Nephrol.* 28: 890-899). As shown in FIG. 10, whereas one group of biochemical markers previously associated with kidney disease (IRS2, SGK1, p-PKC-Thr638/641, and p-IRS1-Ser307) were reduced by both peptides to a similar degree, a second group of previously implicated markers were reduced by anephril only (p-JNK, p-ERK, collagen-IV) or were affected in opposite ways by the two peptides (Akt isoforms and phospho-Akt). Two-dimensional statistical clustering using markers and animals was performed on the entire kidney tissue ELISA dataset and the results are shown in a 2-dimensional dendogram in FIG. 11. Two distinct groups of biochemical markers emerge clearly from this analysis and the peptides nephrilin and anephril do appear to have differential effects on these subsets, which we have labeled Group 1 and Group 2 markers. FIG. 12 shows that differential activity is also observed on the substantially elevated levels of SGK-1 measured in the spleens of db/db mice (FIG. 12). Nephrilin, but not anephril, dramatically lowered this elevation in spleen SGK1. Moreover, albuminuria correlated with spleen SGK-1 in control animals (r=0.32). When the levels of spleen SGK-1 are compared in two distinct control subgroups identified by cluster analysis of kidney markers (shown separated by the dotted line in FIG. 11) a statistically significant difference in spleen SGK1 is observed between the two control subgroups (147.5±37.2 vs. 52.6±5.6 AU/mg; p=0.013). The latter group also had lower kidney tissue levels of both Group 1 and 2 markers (−11.5±4.8% and −10.3±2.7% respectively; both p<0.01).

TABLE 7

Baseline characteristics of treatment groups.

| | Control | Nephrilin | Anephril | Nephrilin + Anephril |
|---|---|---|---|---|
| INITIAL (WEEK 9) | | | | |
| Body weight (gm) | 38.2 ± 3.2 | 37.8 ± 1.8 | 36.2 ± 2.4 | 37.6 ± 1.1 |
| Plasma glucose (mg/dL) | 342 ± 13 | 345 ± 14 | 347 ± 9 | 344 ± 11 |

TABLE 7-continued

Baseline characteristics of treatment groups.

| | Control | Nephrilin | Anephril | Nephrilin + Anephril |
|---|---|---|---|---|
| TERM (Week 16) | | | | |
| Body weight (gm) | 46.9 ± 3.2 | 46.4 ± 1.2 | 46.7 ± 1.2 | 47.2 ± 2.9 |
| Plasma insulin (arbitrary units) | 0.18 ± 0.09 | 0.18 ± 0.06 | 0.23 ± 0.08 | 0.22 ± 0.06 |
| Plasma glucose (mg/dL) | 473 ± 68 | 418 ± 136 | 432 ± 91 | 417 ± 89 |
| Kidney weight (mg) | 265 ± 63 | 218 ± 41 | 222 ± 46 | 226 ± 57 |

Figure 13:
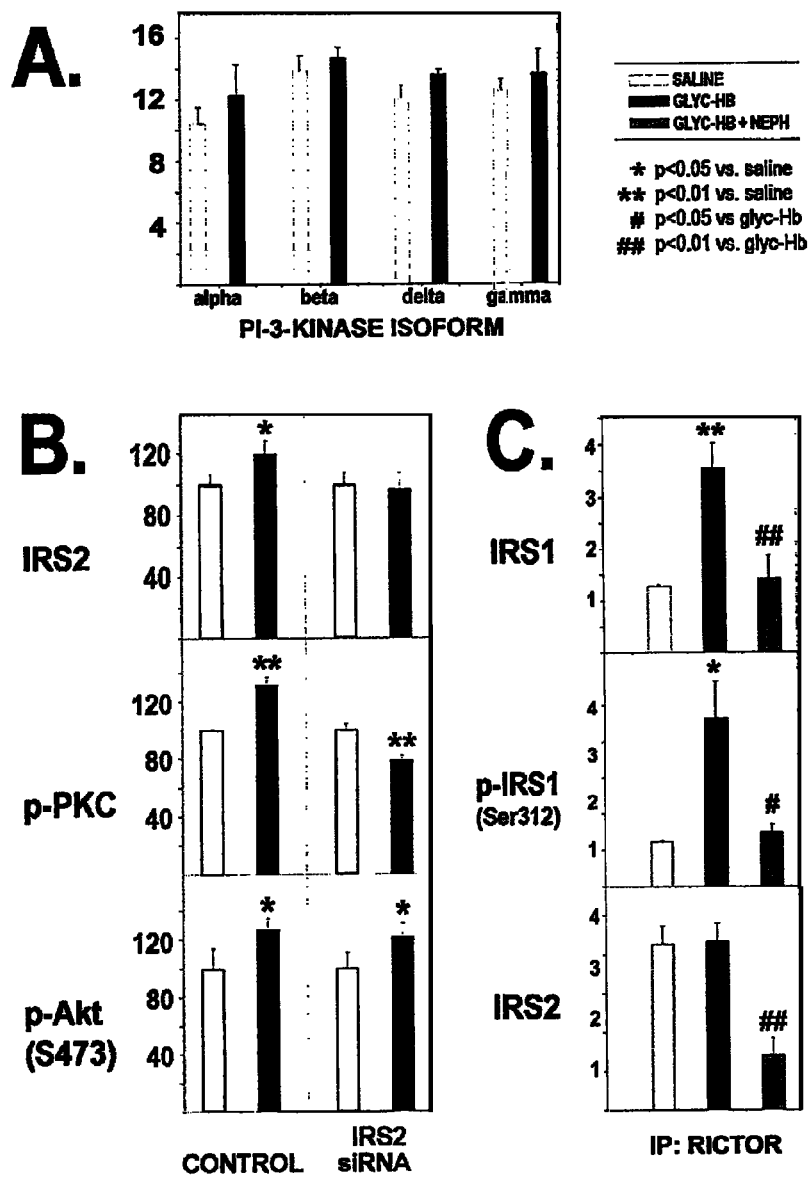
FIG. 13 shows potential mechanisms for IRS-mediated signaling. Specific activities of the indicated analytes in HEK293 human kidney cell extracts were measured by ELISA. Panel A Immunoprecipitation of extracts from saline- or glycated-hemoglobin (glyc-Hb)-treated cells using anti- IRS2 antibody, followed by ELISA for PI-3-kinase isoforms. Panel B. Cells were pre-treated either with saline or IRS2 siRNA followed by either saline or glycated hemoglobin. Panel C. Extracts prepared from cells treated with saline, glycated hemoglobin, or glycated hemoglobin plus 20 ug/ml nephrilin, were immunoprecipitated with anti-Rictor antibody followed by ELISA assay.

In order to investigate the potential mechanisms of action implicating IRS2 we treated cultured HEK293 cells with glycated hemoglobin for 24 hours. This treatment has been shown to induce the RAGE pathway (Singh B K and Mascarenhas D D [2008] *Am J Nephrol.* 28: 890-899). We first asked whether the elevated IRS-2 seen in these cells is reflected in an altered distribution between PI-3-kinase isoforms. PI-3-kinase is the canonical member of downstream signaling complexes previously associated with IRS proteins. Cell extracts were immunoprecipitated with anti-IRS2 antibody and the immunoprecipitate was assayed for each of the four PI-3-K isoforms by ELISA (FIG. 13A). No significant differences were observed. Next, we asked whether two AGC kinases (Akt and PKC) whose phosphorylation states are known to be affected by RAGE ligand, and which are also closely associated with albuminuria, lie downstream of the perturbation in IRS2 levels. Pretreatment of cells with anti-IRS-2 siRNA (FIG. 13B) abolishes the elevation in Group 1 markers IRS-2 and p-PKC but not of Group 2 marker p-Akt-S473. All three markers have been previously shown to elevate in response to treatment with glycated hemoglobin in these cells. This result suggests that elevations in PKC but not Akt phosphorylation are predicated on elevations in cellular IRS2 levels. Finally, ELISA of immunoprecipated Rictor complex shows that this complex contains IRS1 and IRS2 and that nephrilin interferes with this association (FIG. 13C). Phosphorylation of Ser312 in IRS-1 does not seem to affect the association of IRS1 with Rictor, which is significantly elevated by RAGE ligand.

Example 4

Dahl Rat Hypertension Model

The objective of the Dahl rat experiment was obtain plasma and urine samples from Dahl/ss rats treated with nephrilin peptide. The experiment had two parts:

(a) Part 1 involved samples from 6-week-old Dahl rats grown on HIGH-salt or LOW-salt diets for an additional 4 weeks. In addition SS13 rats (Dahl rat with chromosome 13 substitution from Norway Brown rat) were grown on HIGH-salt diet for 4 weeks. Urine, blood and kidney tissue were harvested from animals and snap frozen at sacrifice.

(b) Part 2 involved daily subcutaneous injection of saline or nephrilin (4 mg/kg) into Dahl rats grown on HIGH-salt diet for 4 weeks, then sacrificed under anesthesia.

TABLE 8

Drugs and Treatment:

| | | 1 Drug/Testing Agent | | | |
|---|---|---|---|---|---|
| Gr. | N | Agent | Mg/kg | Route | Schedule |
| 1# | 5 | vehicle | — | sc | qd × 24 |
| 2 | 5 | nephrilin | 4 | sc | qd × 24 |

Control Group

Male Dahl/ss rats 6-7 week old (Charles River) were fed AIN76A w/0.3% Na chow upon arrival at the facility, then switched to AIN76A w/8% Na (D05011703i; Research Diets) starting on Day 1. Rats were placed in metabolic cages following the final dose for a 12-hour acclimation time, then a 12-hour urine collection time. Blood was collected by terminal cardiac puncture under CO2 anesthesia and processed for plasma with K-EDTA preservation at −80 deg C. Left kidneys were snap frozen and stored at −80 deg C. for analysis. Tissues were extracted and assayed by ELISA as previously described [Singh B K et al (2010) *Metab Syndr Relat Disord.* 8(4): 355-363]. Segments of organ tissue were used for RNA extraction and gene array analysis (Phalanx Biotech, Inc., Palo Alto, Calif.).

Results are shown in FIGS. 14 and 15. Nephrilin treatment significantly reduces urinary albumin and lipocalin-2/NGAL and transdifferentiation—the epithelial-mesenchymal transition (EMT)—in kidney tissue. The elevated phosphorylation of PKC-beta-II-T641 and p66shc-S36 are both significantly inhibited by nephrilin. P66shc-S36 staining in nuclear stress bodies in kidney tissue is also significantly reduced by nephrilin treatment.

Example 5

AKI Models in CD-1 Mice

The objective of the AKI experiments was to collect samples to determine whether nephrilin peptide lessens stress to kidneys by cisplatin, gentamicin, or 50% glycerol treatment with secondary challenge of LPS. The protocol was as follows:

TABLE 9

Drugs and Treatment

| | | 1 Drug/Testing Agent | | | | 2 Drug/Testing Agent | | | | 3 Drug/Testing Agent | | | |
|---|---|---|---|---|---|---|---|---|---|---|---|---|---|
| Gr. | N | Agent | mg/kg | Rte | Schedule | Agent | mg/kg | Rte | Schedule | Agent | mg/kg | Rte | Schedule |
| 1# | 5 | saline | — | sc | qd × 7 | cisplatin | 30 | ip | days 5, 6 | LPS | 2 | sc | day 7 (18 hours post agent 2) |
| 2 | 5 | neph | 4 | sc | qd × 7 | cisplatin | 30 | ip | days 5, 6 | LPS | 2 | sc | day 7 (18 hours post agent 2) |
| 3# | 5 | saline | — | sc | qd × 7 | Gentamicin | 80 | ip | bid × 3 (start of day 4) | LPS | 2 | sc | day 7 (18 hours post agent 2) |
| 4 | 5 | neph | 4 | sc | qd × 7 | Gentamicin | 80 | ip | bid × 3 (start of Day 4) | LPS | 2 | sc | day 7 (18 hours post last agent 2 dose) |
| 5# | 5 | saline | — | sc | qd × 7 | 50% Glycerol | — | im | day 6 | LPS | 2 | sc | day 7 (18 hours post last agent 2 dose) |
| 6 | 5 | neph | 4 | sc | qd × 7 | 50% Glycerol | — | im | day 6 | LPS | 2 | sc | day 7 (18 hours post last agent 2 dose) |

Control Group 30 male 7-week-old CD-1 mice (Charles River) were placed in metabolic cages (one group of 5 mice per cage) for a 12 hour acclimation time (Days 2 and 6), then a 12 hour collection time (Days 3 and 7). Daily dosing by subcutaneous injection, as indicated in the table, volume 0.1 ml/mouse. Non-terminal collections of urine at Days 3 and 7. Blood was collected by retro-orbital bleed under isoflurane anesthesia prior to LPS on Day 7. Animals were sacrificed 2 hours later. Blood was collected by terminal cardiac puncture under CO2 anesthesia and processed for plasma with K-EDTA preservation at −80 deg C. Heart and kidney organs were snap frozen and stored at −80 deg C. for analysis. Tissues were extracted and assayed by ELISA as previously described [Singh B K et al (2010) *Metab Syndr Relat Disord.* 8(4): 355-363]. Segments of organ tissue were used for RNA extraction and gene array analysis (Phalanx Biotech, Inc).

Results are shown in FIG. 16. Nephrilin treatment significantly reduces urinary NGAL and the proinflammatory response post-LPS challenge.

Example 6

B16 Melanoma Metastasis Model

The objective of the B16 melanoma metastasis model experiment was to determine Lung Metastasis Dynamics between untreated and nephrilin-treated animals.

TABLE 10

Drugs and Treatment:

| | | 1 Drug/Testing Agent | | | |
|---|---|---|---|---|---|
| Gr. | N | Agent | mg/kg | Route | Schedule |
| 1# | 8 | Saline | — | sc | qd to end (start on day 2) |
| 2 | 8 | Nephrilin | 4 | sc | qd to end (start on day 2) |
| 3 | 2 | Unimplanted Control | — | — | — |
| 4 | 9 | Monitor Group | — | — | — |

Control Group

Set up 30 CR female B6D2F1 mice with $1 \times 10^5$ B16MET tumor cells in 0% Matrigel iv tail vein.
Cell Injection Volume is 0.2 mL/mouse.
Age at Start Date: 6 to 8 weeks.
Determine proper day for euthanasia of treatment groups by euthanizing 2 mice from Monitor Group each or every other day beginning on Day 9.
When lung colonies are large enough to see easily without crowding or growing together, euthanize all mice by cervical dislocation.
Remove the lungs from each mouse with minimal bronchus.
Count the lung colonies (metastasis) on the surface of the right lung.

Blood was collected by terminal cardiac puncture under $CO_2$ anesthesia and processed for plasma with K-EDTA preservation at $-80°$ C. Left lungs were snap frozen and stored at $-80°$ C. for analysis. Tissues were extracted and assayed by ELISA as previously described [Singh B K et al (2010) *Metab Syndr Relat Disord.* 8(4): 355-363]. Segments of organ tissue were used for RNA extraction and gene array analysis (Phalanx Biotech, Inc).

The results are shown in FIG. 18. They show that nephrilin significantly inhibits metastasis in this model. The effect was particularly marked in the lower regions of the lung (infereior and post-caval lobes).

Example 7

Gene Array and qPCR Analysis of Kidney and Heart Tissues from Various Models

The objective of this experiment was to identify genes that are controlled by disease processes regulated by mTORC2. Such genes are expected to be counter-regulated by nephrilin. The gene array comparisons performed, using a standardized platform provided by Phalanx Biotech, are shown in FIG. 17. Only signals that met statistical significance and minimum intensity criteria were considered in the analysis. By comparison of diabetic, hypertensive and rhabdomyolytic stress in kidneys of rodents genes commonly regulated in these diseases were identified. Nephrilin was found to counter-regulate three of these genes, ubiquitin carboxyterminal hydrolase 1 (UCHL1), Period 2 (PER2) a circadian clock gene, and B4galNT4. Using qPCR, the actual levels of these gene transcripts relative to GAPDH—a well-known housekeeping gene often used for this purpose—were established. These data are also shown in FIG. 17. These results show that UCHL1, PER2 and B4galNT4 are reporters for disease states regulated by mTORC2.

Example 8

Reagents for Screening Inhibitors and Agonists of mTORC2

Using the promoter regions of the genes UCHL1, PER2 or B4galNT4 fused to a downstream reporter gene, reporter cell lines may be constructed. As an example, the PER2 promoter was fused to the commercially available reporter gene SEAP purchased in the pSEAP2 plasmid vector (Clontech Inc. Palo Alto, Calif.). The PER2 promoter region was cloned by PCR into this vector. The map of the resulting construct, pSEAP-Basic-pPER2, is shown in FIG. 19, panel A. This plasmid may be used to assay mTORC2 inhibitors, either by transient transfection of pSEAPBasic-pPER2 into a suitable cell line such as HEK293, or by creating stable transfected cell line derivatives of such cell lines containing the PER2 promoter construct. The techniques for doing these types of experimental procedures are well known in the art.

Using an in vitro binding assay, candidate molecules may be screened for inhibition of binding of Rictor (the canonical component of mTORC2) to its binding partners, such as Protor/PRR5, Sin1, IRS1 and IRS2. The interaction region of Rictor and Protor has been mapped [Pearce L et al (2007) *Biochem J.* 405(3): 513-522]. We cloned the interaction region of human Rictor (amino acids 486-798) into a DsbA fusion vector, pYZ85832, designed to express mammalian protein in soluble form [Zhang Y et al (1998) *Protein Expr Purif.* 12(2): 159-165]. The insert sequence and bacterial expression of the resulting construct, pRICT1, is shown in FIG. 19, panel B. The prominently expressed RICT1 protein contains a natural biotinylation sequence NDIFEAQKIEWH (SEQ ID NO:8) by design. This simplifies the design of binding assays using the ELISA format. For example, candidate inhibitor molecules may be used in a competitive binding assay to disrupt binding interactions between RICT1 protein and Protor.

Although the foregoing invention has been described in some detail by way of illustration and example for purposes of clarity of understanding, the descriptions and examples should not be construed as limiting the scope of the invention.

I claim:

1. A method of treating diabetic kidney disease in a mammal comprising administering an effective amount of nephrilin (SEQ ID NO:13) to said mammal, wherein urinary albumin is reduced.

2. The method of claim 1, wherein spleen SGK-1 levels are also reduced.

3. A method of treating hypertension in a mammal comprising administering an effective amount of nephrilin (SEQ ID NO:13) to said mammal, wherein urinary albumin is reduced.

4. The method of claim 3, wherein urinary lipocalin-2/NGAL is also reduced.

5. A method of treating acute kidney injury caused by gentamycin or glycerol in a mammal comprising administering an effective amount of nephrilin (SEQ ID NO: 13) to said mammal, wherein urinary lipocalin-2/NGAL is reduced.

6. A method of treating melanoma in a mammal comprising administering an effective amount of nephrilin (SEQ ID NO:13) to said mammal, wherein lung metastases are reduced.

7. The method according to any one of claims 1-4, 5, or 6, wherein the mammal is a human.

8. The method according to any one of claims 1-4, 5, or 6, wherein the nephrilin in administered subcutaneously.

9. The method according to any one of claims 1-4, 5, or 6, wherein the nephrilin is administered at about 0.001 to about 40 ng/kg/day.

* * * * *

UNITED STATES PATENT AND TRADEMARK OFFICE
CERTIFICATE OF CORRECTION

PATENT NO. : 8,536,135 B2
APPLICATION NO. : 13/035844
DATED : September 17, 2013
INVENTOR(S) : Desmond Mascarenhas It is certified that error appears in the above-identified patent and that said Letters Patent is hereby corrected as shown below:

In the Claims:

At column 56, claim number 9, line number 57, please replace "ng/kg/day" with "mg/kg/day".

Signed and Sealed this
Nineteenth Day of November, 2013

Teresa Stanek Rea
*Deputy Director of the United States Patent and Trademark Office*

SEQUENCE LISTING

<160> NUMBER OF SEQ ID NOS: 19

<210> SEQ ID NO 1
<211> LENGTH: 24
<212> TYPE: PRT
<213> ORGANISM: Homo Sapiens

<400> SEQUENCE: 1

Met Ala Pro Arg Gly Phe Ser Cys Leu Leu Leu Leu Thr Ser Glu Ile
1               5                   10                  15

Asp Leu Pro Val Lys Arg Arg Ala
            20

<210> SEQ ID NO 2
<211> LENGTH: 24
<212> TYPE: PRT
<213> ORGANISM: Artificial Sequence
<220> FEATURE:
<223> OTHER INFORMATION: Synthetic Construct

<400> SEQUENCE: 2

Met Ala Pro Arg Gly Phe Ser Cys Leu Leu Leu Leu Thr Gly Glu Ile
1               5                   10                  15

Asp Leu Pro Val Lys Arg Arg Ala
            20

<210> SEQ ID NO 3
<211> LENGTH: 30
<212> TYPE: PRT
<213> ORGANISM: Artificial Sequence
<220> FEATURE:
<223> OTHER INFORMATION: Synthetic Construct

<400> SEQUENCE: 3

His Glu Ser Arg Gly Val Thr Glu Asp Tyr Leu Arg Leu Glu Thr Leu
1               5                   10                  15

Val Gln Lys Val Val Ser Pro Tyr Leu Gly Thr Tyr Gly Leu
            20                  25                  30

<210> SEQ ID NO 4
<211> LENGTH: 27
<212> TYPE: DNA
<213> ORGANISM: Artificial Sequence
<220> FEATURE:
<223> OTHER INFORMATION: Synthetic Construct

<400> SEQUENCE: 4
tagcaataat ccccatcctc catatat                                           27

<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
acttgtccaa tgatggtaaa agg                                               23

<210> SEQ ID NO 6
<211> LENGTH: 38
<212> TYPE: PRT
<213> ORGANISM: Artificial Sequence
<220> FEATURE:

<223> OTHER INFORMATION: Synthetic Construct

<400> SEQUENCE: 6

```
Ala Lys Lys Gly Phe Tyr Lys Lys Gln Cys Arg Pro Ser Lys Gly
 1               5                  10                  15

Arg Lys Arg Gly Phe Cys Trp Pro Ser Ile Gln Ile Thr Ser Leu Asn
            20                  25                  30

Pro Glu Trp Asn Glu Thr
         35
```

<210> SEQ ID NO 7
<211> LENGTH: 40
<212> TYPE: PRT
<213> ORGANISM: Artificial Sequence
<220> FEATURE:
<223> OTHER INFORMATION: Synthetic Construct

<400> SEQUENCE: 7

```
Ala Lys Lys Gly Phe Tyr Lys Lys Gln Cys Arg Pro Ser Lys Gly
 1               5                  10                  15

Arg Lys Arg Gly Phe Cys Trp Ala Pro Ser Arg Lys Pro Ala Leu Arg
            20                  25                  30

Val Ile Ile Pro Gln Ala Gly Lys
         35                  40
```

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

```
Asn Asp Ile Phe Glu Ala Gln Lys Ile Glu Trp His
 1               5                  10
```

<210> SEQ ID NO 9
<211> LENGTH: 326
<212> TYPE: PRT
<213> ORGANISM: Artificial Sequence
<220> FEATURE:
<223> OTHER INFORMATION: Synthetic Construct

<400> SEQUENCE: 9

```
Gly Pro Lys Pro Tyr Ser Leu His Leu Asp His Ile Ile Gln Lys Ala
 1               5                  10                  15

Ile Ala Thr His Gln Lys Arg Asp Gln Tyr Leu Arg Val Gln Lys Asp
            20                  25                  30

Ile Phe Ile Leu Lys Asp Thr Glu Glu Ala Leu Leu Ile Asn Leu Arg
        35                  40                  45

Asp Ser Gln Val Leu Gln His Lys Glu Asn Leu Glu Trp Asn Trp Asn
    50                  55                  60

Leu Ile Gly Thr Ile Leu Lys Trp Pro Asn Val Asn Leu Arg Asn Tyr
65                  70                  75                  80

Lys Asp Glu Gln Leu His Arg Phe Val Arg Arg Leu Leu Tyr Phe Tyr
                85                  90                  95

Lys Pro Ser Ser Lys Leu Tyr Ala Asn Leu Asp Leu Asp Phe Ala Lys
            100                 105                 110

Ala Lys Gln Leu Thr Val Val Gly Cys Gln Phe Thr Glu Phe Leu Leu
        115                 120                 125

Glu Ser Glu Glu Asp Gly Gln Gly Tyr Leu Glu Asp Leu Val Lys Asp
```

```
                130                 135                 140
Ile Val Gln Trp Leu Asn Ala Ser Ser Gly Met Lys Pro Glu Arg Ser
145                 150                 155                 160

Leu Gln Asn Asn Gly Leu Leu Thr Thr Leu Ser Gln His Tyr Phe Leu
                165                 170                 175

Phe Ile Gly Thr Leu Ser Cys His Pro His Gly Val Lys Met Leu Glu
                180                 185                 190

Lys Cys Ser Val Phe Gln Cys Leu Leu Asn Leu Cys Ser Leu Lys Asn
                195                 200                 205

Gln Asp His Leu Leu Lys Leu Thr Val Ser Ser Leu Asp Tyr Ser Arg
            210                 215                 220

Asp Gly Leu Ala Arg Val Ile Leu Ser Lys Ile Leu Thr Ala Ala Thr
225                 230                 235                 240

Asp Ala Cys Arg Leu Tyr Ala Thr Lys His Leu Arg Val Leu Leu Arg
                245                 250                 255

Ala Asn Val Glu Phe Phe Asn Asn Trp Gly Ile Glu Leu Leu Val Thr
                260                 265                 270

Gln Leu His Asp Lys Asn Lys Thr Ile Ser Ser Glu Ala Leu Asp Ile
            275                 280                 285

Leu Asp Glu Ala Cys Glu Asp Lys Ala Asn Leu His Ala Leu Ile Gln
290                 295                 300

Met Lys Pro Ala Leu Ser His Leu Gly Leu Asn Asp Ile Phe Glu Ala
305                 310                 315                 320

Gln Lys Ile Glu Trp His
            325

<210> SEQ ID NO 10
<211> LENGTH: 41
<212> TYPE: PRT
<213> ORGANISM: Artificial Sequence
<220> FEATURE:
<223> OTHER INFORMATION: Synthetic Construct

<400> SEQUENCE: 10

His Glu Ser Arg Gly Val Thr Glu Asp Tyr Leu Arg Leu Glu Thr Leu
1               5                   10                  15

Val Gln Lys Val Val Gly Phe Tyr Lys Lys Gln Cys Arg Pro Ser
            20                  25                  30

Lys Gly Arg Lys Arg Gly Phe Cys Trp
        35                  40

<210> SEQ ID NO 11
<211> LENGTH: 41
<212> TYPE: PRT
<213> ORGANISM: Artificial Sequence
<220> FEATURE:
<223> OTHER INFORMATION: Synthetic Construct

<400> SEQUENCE: 11

Gly Val Thr Glu Asp Tyr Leu Arg Leu Glu Thr Leu Val Gln Lys Val
1               5                   10                  15

Val Ser Pro Tyr Leu Gly Phe Tyr Lys Lys Gln Cys Arg Pro Ser
            20                  25                  30

Lys Gly Arg Lys Arg Gly Phe Cys Trp
        35                  40

<210> SEQ ID NO 12
<211> LENGTH: 41
<212> TYPE: PRT
```

```
<213> ORGANISM: Artificial Sequence
<220> FEATURE:
<223> OTHER INFORMATION: Synthetic Construct

<400> SEQUENCE: 12

Leu Arg Leu Glu Thr Leu Val Gln Lys Val Val Ser Pro Tyr Leu Gly
1               5                   10                  15

Thr Tyr Gly Leu His Gly Phe Tyr Lys Lys Gln Cys Arg Pro Ser
            20                  25                  30

Lys Gly Arg Lys Arg Gly Phe Cys Trp
        35                  40

<210> SEQ ID NO 13
<211> LENGTH: 40
<212> TYPE: PRT
<213> ORGANISM: Artificial Sequence
<220> FEATURE:
<223> OTHER INFORMATION: Synthetic Construct

<400> SEQUENCE: 13

Arg Gly Val Thr Glu Asp Tyr Leu Arg Leu Glu Thr Leu Val Gln Lys
1               5                   10                  15

Val Val Ser Lys Gly Phe Tyr Lys Lys Gln Cys Arg Pro Ser Lys
            20                  25                  30

Gly Arg Lys Arg Gly Phe Cys Trp
        35                  40

<210> SEQ ID NO 14
<211> LENGTH: 25
<212> TYPE: PRT
<213> ORGANISM: Artificial Sequence
<220> FEATURE:
<223> OTHER INFORMATION: Synthetic Construct

<400> SEQUENCE: 14

Ser Asp Lys Pro Asp Met Ala Pro Arg Gly Phe Ser Cys Leu Leu Leu
1               5                   10                  15

Leu Thr Gly Glu Ile Asp Leu Pro Val
            20                  25

<210> SEQ ID NO 15
<211> LENGTH: 29
<212> TYPE: PRT
<213> ORGANISM: Artificial Sequence
<220> FEATURE:
<223> OTHER INFORMATION: Synthetic Construct

<400> SEQUENCE: 15

Ser Asp Lys Pro Asp Met Ala Pro Arg Gly Phe Ser Cys Leu Leu Leu
1               5                   10                  15

Leu Thr Ser Glu Ile Asp Leu Pro Val Lys Arg Arg Ala
            20                  25

<210> SEQ ID NO 16
<211> LENGTH: 29
<212> TYPE: PRT
<213> ORGANISM: Artificial Sequence
<220> FEATURE:
<223> OTHER INFORMATION: Synthetic Construct

<400> SEQUENCE: 16

Ser Asp Lys Pro Asp Met Ala Pro Arg Gly Phe Ser Cys Leu Leu Leu
1               5                   10                  15

Leu Thr Gly Glu Ile Asp Leu Pro Val Lys Arg Arg Ala
```

```
<210> SEQ ID NO 17
<211> LENGTH: 28
<212> TYPE: PRT
<213> ORGANISM: Artificial Sequence
<220> FEATURE:
<223> OTHER INFORMATION: Synthetic Construct

<400> SEQUENCE: 17

Ser Asp Lys Pro Asp Met Ala Pro Arg Gly Phe Ser Cys Leu Leu Leu
1               5                   10                  15

Leu Thr Gly Glu Ile Asp Leu Pro Val Lys Arg Arg
            20                  25

<210> SEQ ID NO 18
<211> LENGTH: 27
<212> TYPE: PRT
<213> ORGANISM: Artificial Sequence
<220> FEATURE:
<223> OTHER INFORMATION: Synthetic Construct

<400> SEQUENCE: 18

Ser Asp Lys Pro Asp Met Ala Pro Arg Gly Phe Ser Cys Leu Leu Leu
1               5                   10                  15

Leu Thr Gly Glu Ile Asp Leu Pro Val Lys Arg
            20                  25

<210> SEQ ID NO 19
<211> LENGTH: 26
<212> TYPE: PRT
<213> ORGANISM: Artificial Sequence
<220> FEATURE:
<223> OTHER INFORMATION: Synthetic Construct

<400> SEQUENCE: 19

Ser Asp Lys Pro Asp Met Ala Pro Arg Gly Phe Ser Cys Leu Leu Leu
1               5                   10                  15

Leu Thr Gly Glu Ile Asp Leu Pro Val Lys
            20                  25
```